(12) United States Patent
Mao et al.

(10) Patent No.: US 9,783,566 B2
(45) Date of Patent: Oct. 10, 2017

(54) NON-CALORIC SWEETENERS AND METHODS FOR SYNTHESIZING

(71) Applicant: Conagen Inc., Bedford, MA (US)

(72) Inventors: Guohong Mao, Burlington, MA (US); Xiaodan Yu, Lexington, MA (US)

(73) Assignee: Conagen Inc., Bedford, MA (US)

( * ) Notice: Subject to any disclaimer, the term of this patent is extended or adjusted under 35 U.S.C. 154(b) by 0 days.

(21) Appl. No.: 14/873,481

(22) Filed: Oct. 2, 2015

(65) Prior Publication Data

US 2016/0097072 A1    Apr. 7, 2016

Related U.S. Application Data

(60) Provisional application No. 62/098,929, filed on Dec. 31, 2014, provisional application No. 62/059,498, filed on Oct. 3, 2014.

(51) Int. Cl.

| C07H 1/00 | (2006.01) |
|---|---|
| C07H 15/24 | (2006.01) |
| C12P 19/56 | (2006.01) |
| C07D 413/14 | (2006.01) |
| A23L 2/60 | (2006.01) |
| C07H 15/256 | (2006.01) |
| A23L 27/30 | (2016.01) |

(52) U.S. Cl.
CPC ............... C07H 15/24 (2013.01); A23L 2/60 (2013.01); A23L 27/36 (2016.08); C07H 1/00 (2013.01); C07H 15/256 (2013.01); C12P 19/56 (2013.01); A23V 2002/00 (2013.01)

(58) Field of Classification Search
CPC .. A23L 2/60; A23L 27/36; C07H 1/00; C07H 15/24; C12P 19/56; C07D 413/14
See application file for complete search history.

(56) References Cited

U.S. PATENT DOCUMENTS

| 9,567,619 B2 | 2/2017 | Mao et al. |
|---|---|---|
| 9,643,990 B2 | 5/2017 | Mao et al. |
| 2013/0071521 A1 | 3/2013 | Lee et al. |
| 2014/0099403 A1 | 4/2014 | Prakash et al. |
| 2014/0234511 A1 | 8/2014 | Hansen et al. |
| 2014/0271996 A1 | 9/2014 | Prakash et al. |
| 2014/0329281 A1 | 11/2014 | Houghton-Larsen |
| 2014/0357588 A1 | 12/2014 | Markosyan et al. |
| 2015/0315623 A1* | 11/2015 | Mao ............... C12N 9/1062 536/18.1 |
| 2016/0015064 A1 | 1/2016 | Luo et al. |
| 2016/0095338 A1 | 4/2016 | Mao et al. |
| 2016/0097070 A1 | 4/2016 | Mao et al. |
| 2016/0097071 A1 | 4/2016 | Mao et al. |
| 2016/0097072 A1 | 4/2016 | Mao et al. |
| 2016/0153018 A1 | 6/2016 | Mao et al. |

FOREIGN PATENT DOCUMENTS

| WO | 2013022989 A2 | 2/2013 |
|---|---|---|
| WO | 2013176738 A1 | 11/2013 |
| WO | 2014122328 A1 | 8/2014 |
| WO | 2014146135 A2 | 9/2014 |
| WO | 2014186250 A1 | 11/2014 |
| WO | WO 2016/054534 A1 | 4/2016 |
| WO | WO 2016/054540 A1 | 4/2016 |
| WO | WO 2016/054544 A1 | 4/2016 |
| WO | WO 2016/054548 A1 | 4/2016 |

OTHER PUBLICATIONS

Ibrahim et al. Minor Diterpene Glycosides from the Leaves of Stevia Rebaudiana. Journal of Natural Products. vol. 77, Apr. 23, 2014, pp. 1231-1235.
Prakash et al. Isolation and Structure Elucidation of Rebaudioside D2 from Bioconversion Reaction of Rebaudioside A to Rebaudioside D. Natural Product Communications. vol. 9, No. 8, Aug. 2014. pp. 1135-1138.
International Search Report and Written Opinion in PCT/US2015/053789 mailed Dec. 18, 2015.
Prakash et al. Development of Next Generation Stevia Sweetener: Rebaudioside M. Foods vol. 3, pp. 162-175, Feb. 27, 2014.
Broun et al., Catalytic plasticity of fatty acid modification enzymes underlying chemical diversity of plant lipids. Science, 1998, vol. 282: 1315-1317.
Devos et al., Practical limits of function prediction. Proteins: Structure, Function, and Genetics, 2000, vol. 41: 98-107.
Seffernick et al., Melamine deaminase and Altrazine chlorophydrolase: 98 percent identical functionality different. J. Bacteriol., 2001, vol. 183 (8): 2405-2410.
Whisstock et al., Prediction of protein function from protein sequence. Q. Rev. Biophysics., 2003, vol. 36 (3): 307-340.
Witkowski et al., Conversion of b-ketoacyl synthase to a Malonyl Decarboxylase by replacement of the active cysteine with glutamine. Biochemistry, 1999, vol. 38: 11643-11650.

* cited by examiner

*Primary Examiner* — Kagnew H Gebreyesus
(74) *Attorney, Agent, or Firm* — Wolf, Greenfield & Sacks, P.C.; Byron V. Olsen

(57) ABSTRACT

Disclosed are steviol glycosides referred to as rebaudioside V and rebaudioside W. Also disclosed are methods for producing rebaudioside M (Reb M), rebausoside G (Reb G), rebaudioside KA (Reb KA), rebaudioside V (Reb V) and rebaudioside (Reb W).

7 Claims, 26 Drawing Sheets

Reb M

SEQUENCE LISTING

```
<160> NUMBER OF SEQ ID NOS: 12

<210> SEQ ID NO 1
<211> LENGTH: 458
<212> TYPE: PRT
<213> ORGANISM: Artificial Sequence
<220> FEATURE:
<223> OTHER INFORMATION: Synthetic Polypeptide

<400> SEQUENCE: 1

Met Glu Asn Lys Thr Glu Thr Thr Val Arg Arg Arg Arg Ile Ile
1               5                   10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
                100                 105                 110

Glu Glu Asp Glu Glu Val Ser Cys Leu Ile Thr Asp Ala Leu Trp Tyr
            115                 120                 125

Phe Ala Gln Ser Val Ala Asp Ser Leu Asn Leu Arg Arg Leu Val Leu
        130                 135                 140

Met Thr Ser Ser Leu Phe Asn Phe His Ala His Val Ser Leu Pro Gln
145                 150                 155                 160

Phe Asp Glu Leu Gly Tyr Leu Asp Pro Asp Asp Lys Thr Arg Leu Glu
                165                 170                 175
```

```
Glu Gln Ala Ser Gly Phe Pro Met Leu Lys Val Lys Asp Ile Lys Ser
            180                 185                 190

Ala Tyr Ser Asn Trp Gln Ile Leu Lys Glu Ile Leu Gly Lys Met Ile
        195                 200                 205

Lys Gln Thr Lys Ala Ser Ser Gly Val Ile Trp Asn Ser Phe Lys Glu
    210                 215                 220

Leu Glu Glu Ser Glu Leu Glu Thr Val Ile Arg Glu Ile Pro Ala Pro
225                 230                 235                 240

Ser Phe Leu Ile Pro Leu Pro Lys His Leu Thr Ala Ser Ser Ser Ser
                245                 250                 255

Leu Leu Asp His Asp Arg Thr Val Phe Gln Trp Leu Asp Gln Gln Pro
            260                 265                 270

Pro Ser Ser Val Leu Tyr Val Ser Phe Gly Ser Thr Ser Glu Val Asp
        275                 280                 285

Glu Lys Asp Phe Leu Glu Ile Ala Arg Gly Leu Val Asp Ser Lys Gln
    290                 295                 300

Ser Phe Leu Trp Val Val Arg Pro Gly Phe Val Lys Gly Ser Thr Trp
305                 310                 315                 320

Val Glu Pro Leu Pro Asp Gly Phe Leu Gly Glu Arg Gly Arg Ile Val
                325                 330                 335

Lys Trp Val Pro Gln Gln Glu Val Leu Ala His Gly Ala Ile Gly Ala
            340                 345                 350

Phe Trp Thr His Ser Gly Trp Asn Ser Thr Leu Glu Ser Val Cys Glu
        355                 360                 365

Gly Val Pro Met Ile Phe Ser Asp Phe Gly Leu Asp Gln Pro Leu Asn
    370                 375                 380

Ala Arg Tyr Met Ser Asp Val Leu Lys Val Gly Val Tyr Leu Glu Asn
385                 390                 395                 400

Gly Trp Glu Arg Gly Glu Ile Ala Asn Ala Ile Arg Arg Val Met Val
                405                 410                 415

Asp Glu Glu Gly Glu Tyr Ile Arg Gln Asn Ala Arg Val Leu Lys Gln
            420                 425                 430

Lys Ala Asp Val Ser Leu Met Lys Gly Gly Ser Ser Tyr Glu Ser Leu
        435                 440                 445

Glu Ser Leu Val Ser Tyr Ile Ser Ser Leu
    450                 455

<210> SEQ ID NO 2
<211> LENGTH: 1377
<212> TYPE: DNA
<213> ORGANISM: Artificial Sequence
<220> FEATURE:
<223> OTHER INFORMATION: Synthetic Polynucleotide

<400> SEQUENCE: 2
atggagaata agacagaaac aaccgtaaga cggaggcgga ggattatctt gttccctgta      60
ccatttcagg gccatattaa tccgatcctc caattagcaa cgtcctcta ctccaaggga     120 ttttcaataa caatcttcca tactaacttt aacaagccta aaacgagtaa ttatcctcac     180
tttacattca ggttcattct agacaacgac cctcaggatg agcgtatctc aaatttacct     240
acgcatggcc ccttggcagg tatgcgaata ccaataatca tgagcatgg agccgatgaa     300 ctccgtcgcg agttagagct tctcatgctc gcaagtgagg aagacgagga agtttcgtgc     360
ctaataactg atgcgctttg gtacttcgcc aatcagtcg cagactcact gaatctacgc     420
cgtttggtcc ttatgacaag ttcattattc aactttcacg cacatgtatc actgccgcaa     480
```

| | | | | |
|---|---|---|---|---|
| tttgacgagt | tgggttacct | ggacccggat | gacaaaacgc | gattggagga acaagcgtcg | 540 |
| ggcttcccca | tgctgaaagt | caaagatatt | aagagcgctt | atagtaattg gcaaattctg | 600 |
| aaagaaattc | tcggaaaaat | gataaagcaa | accaaagcgt | cctctggagt aatctggaac | 660 |
| tccttcaagg | agttagagga | atctgaactt | gaaacggtca | tcagagaaat ccccgctccc | 720 |
| tcgttcttaa | ttccactacc | caagcacctt | actgcaagta | gcagttccct cctagatcat | 780 |
| gaccgaaccg | tgtttcagtg | gctggatcag | caaccccccgt | cgtcagttct atatgtaagc | 840 |
| tttgggagta | cttcggaagt | ggatgaaaag | gacttcttag | agattgcgcg agggctcgtg | 900 |
| gatagcaaac | agagcttcct | gtgggtagtg | agaccgggat | tcgttaaggg ctcgacgtgg | 960 |
| gtcgagccgt | tgccagatgg | ttttctaggg | gagagaggga | gaatcgtgaa atgggttcca | 1020 |
| cagcaagagg | ttttggctca | cggagctata | ggggccttttt | ggaccccactc tggttggaat | 1080 |
| tctactcttg | aaagtgtctg | tgaaggcgtt | ccaatgatat | tttctgattt tgggcttgac | 1140 |
| cagcctctaa | acgctcgcta | tatgtctgat | gtgttgaagg | ttggcgtgta cctggagaat | 1200 |
| ggttgggaaa | gggggggaaat | tgccaacgcc | atacgccggg | taatggtgga cgaggaaggt | 1260 |
| gagtacatac | gtcagaacgc | tcgggttttta | aaacaaaaag | cggacgtcag ccttatgaag | 1320 |
| ggaggtagct | cctatgaatc | cctagaatcc | ttggtaagct | atatatcttc gttataa | 1377 |

<210> SEQ ID NO 3
<211> LENGTH: 462
<212> TYPE: PRT
<213> ORGANISM: Artificial Sequence
<220> FEATURE:
<223> OTHER INFORMATION: Synthetic Polypeptide

<400> SEQUENCE: 3

Met Asp Ser Gly Tyr Ser Ser Tyr Ala Ala Ala Gly Met His
1               5                   10                  15

Val Val Ile Cys Pro Trp Leu Ala Phe Gly His Leu Leu Pro Cys Leu
            20                  25                  30

Asp Leu Ala Gln Arg Leu Ala Ser Arg Gly His Arg Val Ser Phe Val
        35                  40                  45

Ser Thr Pro Arg Asn Ile Ser Arg Leu Pro Pro Val Arg Pro Ala Leu
    50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Leu Glu His Lys Val Pro
    130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Ala Gly
                165                 170                 175

Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
        195                 200                 205

```
Ser Leu Thr Leu Ser Arg Ser Ser Leu Val Val Gly Arg Ser Cys Val
    210                 215                 220
Glu Phe Glu Pro Glu Thr Val Pro Leu Leu Ser Thr Leu Arg Gly Lys
225                 230                 235                 240
Pro Ile Thr Phe Leu Gly Leu Met Pro Pro Leu His Glu Gly Arg Arg
                245                 250                 255
Glu Asp Gly Glu Asp Ala Thr Val Arg Trp Leu Asp Ala Gln Pro Ala
            260                 265                 270
Lys Ser Val Val Tyr Val Ala Leu Gly Ser Glu Val Pro Leu Gly Val
        275                 280                 285
Glu Lys Val His Glu Leu Ala Leu Gly Leu Glu Leu Ala Gly Thr Arg
    290                 295                 300
Phe Leu Trp Ala Leu Arg Lys Pro Thr Gly Val Ser Asp Ala Asp Leu
305                 310                 315                 320
Leu Pro Ala Gly Phe Glu Glu Arg Thr Arg Gly Arg Gly Val Val Ala
                325                 330                 335
Thr Arg Trp Val Pro Gln Met Ser Ile Leu Ala His Ala Ala Val Gly
            340                 345                 350
Ala Phe Leu Thr His Cys Gly Trp Asn Ser Thr Ile Glu Gly Leu Met
        355                 360                 365
Phe Gly His Pro Leu Ile Met Leu Pro Ile Phe Gly Asp Gln Gly Pro
    370                 375                 380
Asn Ala Arg Leu Ile Glu Ala Lys Asn Ala Gly Leu Gln Val Ala Arg
385                 390                 395                 400
Asn Asp Gly Asp Gly Ser Phe Asp Arg Glu Gly Val Ala Ala Ala Ile
                405                 410                 415
Arg Ala Val Ala Val Glu Glu Glu Ser Ser Lys Val Phe Gln Ala Lys
            420                 425                 430
Ala Lys Lys Leu Gln Glu Ile Val Ala Asp Met Ala Cys His Glu Arg
        435                 440                 445
Tyr Ile Asp Gly Phe Ile Gln Gln Leu Arg Ser Tyr Lys Asp
    450                 455                 460

<210> SEQ ID NO 4
<211> LENGTH: 1389
<212> TYPE: DNA
<213> ORGANISM: Artificial Sequence
<220> FEATURE:
<223> OTHER INFORMATION: Synthetic Polynucleotide

<400> SEQUENCE: 4
atggattcgg gttactcttc ctcctatgcg gcggctgcgg gtatgcacgt tgttatctgt      60
ccgtggctgg cttttggtca cctgctgccg tgcctggatc tggcacagcg tctggcttca     120
cgcggccatc gtgtcagctt cgtgtctacc ccgcgcaata tttcgcgtct gccgccggtt     180
cgtccggcac tggctccgct ggttgcattt gtcgctctgc cgctgccgcg cgtggaaggt     240
ctgccggatg gtgcggaaag taccaacgac gtgccgcatg atcgcccgga catggttgaa     300
ctgcaccgtc gtgcattcga tggtctggca gcaccgtttt ccgaatttct gggtacggcg     360
tgcgccgatt gggtgatcgt tgacgtcttt catcactggg cggcggcggc ggcgctggaa     420
cataaagttc cgtgtgcaat gatgctgctg ggctcagctc acatgattgc gtcgatcgca     480
gaccgtcgcc tggaacgtgc agaaaccgaa agtccggctg cggccggcca gggtcgcccg     540
gcagctgcgc cgaccttcga agtggcccgc atgaaactga ttcgtacgaa aggcagctct     600
```

```
ggtatgagcc tggcagaacg ctttagtctg accctgtccc gtagttccct ggtggttggt    660
cgcagttgcg ttgaatttga accggaaacc gtcccgctgc tgtccacgct gcgtggtaaa    720
ccgatcacct ttctgggtct gatgccgccg ctgcatgaag ccgtcgcga agatggtgaa     780 gacgcaacgg tgcgttggct ggatgcacag ccggctaaaa gcgtcgtgta tgtcgccctg    840
ggctctgaag tgccgctggg tgtggaaaaa gttcacgaac tggcactggg cctggaactg    900
gctggcaccc gcttcctgtg gcactgcgt aaaccgacgg tgtgagcga tgcggacctg      960 ctgccggccg ttttgaaga acgtacccgc ggccgtggtg ttgtcgcaac gcgttgggtc    1020
ccgcaaatga gcattctggc gcatgccgca gtgggcgcct ttctgaccca ctgtggttgg   1080
aacagcacga tcgaaggcct gatgtttggt cacccgctga ttatgctgcc gatcttcggc   1140
gatcagggtc cgaacgcacg tctgattgaa gcgaaaaatg ccggcctgca gttgcgcgc    1200 aacgatggcg acggttcttt cgaccgtgag ggtgtggctg cggccattcg cgcagtggct   1260
gttgaagaag aatcatcgaa agttttcag gcgaaagcca aaaaactgca agaaatcgtc    1320
gcggatatgg cctgccacga acgctacatt gatggtttca ttcagcaact gcgctcctac   1380
aaagactaa                                                            1389
```

<210> SEQ ID NO 5
<211> LENGTH: 459
<212> TYPE: PRT
<213> ORGANISM: Artificial Sequence
<220> FEATURE:
<223> OTHER INFORMATION: Synthetic Polypeptide

<400> SEQUENCE: 5

```
Met Asp Gly Asn Ser Ser Ser Pro Leu His Val Val Ile Cys Pro
1               5                   10                  15

Trp Leu Ala Leu Gly His Leu Leu Pro Cys Leu Asp Ile Ala Glu Arg
            20                  25                  30

Leu Ala Ser Arg Gly His Arg Val Ser Phe Val Ser Thr Pro Arg Asn
        35                  40                  45

Ile Ala Arg Leu Pro Pro Leu Arg Pro Ala Val Ala Pro Leu Val Asp
    50                  55                  60

Phe Val Ala Leu Pro Leu Pro His Val Asp Gly Leu Pro Glu Gly Ala
65                  70                  75                  80

Glu Ser Thr Asn Asp Val Pro Tyr Asp Lys Phe Glu Leu His Arg Lys
                85                  90                  95

Ala Phe Asp Gly Leu Ala Ala Pro Phe Ser Glu Phe Leu Arg Ala Ala
            100                 105                 110

Cys Ala Glu Gly Ala Gly Ser Arg Pro Asp Trp Leu Ile Val Asp Thr
        115                 120                 125

Phe His His Trp Ala Ala Ala Ala Val Glu Asn Lys Val Pro Cys
    130                 135                 140

Val Met Leu Leu Leu Gly Ala Ala Thr Val Ile Ala Gly Phe Ala Arg
145                 150                 155                 160

Gly Val Ser Glu His Ala Ala Ala Val Gly Lys Glu Arg Pro Ala
                165                 170                 175

Ala Glu Ala Pro Ser Phe Glu Thr Glu Arg Arg Lys Leu Met Thr Thr
            180                 185                 190

Gln Asn Ala Ser Gly Met Thr Val Ala Glu Arg Tyr Phe Leu Thr Leu
        195                 200                 205

Met Arg Ser Asp Leu Val Ala Ile Arg Ser Cys Ala Glu Trp Glu Pro
    210                 215                 220
```

```
Glu Ser Val Ala Ala Leu Thr Thr Leu Ala Gly Lys Pro Val Val Pro
225                 230                 235                 240

Leu Gly Leu Leu Pro Pro Ser Pro Glu Gly Gly Arg Gly Val Ser Lys
            245                 250                 255

Glu Asp Ala Ala Val Arg Trp Leu Asp Ala Gln Pro Ala Lys Ser Val
        260                 265                 270

Val Tyr Val Ala Leu Gly Ser Glu Val Pro Leu Arg Ala Glu Gln Val
    275                 280                 285

His Glu Leu Ala Leu Gly Leu Glu Leu Ser Gly Ala Arg Phe Leu Trp
290                 295                 300

Ala Leu Arg Lys Pro Thr Asp Ala Pro Asp Ala Ala Val Leu Pro Pro
305                 310                 315                 320

Gly Phe Glu Glu Arg Thr Arg Gly Arg Gly Leu Val Val Thr Gly Trp
            325                 330                 335

Val Pro Gln Ile Gly Val Leu Ala His Gly Ala Val Ala Ala Phe Leu
        340                 345                 350

Thr His Cys Gly Trp Asn Ser Thr Ile Glu Gly Leu Leu Phe Gly His
    355                 360                 365

Pro Leu Ile Met Leu Pro Ile Ser Ser Asp Gln Gly Pro Asn Ala Arg
370                 375                 380

Leu Met Glu Gly Arg Lys Val Gly Met Gln Val Pro Arg Asp Glu Ser
385                 390                 395                 400

Asp Gly Ser Phe Arg Arg Glu Asp Val Ala Ala Thr Val Arg Ala Val
            405                 410                 415

Ala Val Glu Glu Asp Gly Arg Arg Val Phe Thr Ala Asn Ala Lys Lys
        420                 425                 430

Met Gln Glu Ile Val Ala Asp Gly Ala Cys His Glu Arg Cys Ile Asp
    435                 440                 445

Gly Phe Ile Gln Gln Leu Arg Ser Tyr Lys Ala
450                 455

<210> SEQ ID NO 6
<211> LENGTH: 1380
<212> TYPE: DNA
<213> ORGANISM: Artificial Sequence
<220> FEATURE:
<223> OTHER INFORMATION: Synthetic Polynucleotide

<400> SEQUENCE: 6
atggatggta actcctcctc ctcgccgctg catgtggtca tttgtccgtg gctggctctg      60
ggtcacctgc tgccgtgtct ggatattgct gaacgtctgg cgtcacgcgg ccatcgtgtc     120
agttttgtgt ccaccccgcg caacattgcc cgtctgccgc cgctgcgtcc ggctgttgca     180
ccgctggttg atttcgtcgc actgccgctg ccgcatgttg acggtctgcc ggagggtgcg     240
gaatcgacca atgatgtgcc gtatgacaaa tttgaactgc accgtaaggc gttcgatggt     300
ctggcggccc cgtttagcga atttctgcgt gcagcttgcg cagaaggtgc aggttctcgc     360
ccggattggc tgattgtgga cacctttcat cactgggcgg cggcggcggc ggtggaaaac     420
aaagtgccgt gtgttatgct gctgctgggt gcagcaacgg tgatcgctgg tttcgcgcgt     480
ggtgttagcg aacatgcggc ggcggcggtg gtaaagaac gtccggctgc ggaagccccg     540
agttttgaaa ccgaacgtcg caagctgatg accacgcaga atgcctccgg catgaccgtg     600
gcagaacgct atttcctgac gctgatgcgt agcgatctgg ttgccatccg ctcttgcgca     660
gaatgggaac cggaaagcgt ggcagcactg accacgctgg caggtaaacc ggtggttccg     720
```

```
ctgggtctgc tgccgccgag tccggaaggc ggtcgtggcg tttccaaaga agatgctgcg    780
gtccgttggc tggacgcaca gccggcaaag tcagtcgtgt acgtcgcact gggttcggaa    840
gtgccgctgc gtgcggaaca agttcacgaa ctggcactgg gcctggaact gagcggtgct    900
cgctttctgt gggcgctgcg taaaccgacc gatgcaccgg acgccgcagt gctgccgccg    960
ggtttcgaag aacgtacccg cggccgtggt ctggttgtca cgggttgggt gccgcagatt   1020
ggcgttctgg ctcatggtgc ggtggctgcg tttctgaccc actgtggctg aactctacg   1080 atcgaaggcc tgctgttcgg tcatccgctg attatgctgc cgatcagctc tgatcagggt   1140
ccgaatgcgc gcctgatgga aggccgtaaa gtcggtatgc aagtgccgcg tgatgaatca   1200
gacggctcgt tcgtcgcga agatgttgcc gcaaccgtcc gcgccgtggc agttgaagaa   1260
gacggtcgtc gcgtcttcac ggctaacgcg aaaaagatgc aagaaattgt ggccgatggc   1320
gcatgccacg aacgttgtat tgacggtttt atccagcaac tgcgcagtta caaggcgtga   1380
```

<210> SEQ ID NO 7
<211> LENGTH: 808
<212> TYPE: PRT
<213> ORGANISM: Artificial Sequence
<220> FEATURE:
<223> OTHER INFORMATION: Synthetic Polypeptide

<400> SEQUENCE: 7

```
Met Ala Asn Ala Glu Arg Met Ile Thr Arg Val His Ser Gln Arg Glu
1               5                   10                  15

Arg Leu Asn Glu Thr Leu Val Ser Glu Arg Asn Glu Val Leu Ala Leu
            20                  25                  30

Leu Ser Arg Val Glu Ala Lys Gly Lys Gly Ile Leu Gln Gln Asn Gln
        35                  40                  45

Ile Ile Ala Glu Phe Glu Ala Leu Pro Glu Gln Thr Arg Lys Lys Leu
    50                  55                  60

Glu Gly Gly Pro Phe Phe Asp Leu Leu Lys Ser Thr Gln Glu Ala Ile
65                  70                  75                  80

Val Leu Pro Pro Trp Val Ala Leu Ala Val Arg Pro Arg Pro Gly Val
                85                  90                  95

Trp Glu Tyr Leu Arg Val Asn Leu His Ala Leu Val Val Glu Glu Leu
            100                 105                 110

Gln Pro Ala Glu Phe Leu His Phe Lys Glu Glu Leu Val Asp Gly Val
        115                 120                 125

Lys Asn Gly Asn Phe Thr Leu Glu Leu Asp Phe Glu Pro Phe Asn Ala
    130                 135                 140

Ser Ile Pro Arg Pro Thr Leu His Lys Tyr Ile Gly Asn Gly Val Asp
145                 150                 155                 160

Phe Leu Asn Arg His Leu Ser Ala Lys Leu Phe His Asp Lys Glu Ser
                165                 170                 175

Leu Leu Pro Leu Leu Lys Phe Leu Arg Leu His Ser His Gln Gly Lys
            180                 185                 190

Asn Leu Met Leu Ser Glu Lys Ile Gln Asn Leu Asn Thr Leu Gln His
        195                 200                 205

Thr Leu Arg Lys Ala Glu Glu Tyr Leu Ala Glu Leu Lys Ser Glu Thr
    210                 215                 220

Leu Tyr Glu Glu Phe Glu Ala Lys Phe Glu Glu Ile Gly Leu Glu Arg
225                 230                 235                 240

Gly Trp Gly Asp Asn Ala Glu Arg Val Leu Asp Met Ile Arg Leu Leu
```

-continued

```
                245                 250                 255
Leu Asp Leu Leu Glu Ala Pro Asp Pro Cys Thr Leu Glu Thr Phe Leu
            260                 265                 270
Gly Arg Val Pro Met Val Phe Asn Val Val Ile Leu Ser Pro His Gly
            275                 280                 285
Tyr Phe Ala Gln Asp Asn Val Leu Gly Tyr Pro Asp Thr Gly Gly Gln
            290                 295                 300
Val Val Tyr Ile Leu Asp Gln Val Arg Ala Leu Glu Ile Glu Met Leu
305                 310                 315                 320
Gln Arg Ile Lys Gln Gln Gly Leu Asn Ile Lys Pro Arg Ile Leu Ile
            325                 330                 335
Leu Thr Arg Leu Leu Pro Asp Ala Val Gly Thr Thr Cys Gly Glu Arg
            340                 345                 350
Leu Glu Arg Val Tyr Asp Ser Glu Tyr Cys Asp Ile Leu Arg Val Pro
            355                 360                 365
Phe Arg Thr Glu Lys Gly Ile Val Arg Lys Trp Ile Ser Arg Phe Glu
            370                 375                 380
Val Trp Pro Tyr Leu Glu Thr Tyr Thr Glu Asp Ala Ala Val Glu Leu
385                 390                 395                 400
Ser Lys Glu Leu Asn Gly Lys Pro Asp Leu Ile Ile Gly Asn Tyr Ser
            405                 410                 415
Asp Gly Asn Leu Val Ala Ser Leu Leu Ala His Lys Leu Gly Val Thr
            420                 425                 430
Gln Cys Thr Ile Ala His Ala Leu Glu Lys Thr Lys Tyr Pro Asp Ser
            435                 440                 445
Asp Ile Tyr Trp Lys Lys Leu Asp Asp Lys Tyr His Phe Ser Cys Gln
            450                 455                 460
Phe Thr Ala Asp Ile Phe Ala Met Asn His Thr Asp Phe Ile Ile Thr
465                 470                 475                 480
Ser Thr Phe Gln Glu Ile Ala Gly Ser Lys Glu Thr Val Gly Gln Tyr
            485                 490                 495
Glu Ser His Thr Ala Phe Thr Leu Pro Gly Leu Tyr Arg Val Val His
            500                 505                 510
Gly Ile Asp Val Phe Asp Pro Lys Phe Asn Ile Val Ser Pro Gly Ala
            515                 520                 525
Asp Met Ser Ile Tyr Phe Pro Tyr Thr Glu Glu Lys Arg Arg Leu Thr
            530                 535                 540
Lys Phe His Ser Glu Ile Glu Glu Leu Leu Tyr Ser Asp Val Glu Asn
545                 550                 555                 560
Lys Glu His Leu Cys Val Leu Lys Asp Lys Lys Pro Ile Leu Phe
            565                 570                 575
Thr Met Ala Arg Leu Asp Arg Val Lys Asn Leu Ser Gly Leu Val Glu
            580                 585                 590
Trp Tyr Gly Lys Asn Thr Arg Leu Arg Glu Leu Ala Asn Leu Val Val
            595                 600                 605
Val Gly Gly Asp Arg Arg Lys Glu Ser Lys Asp Asn Glu Glu Lys Ala
            610                 615                 620
Glu Met Lys Lys Met Tyr Asp Leu Ile Glu Glu Tyr Lys Leu Asn Gly
625                 630                 635                 640
Gln Phe Arg Trp Ile Ser Ser Gln Met Asp Arg Val Arg Asn Gly Glu
            645                 650                 655
Leu Tyr Arg Tyr Ile Cys Asp Thr Lys Gly Ala Phe Val Gln Pro Ala
            660                 665                 670
```

```
Leu Tyr Glu Ala Phe Gly Leu Thr Val Val Glu Ala Met Thr Cys Gly
        675                 680                 685

Leu Pro Thr Phe Ala Thr Cys Lys Gly Gly Pro Ala Glu Ile Ile Val
    690                 695                 700

His Gly Lys Ser Gly Phe His Ile Asp Pro Tyr His Gly Asp Gln Ala
705                 710                 715                 720

Ala Asp Thr Leu Ala Asp Phe Phe Thr Lys Cys Lys Glu Asp Pro Ser
            725                 730                 735

His Trp Asp Glu Ile Ser Lys Gly Gly Leu Gln Arg Ile Glu Glu Lys
        740                 745                 750

Tyr Thr Trp Gln Ile Tyr Ser Gln Arg Leu Leu Thr Leu Thr Gly Val
    755                 760                 765

Tyr Gly Phe Trp Lys His Val Ser Asn Leu Asp Arg Leu Glu Ala Arg
770                 775                 780

Arg Tyr Leu Glu Met Phe Tyr Ala Leu Lys Tyr Arg Pro Leu Ala Gln
785                 790                 795                 800

Ala Val Pro Leu Ala Gln Asp Asp
            805

<210> SEQ ID NO 8
<211> LENGTH: 2427
<212> TYPE: DNA
<213> ORGANISM: Artificial Sequence
<220> FEATURE:
<223> OTHER INFORMATION: Synthetic Polynucleotide

<400> SEQUENCE: 8
atggcaaacg ctgaacgtat gataacgcgc gtccacagcc aacgtgagcg tttgaacgaa     60
acgcttgttt ctgagagaaa cgaagtcctt gccttgcttt ccagggttga agccaaaggt    120
aaaggtattt tacaacaaaa ccagatcatt gctgaattcg aagctttgcc tgaacaaacc    180
cggaagaaac ttgaaggtgg tccttcttt gaccttctca atccactca ggaagcaatt     240 gtgttgccac catgggttgc tctagctgtg aggccaaggc ctggtgtttg gaatactta    300 cgagtcaatc tccatgctct tgtcgttgaa gaactccaac tgctgagtt tcttcatttc    360 aaggaagaac tcgttgatgg agttaagaat ggtaatttca ctcttgagct tgatttcgag    420
ccattcaatg cgtctatccc tcgtccaaca ctccacaaat acattggaaa tggtgttgac    480
ttccttaacc gtcatttatc ggctaagctc ttccatgaca aggagagttt gcttccattg    540
cttaagttcc ttcgtcttca cagccaccag ggcaagaacc tgatgttgag cgagaagatt    600
cagaacctca cactctgca cacaccttg aggaaagcag aagagtatct agcagagctt     660
aagtccgaaa cactgtatga agagtttgag gccaagtttg aggagattgg tcttgagagg    720
ggatggggag acaatgcaga gcgtgtcctt gacatgatac gtcttctttt ggaccttctt    780
gaggcgcctg atccttgcac tcttgagact tttcttggaa gagtaccaat ggtgttcaac    840
gttgtgatcc tctctccaca tggttacttt gctcaggaca atgttcttgg ttaccctgac    900
actggtggac aggttgttta cattcttgat caagttcgtg ctctggagat agagatgctt    960
caacgtatta gcaacaagg actcaacatt aaaccaagga ttctcattct aactcgactt    1020
ctacctgatg cggtaggaac tacatgcggt gaacgtctcg agagagttta tgattctgag    1080
tactgtgata tccttcgtgt gcccttcaga acagagaagg gtattgttcg caaatggatc    1140
tcaaggttcg aagtctggcc atatctgag acttacaccg aggatgctgc ggttgagcta    1200
tcgaaagaat tgaatggcaa gcctgacctt atcattggta actacagtga tggaaatctt    1260
```

-continued

```
gttgcttctt tattggctca caaacttggt gtcactcagt gtaccattgc tcatgctctt    1320
gagaaaacaa agtacccgga ttctgatatc tactggaaga agcttgacga caagtaccat    1380
ttctcatgcc agttcactgc ggatattttc gcaatgaacc acactgattt catcatcact    1440
agtactttcc aagaaattgc tggaagcaaa gaaactgttg ggcagtatga agccacaca     1500 gcctttactc ttcccggatt gtatcgagtt gttcacggga ttgatgtgtt tgatcccaag    1560
ttcaacattg tctctcctgg tgctgatatg agcatctact cccttacac agaggagaag     1620 cgtagattga ctaagttcca ctctgagatc gaggagctcc tctacagcga tgttgagaac    1680
aaagagcact tatgtgtgct caaggacaag aagaagccga ttctcttcac aatggctagg    1740
cttgatcgtg tcaagaactt gtcaggtctt gttgagtggt acgggaagaa cacccgcttg    1800
cgtgagctag ctaacttggt tgttgttgga ggagacagga ggaaagagtc aaaggacaat    1860
gaagagaaag cagagatgaa gaaaatgtat gatctcattg aggaatacaa gctaaacggt    1920
cagttcaggt ggatctcctc tcagatggac cgggtaagga acggtgagct gtaccggtac    1980
atctgtgaca ccaagggtgc ttttgtccaa cctgcattat atgaagcctt tgggttaact    2040
gttgtggagg ctatgacttg tggtttaccg actttcgcca cttgcaaagg tggtccagct    2100
gagatcattg tgcacggtaa atcgggtttc cacattgacc cttaccatgg tgatcaggct    2160
gctgatactc ttgctgattt cttccaccaag tgtaaggagg atccatctca ctgggatgag    2220
atctcaaaag gagggcttca gaggattgag gagaaataca cttggcaaat ctattcacag    2280
aggctcttga cattgactgg tgtgtatgga ttctggaagc atgtctcgaa ccttgaccgt    2340
cttgaggctc gccgttacct tgaaatgttc tatgcattga agtatcgccc attggctcag    2400
gctgttcctc ttgcacaaga tgattga                                        2427
```

<210> SEQ ID NO 9
<211> LENGTH: 1268
<212> TYPE: PRT
<213> ORGANISM: Artificial Sequence
<220> FEATURE:
<223> OTHER INFORMATION: Synthetic Polypeptide
<400> SEQUENCE: 9

```
Met Glu Asn Lys Thr Glu Thr Thr Val Arg Arg Arg Arg Ile Ile
1               5                  10                  15

Leu Phe Pro Val Pro Phe Gln Gly His Ile Asn Pro Ile Leu Gln Leu
                20                  25                  30

Ala Asn Val Leu Tyr Ser Lys Gly Phe Ser Ile Thr Ile Phe His Thr
            35                  40                  45

Asn Phe Asn Lys Pro Lys Thr Ser Asn Tyr Pro His Phe Thr Phe Arg
        50                  55                  60

Phe Ile Leu Asp Asn Asp Pro Gln Asp Glu Arg Ile Ser Asn Leu Pro
65                  70                  75                  80

Thr His Gly Pro Leu Ala Gly Met Arg Ile Pro Ile Ile Asn Glu His
                85                  90                  95

Gly Ala Asp Glu Leu Arg Arg Glu Leu Glu Leu Leu Met Leu Ala Ser
                100                 105                 110

Glu Glu Asp Glu Glu Val Ser Cys Leu Ile Thr Asp Ala Leu Trp Tyr
            115                 120                 125

Phe Ala Gln Ser Val Ala Asp Ser Leu Asn Leu Arg Arg Leu Val Leu
        130                 135                 140

Met Thr Ser Ser Leu Phe Asn Phe His Ala His Val Ser Leu Pro Gln
```

-continued

```
                145                 150                 155                 160
            Phe Asp Glu Leu Gly Tyr Leu Asp Pro Asp Lys Thr Arg Leu Glu
                            165                 170                 175

Glu Gln Ala Ser Gly Phe Pro Met Leu Lys Val Lys Asp Ile Lys Ser
                        180                 185                 190

Ala Tyr Ser Asn Trp Gln Ile Leu Lys Glu Ile Leu Gly Lys Met Ile
                        195                 200                 205

Lys Gln Thr Lys Ala Ser Ser Gly Val Ile Trp Asn Ser Phe Lys Glu
                    210                 215                 220

Leu Glu Glu Ser Glu Leu Glu Thr Val Ile Arg Glu Ile Pro Ala Pro
            225                 230                 235                 240

Ser Phe Leu Ile Pro Leu Pro Lys His Leu Thr Ala Ser Ser Ser Ser
                                245                 250                 255

Leu Leu Asp His Asp Arg Thr Val Phe Gln Trp Leu Asp Gln Gln Pro
                            260                 265                 270

Pro Ser Ser Val Leu Tyr Val Ser Phe Gly Ser Thr Ser Glu Val Asp
                        275                 280                 285

Glu Lys Asp Phe Leu Glu Ile Ala Arg Gly Leu Val Asp Ser Lys Gln
                    290                 295                 300

Ser Phe Leu Trp Val Val Arg Pro Gly Phe Val Lys Gly Ser Thr Trp
            305                 310                 315                 320

Val Glu Pro Leu Pro Asp Gly Phe Leu Gly Glu Arg Gly Arg Ile Val
                                325                 330                 335

Lys Trp Val Pro Gln Gln Glu Val Leu Ala His Gly Ala Ile Gly Ala
                            340                 345                 350

Phe Trp Thr His Ser Gly Trp Asn Ser Thr Leu Glu Ser Val Cys Glu
                        355                 360                 365

Gly Val Pro Met Ile Phe Ser Asp Phe Gly Leu Asp Gln Pro Leu Asn
                    370                 375                 380

Ala Arg Tyr Met Ser Asp Val Leu Lys Val Gly Val Tyr Leu Glu Asn
            385                 390                 395                 400

Gly Trp Glu Arg Gly Glu Ile Ala Asn Ala Ile Arg Arg Val Met Val
                                405                 410                 415

Asp Glu Glu Gly Glu Tyr Ile Arg Gln Asn Ala Arg Val Leu Lys Gln
                            420                 425                 430

Lys Ala Asp Val Ser Leu Met Lys Gly Gly Ser Ser Tyr Glu Ser Leu
                        435                 440                 445

Glu Ser Leu Val Ser Tyr Ile Ser Ser Leu Gly Ser Gly Ala Asn Ala
                    450                 455                 460

Glu Arg Met Ile Thr Arg Val His Ser Gln Arg Glu Arg Leu Asn Glu
            465                 470                 475                 480

Thr Leu Val Ser Glu Arg Asn Glu Val Leu Ala Leu Leu Ser Arg Val
                                485                 490                 495

Glu Ala Lys Gly Lys Gly Ile Leu Gln Gln Asn Gln Ile Ile Ala Glu
                            500                 505                 510

Phe Glu Ala Leu Pro Glu Gln Thr Arg Lys Lys Leu Glu Gly Gly Pro
                        515                 520                 525

Phe Phe Asp Leu Leu Lys Ser Thr Gln Glu Ala Ile Val Leu Pro Pro
                    530                 535                 540

Trp Val Ala Leu Ala Val Arg Pro Arg Pro Gly Val Trp Glu Tyr Leu
            545                 550                 555                 560

Arg Val Asn Leu His Ala Leu Val Val Glu Glu Leu Gln Pro Ala Glu
                                565                 570                 575
```

Phe Leu His Phe Lys Glu Leu Val Asp Gly Val Lys Asn Gly Asn
            580                 585                 590

Phe Thr Leu Glu Leu Asp Phe Glu Pro Phe Asn Ala Ser Ile Pro Arg
        595                 600                 605

Pro Thr Leu His Lys Tyr Ile Gly Asn Gly Val Asp Phe Leu Asn Arg
    610                 615                 620

His Leu Ser Ala Lys Leu Phe His Asp Lys Glu Ser Leu Leu Pro Leu
625                 630                 635                 640

Leu Lys Phe Leu Arg Leu His Ser His Gln Gly Lys Asn Leu Met Leu
                645                 650                 655

Ser Glu Lys Ile Gln Asn Leu Asn Thr Leu Gln His Thr Leu Arg Lys
            660                 665                 670

Ala Glu Glu Tyr Leu Ala Glu Leu Lys Ser Glu Thr Leu Tyr Glu Glu
        675                 680                 685

Phe Glu Ala Lys Phe Glu Glu Ile Gly Leu Glu Arg Gly Trp Gly Asp
    690                 695                 700

Asn Ala Glu Arg Val Leu Asp Met Ile Arg Leu Leu Leu Asp Leu Leu
705                 710                 715                 720

Glu Ala Pro Asp Pro Cys Thr Leu Glu Thr Phe Leu Gly Arg Val Pro
                725                 730                 735

Met Val Phe Asn Val Val Ile Leu Ser Pro His Gly Tyr Phe Ala Gln
            740                 745                 750

Asp Asn Val Leu Gly Tyr Pro Asp Thr Gly Gly Gln Val Val Tyr Ile
        755                 760                 765

Leu Asp Gln Val Arg Ala Leu Glu Ile Glu Met Leu Gln Arg Ile Lys
    770                 775                 780

Gln Gln Gly Leu Asn Ile Lys Pro Arg Ile Leu Ile Leu Thr Arg Leu
785                 790                 795                 800

Leu Pro Asp Ala Val Gly Thr Thr Cys Gly Glu Arg Leu Glu Arg Val
                805                 810                 815

Tyr Asp Ser Glu Tyr Cys Asp Ile Leu Arg Val Pro Phe Arg Thr Glu
            820                 825                 830

Lys Gly Ile Val Arg Lys Trp Ile Ser Arg Phe Glu Val Trp Pro Tyr
        835                 840                 845

Leu Glu Thr Tyr Thr Glu Asp Ala Ala Val Glu Leu Ser Lys Glu Leu
    850                 855                 860

Asn Gly Lys Pro Asp Leu Ile Ile Gly Asn Tyr Ser Asp Gly Asn Leu
865                 870                 875                 880

Val Ala Ser Leu Leu Ala His Lys Leu Gly Val Thr Gln Cys Thr Ile
                885                 890                 895

Ala His Ala Leu Glu Lys Thr Lys Tyr Pro Asp Ser Asp Ile Tyr Trp
            900                 905                 910

Lys Lys Leu Asp Asp Lys Tyr His Phe Ser Cys Gln Phe Thr Ala Asp
        915                 920                 925

Ile Phe Ala Met Asn His Thr Asp Phe Ile Ile Thr Ser Thr Phe Gln
    930                 935                 940

Glu Ile Ala Gly Ser Lys Glu Thr Val Gly Gln Tyr Glu Ser His Thr
945                 950                 955                 960

Ala Phe Thr Leu Pro Gly Leu Tyr Arg Val Val His Gly Ile Asp Val
                965                 970                 975

Phe Asp Pro Lys Phe Asn Ile Val Ser Pro Gly Ala Asp Met Ser Ile
            980                 985                 990

| | | | | | | | | | | | | | |
|---|---|---|---|---|---|---|---|---|---|---|---|---|---|
|Tyr|Phe|Pro|Tyr|Thr|Glu|Glu|Lys|Arg|Arg|Leu|Thr|Lys|Phe|His|Ser|
| | |995| | | |1000| | | |1005| | | |

Tyr Phe Pro Tyr Thr Glu Glu Lys Arg Arg Leu Thr Lys Phe His Ser
              995                 1000                1005

Glu Ile Glu Glu Leu Leu Tyr Ser Asp Val Glu Asn Lys Glu His
    1010            1015             1020

Leu Cys Val Leu Lys Asp Lys Lys Pro Ile Leu Phe Thr Met
    1025            1030             1035

Ala Arg Leu Asp Arg Val Lys Asn Leu Ser Gly Leu Val Glu Trp
    1040            1045             1050

Tyr Gly Lys Asn Thr Arg Leu Arg Glu Leu Ala Asn Leu Val Val
    1055            1060             1065

Val Gly Gly Asp Arg Arg Lys Glu Ser Lys Asp Asn Glu Glu Lys
    1070            1075             1080

Ala Glu Met Lys Lys Met Tyr Asp Leu Ile Glu Glu Tyr Lys Leu
    1085            1090             1095

Asn Gly Gln Phe Arg Trp Ile Ser Ser Gln Met Asp Arg Val Arg
    1100            1105             1110

Asn Gly Glu Leu Tyr Arg Tyr Ile Cys Asp Thr Lys Gly Ala Phe
    1115            1120             1125

Val Gln Pro Ala Leu Tyr Glu Ala Phe Gly Leu Thr Val Val Glu
    1130            1135             1140

Ala Met Thr Cys Gly Leu Pro Thr Phe Ala Thr Cys Lys Gly Gly
    1145            1150             1155

Pro Ala Glu Ile Ile Val His Gly Lys Ser Gly Phe His Ile Asp
    1160            1165             1170

Pro Tyr His Gly Asp Gln Ala Ala Asp Thr Leu Ala Asp Phe Phe
    1175            1180             1185

Thr Lys Cys Lys Glu Asp Pro Ser His Trp Asp Glu Ile Ser Lys
    1190            1195             1200

Gly Gly Leu Gln Arg Ile Glu Glu Lys Tyr Thr Trp Gln Ile Tyr
    1205            1210             1215

Ser Gln Arg Leu Leu Thr Leu Thr Gly Val Tyr Gly Phe Trp Lys
    1220            1225             1230

His Val Ser Asn Leu Asp Arg Leu Glu Ala Arg Arg Tyr Leu Glu
    1235            1240             1245

Met Phe Tyr Ala Leu Lys Tyr Arg Pro Leu Ala Gln Ala Val Pro
    1250            1255             1260

Leu Ala Gln Asp Asp
    1265

<210> SEQ ID NO 10
<211> LENGTH: 3807
<212> TYPE: DNA
<213> ORGANISM: Artificial Sequence
<220> FEATURE:
<223> OTHER INFORMATION: Synthetic Polynucleotide

<400> SEQUENCE: 10
atggagaata agacagaaac aaccgtaaga cggaggcgga ggattatctt gttccctgta     60
ccatttcagg gccatattaa tccgatcctc caattagcaa acgtcctcta ctccaaggga    120
ttttcaataa caatcttcca tactaacttt aacaagccta aacgagtaa ttatcctcac     180 tttacattca ggttcattct agacaacgac cctcaggatg agcgtatctc aaatttacct    240
acgcatggcc ccttggcagg tatgcgaata ccaataatca atgagcatgg agccgatgaa    300
ctccgtcgcg agttagagct tctcatgctc gcaagtgagg aagacgagga agtttcgtgc    360

```
ctaataactg atgcgctttg gtacttcgcc caatcagtcg cagactcact gaatctacgc    420
cgtttggtcc ttatgacaag ttcattattc aactttcacg cacatgtatc actgccgcaa    480
tttgacgagt tgggttacct ggacccggat gacaaaacgc gattggagga acaagcgtcg    540
ggcttcccca tgctgaaagt caaagatatt aagagcgctt atagtaattg gcaaattctg    600
aaagaaattc tcggaaaaat gataaagcaa accaaagcgt cctctggagt aatctggaac    660
tccttcaagg agttagagga atctgaactt gaaacggtca tcagagaaat ccccgctccc    720
tcgttcttaa ttccactacc caagcacctt actgcaagta gcagttccct cctagatcat    780
gaccgaaccg tgtttcagtg gctggatcag caaccccgt cgtcagttct atatgtaagc    840
tttgggagta cttcggaagt ggatgaaaag gacttcttag agattgcgcg agggctcgtg    900
gatagcaaac agagcttcct gtgggtagtg agaccgggat tcgttaaggg ctcgacgtgg    960
gtcgagccgt tgccagatgg ttttctaggg gagagaggga gaatcgtgaa atgggttcca   1020
cagcaagagg ttttggctca cggagctata ggggcctttt ggacccactc tggttggaat   1080
tctactcttg aaagtgtctg tgaaggcgtt ccaatgatat tttctgattt tgggcttgac   1140
cagcctctaa acgctcgcta tatgtctgat gtgttgaagg ttggcgtgta cctggagaat   1200
ggttgggaaa ggggggaaat tgccaacgcc atacgccggg taatggtgga cgaggaaggt   1260
gagtacatac gtcagaacgc tcgggtttta aaacaaaaag cggacgtcag ccttatgaag   1320
ggaggtagct cctatgaatc cctagaatcc ttggtaagct atatatcttc gttaggttct   1380
ggtgcaaacg ctgaacgtat gataacgcgc gtccacagcc aacgtgagcg tttgaacgaa   1440
acgcttgttt ctgagagaaa cgaagtcctt gccttgcttt ccagggttga agccaaaggt   1500
aaaggtattt tacaacaaaa ccagatcatt gctgaattcg aagctttgcc tgaacaaacc   1560
cggaagaaac ttgaaggtgg tcctttcttt gaccttctca aatccactca ggaagcaatt   1620
gtgttgccac catgggttgc tctagctgtg aggccaaggc ctggtgtttg gaatacttac   1680
cgagtcaatc tccatgctct tgtcgttgaa gaactccaac ctgctgagtt tcttcatttc   1740
aaggaagaac tcgttgatgg agttaagaat ggtaatttca ctcttgagct tgatttcgag   1800
ccattcaatg cgtctatccc tcgtccaaca ctccacaaat acattggaaa tggtgttgac   1860
ttccttaacc gtcatttatc ggctaagctc ttccatgaca aggagagttt gcttccattg   1920
cttaagttcc ttcgtcttca cagccaccag ggcaagaacc tgatgttgag cgagaagatt   1980
cagaacctca cactctgca acacaccttg aggaaagcag aagagtatct agcagagctt   2040
aagtccgaaa cactgtatga agagtttgag gccaagtttg aggagattgg tcttgagagg   2100
ggatggggag acaatgcaga gcgtgtcctt gacatgatac gtcttctttt ggaccttctt   2160
gaggcgcctg atccttgcac tcttgagact tttcttggaa gagtaccaat ggtgttcaac   2220
gttgtgatcc tctctccaca tggttacttt gctcaggaca atgttcttgg ttaccctgac   2280
actggtggac aggttgttta cattcttgat caagttcgtg ctctggagat agagatgctt   2340
caacgtatta agcaacaagg actcaacatt aaaccaagga ttctcattct aactcgactt   2400
ctacctgatg cggtaggaac tacatgcggt gaacgtctcg agagagttta tgattctgag   2460
tactgtgata ttcttcgtgt gcccttcaga acagagaagg gtattgttcg caaatggatc   2520
tcaaggttcg aagtctggcc atatctagag acttacaccg aggatgctgc ggttgagcta   2580
tcgaaagaat tgaatggcaa gcctgacctt atcattggta actacagtga tggaaatctt   2640
gttgcttctt tattggctca caaacttggt gtcactcagt gtaccattgc tcatgctctt   2700
gagaaaacaa agtacccgga ttctgatatc tactggaaga agcttgacga caagtaccat   2760
```

-continued

```
ttctcatgcc agttcactgc ggatattttc gcaatgaacc acactgattt catcatcact   2820
agtactttcc aagaaattgc tggaagcaaa gaaactgttg ggcagtatga aagccacaca   2880
gcctttactc ttcccggatt gtatcgagtt gttcacggga ttgatgtgtt tgatcccaag   2940
ttcaacattg tctctcctgg tgctgatatg agcatctact tcccttacac agaggagaag   3000
cgtagattga ctaagttcca ctctgagatc gaggagctcc tctacagcga tgttgagaac   3060
aaagagcact tatgtgtgct caaggacaag aagaagccga ttctcttcac aatggctagg   3120
cttgatcgtg tcaagaactt gtcaggtctt gttgagtggt acgggaagaa cacccgcttg   3180
cgtgagctag ctaacttggt tgttgttgga ggagacagga ggaaagagtc aaaggacaat   3240
gaagagaaag cagagatgaa gaaaatgtat gatctcattg aggaatacaa gctaaacggt   3300
cagttcaggt ggatctcctc tcagatggac cgggtaagga acggtgagct gtaccggtac   3360
atctgtgaca ccaagggtgc ttttgtccaa cctgcattat atgaagcctt tgggttaact   3420
gttgtggagg ctatgacttg tggtttaccg actttcgcca cttgcaaagg tggtccagct   3480
gagatcattg tgcacggtaa atcgggtttc cacattgacc cttaccatgg tgatcaggct   3540
gctgatactc ttgctgattt cttcaccaag tgtaaggagg atccatctca ctgggatgag   3600
atctcaaaag gagggcttca gaggattgag gagaaataca cttggcaaat ctattcacag   3660
aggctcttga cattgactgg tgtgtatgga ttctggaagc atgtctcgaa ccttgaccgt   3720
cttgaggctc gccgttacct tgaaatgttc tatgcattga agtatcgccc attggctcag   3780
gctgttcctc ttgcacaaga tgattga                                       3807
```

<210> SEQ ID NO 11
<211> LENGTH: 1272
<212> TYPE: PRT
<213> ORGANISM: Artificial Sequence
<220> FEATURE:
<223> OTHER INFORMATION: Synthetic Polypeptide

<400> SEQUENCE: 11

```
Met Asp Ser Gly Tyr Ser Ser Tyr Ala Ala Ala Gly Met His
1               5                   10                  15

Val Val Ile Cys Pro Trp Leu Ala Phe Gly His Leu Pro Cys Leu
                20                  25                  30

Asp Leu Ala Gln Arg Leu Ala Ser Arg Gly His Arg Val Ser Phe Val
            35                  40                  45

Ser Thr Pro Arg Asn Ile Ser Arg Leu Pro Pro Val Arg Pro Ala Leu
        50                  55                  60

Ala Pro Leu Val Ala Phe Val Ala Leu Pro Leu Pro Arg Val Glu Gly
65                  70                  75                  80

Leu Pro Asp Gly Ala Glu Ser Thr Asn Asp Val Pro His Asp Arg Pro
                85                  90                  95

Asp Met Val Glu Leu His Arg Arg Ala Phe Asp Gly Leu Ala Ala Pro
            100                 105                 110

Phe Ser Glu Phe Leu Gly Thr Ala Cys Ala Asp Trp Val Ile Val Asp
        115                 120                 125

Val Phe His His Trp Ala Ala Ala Ala Leu Glu His Lys Val Pro
    130                 135                 140

Cys Ala Met Met Leu Leu Gly Ser Ala His Met Ile Ala Ser Ile Ala
145                 150                 155                 160

Asp Arg Arg Leu Glu Arg Ala Glu Thr Glu Ser Pro Ala Ala Ala Gly
                165                 170                 175
```

```
Gln Gly Arg Pro Ala Ala Ala Pro Thr Phe Glu Val Ala Arg Met Lys
            180                 185                 190

Leu Ile Arg Thr Lys Gly Ser Ser Gly Met Ser Leu Ala Glu Arg Phe
        195                 200                 205

Ser Leu Thr Leu Ser Arg Ser Ser Leu Val Val Gly Arg Ser Cys Val
    210                 215                 220

Glu Phe Glu Pro Glu Thr Val Pro Leu Leu Ser Thr Leu Arg Gly Lys
225                 230                 235                 240

Pro Ile Thr Phe Leu Gly Leu Met Pro Pro Leu His Glu Gly Arg Arg
                245                 250                 255

Glu Asp Gly Glu Asp Ala Thr Val Arg Trp Leu Asp Ala Gln Pro Ala
            260                 265                 270

Lys Ser Val Val Tyr Val Ala Leu Gly Ser Glu Val Pro Leu Gly Val
        275                 280                 285

Glu Lys Val His Glu Leu Ala Leu Gly Leu Glu Leu Ala Gly Thr Arg
    290                 295                 300

Phe Leu Trp Ala Leu Arg Lys Pro Thr Gly Val Ser Asp Ala Asp Leu
305                 310                 315                 320

Leu Pro Ala Gly Phe Glu Glu Arg Thr Arg Gly Arg Gly Val Val Ala
                325                 330                 335

Thr Arg Trp Val Pro Gln Met Ser Ile Leu Ala His Ala Ala Val Gly
            340                 345                 350

Ala Phe Leu Thr His Cys Gly Trp Asn Ser Thr Ile Glu Gly Leu Met
        355                 360                 365

Phe Gly His Pro Leu Ile Met Leu Pro Ile Phe Gly Asp Gln Gly Pro
370                 375                 380

Asn Ala Arg Leu Ile Glu Ala Lys Asn Ala Gly Leu Gln Val Ala Arg
385                 390                 395                 400

Asn Asp Gly Asp Gly Ser Phe Asp Arg Glu Gly Val Ala Ala Ala Ile
                405                 410                 415

Arg Ala Val Ala Val Glu Glu Glu Ser Ser Lys Val Phe Gln Ala Lys
            420                 425                 430

Ala Lys Lys Leu Gln Glu Ile Val Ala Asp Met Ala Cys His Glu Arg
        435                 440                 445

Tyr Ile Asp Gly Phe Ile Gln Gln Leu Arg Ser Tyr Lys Asp Gly Ser
    450                 455                 460

Gly Ala Asn Ala Glu Arg Met Ile Thr Arg Val His Ser Gln Arg Glu
465                 470                 475                 480

Arg Leu Asn Glu Thr Leu Val Ser Glu Arg Asn Glu Val Leu Ala Leu
                485                 490                 495

Leu Ser Arg Val Glu Ala Lys Gly Lys Gly Ile Leu Gln Gln Asn Gln
            500                 505                 510

Ile Ile Ala Glu Phe Glu Ala Leu Pro Glu Gln Thr Arg Lys Lys Leu
        515                 520                 525

Glu Gly Gly Pro Phe Phe Asp Leu Leu Lys Ser Thr Gln Glu Ala Ile
    530                 535                 540

Val Leu Pro Pro Trp Val Ala Leu Ala Val Arg Pro Arg Pro Gly Val
545                 550                 555                 560

Trp Glu Tyr Leu Arg Val Asn Leu His Ala Leu Val Val Glu Glu Leu
                565                 570                 575

Gln Pro Ala Glu Phe Leu His Phe Lys Glu Glu Leu Val Asp Gly Val
            580                 585                 590
```

```
Lys Asn Gly Asn Phe Thr Leu Glu Leu Asp Phe Glu Pro Phe Asn Ala
            595                 600                 605

Ser Ile Pro Arg Pro Thr Leu His Lys Tyr Ile Gly Asn Gly Val Asp
610                 615                 620

Phe Leu Asn Arg His Leu Ser Ala Lys Leu Phe His Asp Lys Glu Ser
625                 630                 635                 640

Leu Leu Pro Leu Leu Lys Phe Leu Arg Leu His Ser His Gln Gly Lys
                645                 650                 655

Asn Leu Met Leu Ser Glu Lys Ile Gln Asn Leu Asn Thr Leu Gln His
            660                 665                 670

Thr Leu Arg Lys Ala Glu Glu Tyr Leu Ala Glu Leu Lys Ser Glu Thr
        675                 680                 685

Leu Tyr Glu Glu Phe Glu Ala Lys Phe Glu Glu Ile Gly Leu Glu Arg
    690                 695                 700

Gly Trp Gly Asp Asn Ala Glu Arg Val Leu Asp Met Ile Arg Leu Leu
705                 710                 715                 720

Leu Asp Leu Leu Glu Ala Pro Asp Pro Cys Thr Leu Glu Thr Phe Leu
                725                 730                 735

Gly Arg Val Pro Met Val Phe Asn Val Ile Leu Ser Pro His Gly
            740                 745                 750

Tyr Phe Ala Gln Asp Asn Val Leu Gly Tyr Pro Asp Thr Gly Gly Gln
        755                 760                 765

Val Val Tyr Ile Leu Asp Gln Val Arg Ala Leu Glu Ile Glu Met Leu
    770                 775                 780

Gln Arg Ile Lys Gln Gln Gly Leu Asn Ile Lys Pro Arg Ile Leu Ile
785                 790                 795                 800

Leu Thr Arg Leu Leu Pro Asp Ala Val Gly Thr Thr Cys Gly Glu Arg
                805                 810                 815

Leu Glu Arg Val Tyr Asp Ser Glu Tyr Cys Asp Ile Leu Arg Val Pro
            820                 825                 830

Phe Arg Thr Glu Lys Gly Ile Val Arg Lys Trp Ile Ser Arg Phe Glu
        835                 840                 845

Val Trp Pro Tyr Leu Glu Thr Tyr Thr Glu Asp Ala Ala Val Glu Leu
    850                 855                 860

Ser Lys Glu Leu Asn Gly Lys Pro Asp Leu Ile Ile Gly Asn Tyr Ser
865                 870                 875                 880

Asp Gly Asn Leu Val Ala Ser Leu Leu Ala His Lys Leu Gly Val Thr
                885                 890                 895

Gln Cys Thr Ile Ala His Ala Leu Glu Lys Thr Lys Tyr Pro Asp Ser
            900                 905                 910

Asp Ile Tyr Trp Lys Lys Leu Asp Asp Lys Tyr His Phe Ser Cys Gln
        915                 920                 925

Phe Thr Ala Asp Ile Phe Ala Met Asn His Thr Asp Phe Ile Ile Thr
    930                 935                 940

Ser Thr Phe Gln Glu Ile Ala Gly Ser Lys Glu Thr Val Gly Gln Tyr
945                 950                 955                 960

Glu Ser His Thr Ala Phe Thr Leu Pro Gly Leu Tyr Arg Val Val His
                965                 970                 975

Gly Ile Asp Val Phe Asp Pro Lys Phe Asn Ile Val Ser Pro Gly Ala
            980                 985                 990

Asp Met Ser Ile Tyr Phe Pro Tyr  Thr Glu Glu Lys Arg Arg Leu Thr
        995                 1000                1005

Lys Phe His Ser Glu Ile Glu  Glu Leu Leu Tyr Ser Asp Val Glu
```

| | | | | | | | | | | |
|---|---|---|---|---|---|---|---|---|---|---|
| | | | 1010 | | | 1015 | | | 1020 | |
| Asn | Lys | Glu | His | Leu | Cys | Val | Leu | Lys | Asp | Lys |
| | | 1025 | | | | 1030 | | | | 1035 |
| Lys | Pro | Ile | | | | | | | | |
| Leu | Phe | Thr | Met | Ala | Arg | Leu | Asp | Arg | Val | Lys |
| | 1040 | | | | | 1045 | | | | 1050 |
| Asn | Leu | Ser | Gly | | | | | | | |
| Leu | Val | Glu | Trp | Tyr | Gly | Lys | Asn | Thr | Arg | Leu |
| | 1055 | | | | | 1060 | | | | 1065 |
| Arg | Glu | Leu | Ala | | | | | | | |
| Asn | Leu | Val | Val | Val | Gly | Gly | Asp | Arg | Arg | Lys |
| | 1070 | | | | | 1075 | | | | 1080 |
| Glu | Ser | Lys | Asp | | | | | | | |
| Asn | Glu | Glu | Lys | Ala | Glu | Met | Lys | Lys | Met | Tyr |
| | 1085 | | | | | 1090 | | | | 1095 |
| Asp | Leu | Ile | Glu | | | | | | | |
| Glu | Tyr | Lys | Leu | Asn | Gly | Gln | Phe | Arg | Trp | Ile |
| | 1100 | | | | | 1105 | | | | 1110 |
| Ser | Ser | Gln | Met | | | | | | | |
| Asp | Arg | Val | Arg | Asn | Gly | Glu | Leu | Tyr | Arg | Tyr |
| | 1115 | | | | | 1120 | | | | 1125 |
| Ile | Cys | Asp | Thr | | | | | | | |
| Lys | Gly | Ala | Phe | Val | Gln | Pro | Ala | Leu | Tyr | Glu |
| | 1130 | | | | | 1135 | | | | 1140 |
| Ala | Phe | Gly | Leu | | | | | | | |
| Thr | Val | Val | Glu | Ala | Met | Thr | Cys | Gly | Leu | Pro |
| | 1145 | | | | | 1150 | | | | 1155 |
| Thr | Phe | Ala | Thr | | | | | | | |
| Cys | Lys | Gly | Gly | Pro | Ala | Glu | Ile | Ile | Val | His |
| | 1160 | | | | | 1165 | | | | 1170 |
| Gly | Lys | Ser | Gly | | | | | | | |
| Phe | His | Ile | Asp | Pro | Tyr | His | Gly | Asp | Gln | Ala |
| | 1175 | | | | | 1180 | | | | 1185 |
| Ala | Asp | Thr | Leu | | | | | | | |
| Ala | Asp | Phe | Phe | Thr | Lys | Cys | Lys | Glu | Asp | Pro |
| | 1190 | | | | | 1195 | | | | 1200 |
| Ser | His | Trp | Asp | | | | | | | |
| Glu | Ile | Ser | Lys | Gly | Gly | Leu | Gln | Arg | Ile | Glu |
| | 1205 | | | | | 1210 | | | | 1215 |
| Glu | Lys | Tyr | Thr | | | | | | | |
| Trp | Gln | Ile | Tyr | Ser | Gln | Arg | Leu | Leu | Thr | Leu |
| | 1220 | | | | | 1225 | | | | 1230 |
| Thr | Gly | Val | Tyr | | | | | | | |
| Gly | Phe | Trp | Lys | His | Val | Ser | Asn | Leu | Asp | Arg |
| | 1235 | | | | | 1240 | | | | 1245 |
| Leu | Glu | Ala | Arg | | | | | | | |
| Arg | Tyr | Leu | Glu | Met | Phe | Tyr | Ala | Leu | Lys | Tyr |
| | 1250 | | | | | 1255 | | | | 1260 |
| Arg | Pro | Leu | Ala | | | | | | | |
| Gln | Ala | Val | Pro | Leu | Ala | Gln | Asp | Asp | | |
| | 1265 | | | | | 1270 | | | | |

<210> SEQ ID NO 12
<211> LENGTH: 3819
<212> TYPE: DNA
<213> ORGANISM: Artificial Sequence
<220> FEATURE:
<223> OTHER INFORMATION: Synthetic Polynucleotide

<400> SEQUENCE: 12

| | |
|---|---|
| atggattcgg gttactcttc ctcctatgcg gcggctgcgg gtatgcacgt tgttatctgt | 60 |
| ccgtggctgg cttttggtca cctgctgccg tgcctggatc tggcacagcg tctggcttca | 120 |
| cgcggccatc gtgtcagctt cgtgtctacc ccgcgcaata tttcgcgtct gccgccggtt | 180 |
| cgtccggcac tggctccgct ggttgcattt gtcgctctgc cgctgccgcg cgtggaaggt | 240 |
| ctgccggatg gtgcggaaag taccaacgac gtgccgcatg atcgcccgga catggttgaa | 300 |
| ctgcaccgtc gtgcattcga tggtctggca gcaccgtttt ccgaatttct gggtacggcg | 360 |
| tgcgccgatt gggtgatcgt tgacgtcttt catcactggg cggcggcggc ggcgctggaa | 420 |
| cataaagttc cgtgtgcaat gatgctgctg ggctcagctc acatgattgc gtcgatcgca | 480 |

-continued

```
gaccgtcgcc tggaacgtgc agaaaccgaa agtccggctg cggccggcca gggtcgcccg    540
gcagctgcgc cgaccttcga agtggcccgc atgaaactga ttcgtacgaa aggcagctct    600
ggtatgagcc tggcagaacg ctttagtctg accctgtccc gtagttccct ggtggttggt    660
cgcagttgcg ttgaatttga accggaaacc gtcccgctgc tgtccacgct gcgtggtaaa    720
ccgatcacct ttctgggtct gatgccgccg ctgcatgaag gccgtcgcga agatggtgaa    780
gacgcaacgg tgcgttggct ggatgcacag ccggctaaaa gcgtcgtgta tgtcgccctg    840
ggctctgaag tgccgctggg tgtggaaaaa gttcacgaac tggcactggg cctggaactg    900
gctggcaccc gcttcctgtg gcactgcgt aaaccgacgg tgtgagcga tgcggacctg    960
ctgccggccg ttttgaaga acgtacccgc ggccgtggtg ttgtcgcaac gcgttgggtc   1020
ccgcaaatga gcattctggc gcatgccgca gtgggcgcct ttctgaccca ctgtggttgg   1080
aacagcacga tcgaaggcct gatgtttggt cacccgctga ttatgctgcc gatcttcggc   1140
gatcagggtc cgaacgcacg tctgattgaa gcgaaaaatg ccggcctgca agttgcgcgc   1200
aacgatggcg acggttcttt cgaccgtgag ggtgtggctg cggccattcg cgcagtggct   1260
gttgaagaag aatcatcgaa agtttttcag gcgaaagcca aaaaactgca agaaatcgtc   1320
gcggatatgg cctgccacga acgctacatt gatggtttca ttcagcaact gcgctcctac   1380
aaagacggtt ctggtgcaaa cgctgaacgt atgataacgc gcgtccacag ccaacgtgag   1440
cgtttgaacg aaaacgcttgt ttctgagaga acgaagtcc ttgccttgct ttccagggtt   1500
gaagccaaag gtaaaggtat tttacaacaa accagatca ttgctgaatt cgaagctttg   1560
cctgaacaaa cccggaagaa acttgaaggt ggtcctttct tgaccttct caaatccact   1620
caggaagcaa ttgtgttgcc accatgggtt gctctagctg tgaggccaag gcctggtgtt   1680
tgggaatact tacgagtcaa tctccatgct cttgtcgttg aagaactcca acctgctgag   1740
tttcttcatt tcaaggaaga actcgttgat ggagttaaga atggtaattt cactcttgag   1800
cttgatttcg agccattcaa tgcgtctatc cctcgtccaa cactccacaa atacattgga   1860
aatggtgttg acttccttaa ccgtcattta tcggctaagc tcttccatga caaggagagt   1920
ttgcttccat tgcttaagtt ccttcgtctt cacagccacc agggcaagaa cctgatgttg   1980
agcgagaaga ttcagaacct caacactctg caacacacct gaggaaagc agaagagtat   2040
ctagcagagc ttaagtccga aacactgtat gaagagtttg aggccaagtt tgaggagatt   2100
ggtcttgaga ggggatgggg agacaatgca gagcgtgtcc ttgacatgat acgtcttctt   2160
ttggaccttc ttgaggcgcc tgatccttgc actcttgaga cttttcttgg aagagtacca   2220
atggtgttca acgttgtgat cctctctcca catggttact ttgctcagga caatgttctt   2280
ggttaccctg acactggtgg acaggttgtt tacattcttg atcaagttcg tgctctggag   2340
atagagatgc ttcaacgtat taagcaacaa ggactcaaca ttaaaccaag gattctcatt   2400
ctaactcgac ttctacctga tgcggtagga actacatgcg gtgaacgtct cgagagagtt   2460
tatgattctg agtactgtga tattcttcgt gtgcccttca gaacagagaa gggtattgtt   2520
cgcaaatgga tctcaaggtt cgaagtctgg ccatatctag agacttacac cgaggatgct   2580
gcggttgagc tatcgaaaga attgaatggc aagcctgacc ttatcattgg taactacagt   2640
gatggaaatc ttgttgcttc tttattggct cacaaacttg gtgtcactca gtgtaccatt   2700
gctcatgctc ttgagaaaac aaagtacccg gattctgata tctactggaa gaagcttgac   2760
gacaagtacc atttctcatg ccagttcact gcggatattt tcgcaatgaa ccacactgat   2820
ttcatcatca ctagtacttt ccaagaaatt gctggaagca agaaaactgt tgggcagtat   2880
```

```
gaaagccaca cagcctttac tcttcccgga ttgtatcgag ttgttcacgg gattgatgtg    2940
tttgatccca agttcaacat tgtctctcct ggtgctgata tgagcatcta cttcccttac    3000
acagaggaga agcgtagatt gactaagttc cactctgaga tcgaggagct cctctacagc    3060
gatgttgaga acaaagagca cttatgtgtg ctcaaggaca agaagaagcc gattctcttc    3120
acaatggcta ggcttgatcg tgtcaagaac ttgtcaggtc ttgttgagtg gtacgggaag    3180
aacacccgct tgcgtgagct agctaacttg gttgttgttg gaggagacag gaggaaagag    3240
tcaaaggaca atgaagagaa agcagagatg aagaaaatgt atgatctcat tgaggaatac    3300
aagctaaacg gtcagttcag gtggatctcc tctcagatgg accgggtaag gaacggtgag    3360
ctgtaccggt acatctgtga caccaagggt gcttttgtcc aacctgcatt atatgaagcc    3420
tttgggttaa ctgttgtgga ggctatgact tgtggtttac cgactttcgc cacttgcaaa    3480
ggtggtccag ctgagatcat tgtgcacggt aaatcgggtt tccacattga cccttaccat    3540
ggtgatcagg ctgctgatac tcttgctgat ttcttcacca agtgtaagga ggatccatct    3600
cactgggatg agatctcaaa aggagggctt cagaggattg aggagaaata cacttggcaa    3660
atctattcac agaggctctt gacattgact ggtgtgtatg gattctggaa gcatgtctcg    3720
aaccttgacc gtcttgaggc tcgccgttac cttgaaatgt tctatgcatt gaagtatcgc    3780
ccattggctc aggctgttcc tcttgcacaa gatgattga                          3819
```

NON-CALORIC SWEETENERS AND METHODS FOR SYNTHESIZING

CROSS-REFERENCE TO RELATED APPLICATIONS

This application claims priority to U.S. Provisional Patent Application No. 62/059,498, filed Oct. 3, 2014, entitled "NON-CALORIC SWEETENERS AND METHODS FOR SYNTHESIZING," and to U.S. Provisional Patent Application No. 62/098,929, filed Dec. 31, 2014, entitled "NON-CALORIC SWEETENERS AND METHODS FOR SYNTHESIZING," the disclosures of which are hereby incorporated by reference in their entirety.

STATEMENT IN SUPPORT FOR FILING A SEQUENCE LISTING

A paper copy of the Sequence Listing and a computer readable form of the Sequence Listing containing the file named "19452382_1.txt", which is 60,601 bytes in size (as measured in MICROSOFT WINDOWS® EXPLORER), are provided herein and are herein incorporated by reference. This Sequence Listing consists of SEQ ID NOs:1-12.

BACKGROUND OF THE DISCLOSURE

The present disclosure relates generally to natural sweeteners. More particularly, the present disclosure relates to a non-caloric sweetener and methods for synthesizing the non-caloric sweetener.

Steviol glycosides are natural products isolated from *Stevia rebaudiana* leaves. Steviol glycosides are widely used as high intensity, low-calorie sweeteners and are significantly sweeter than sucrose. As natural sweeteners, different steviol glucosides have different degrees of sweetness and after-taste. The sweetness of steviol glycosides is significantly higher than that of sucrose. For example, stevioside is 100-150 times sweeter than sucrose with bitter after-taste. Rebaudioside C is between 40-60 times sweeter than sucrose. Dulcoside A is about 30 times sweeter than sucrose.

Naturally occurring steviol glycosides share the same basic steviol structure, but differ in the content of carbohydrate residues (e.g., glucose, rhamnose and xylose residues) at the C13 and C19 positions. Steviol glycosides with known structures include, steviol, stevioside, rebaudioside A, rebaudioside B, rebaudioside C, rebaudioside D, rebaudioside E, rebaudioside F and dulcoside A (see e.g., Table 1). Other steviol glycosides are rebaudioside M, rebaudioside N and rebaudioside 0.

TABLE 1

| Steviol glycosides. | | | |
|---|---|---|---|
| Name | Structure | Molecular Formula | Molecular Weight |
| Steviol | 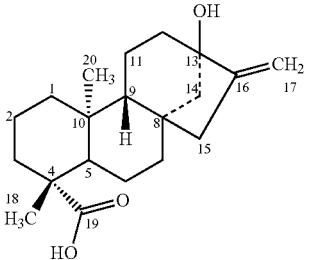 | $C_{20}H_{30}O_3$ | 318 |
| Stevioside | 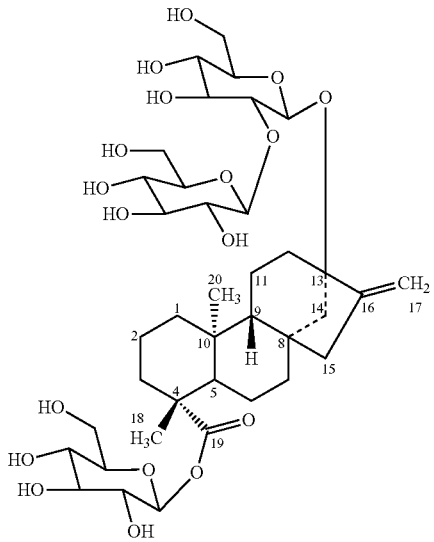 | $C_{38}H_{60}O_{18}$ | 804 |

TABLE 1-continued
Steviol glycosides.
| Name | Structure | Molecular Formula | Molecular Weight |
|---|---|---|---|
| Rebaudioside A | 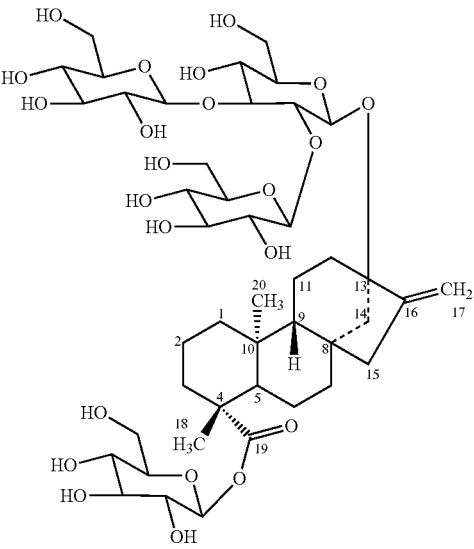 | $C_{44}H_{70}O_{23}$ | 966 |
| Rebaudioside-B | 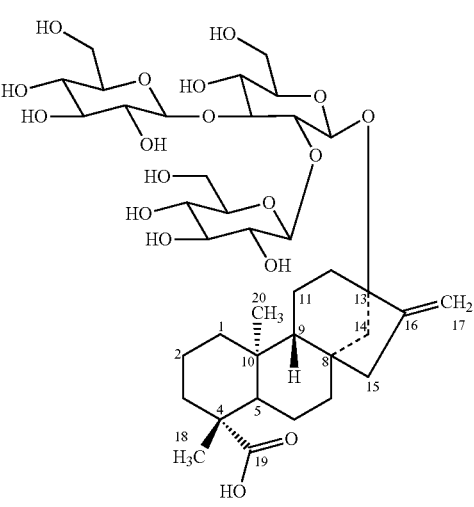 | $C_{38}H_{60}O_{18}$ | 804 |

TABLE 1-continued
Steviol glycosides.
| Name | Structure | Molecular Formula | Molecular Weight |
|---|---|---|---|
| Rebaudioside C | 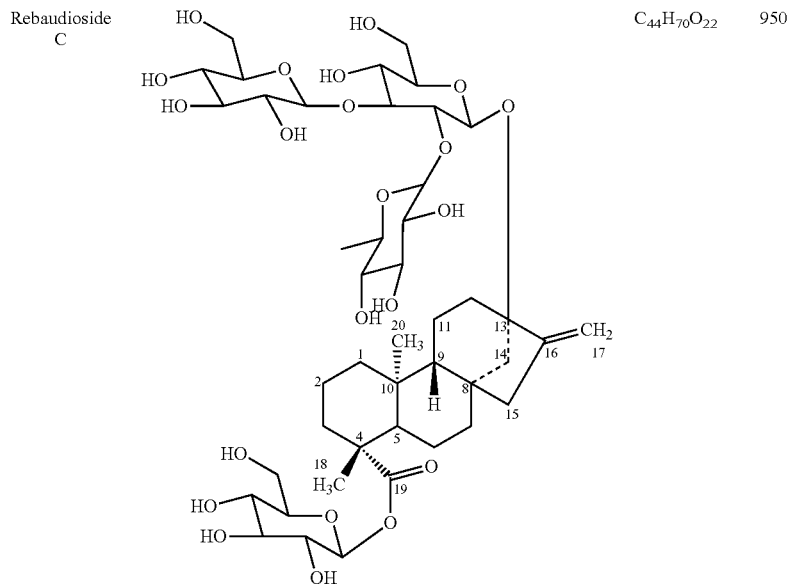 | $C_{44}H_{70}O_{22}$ | 950 |
| Rebaudioside D | 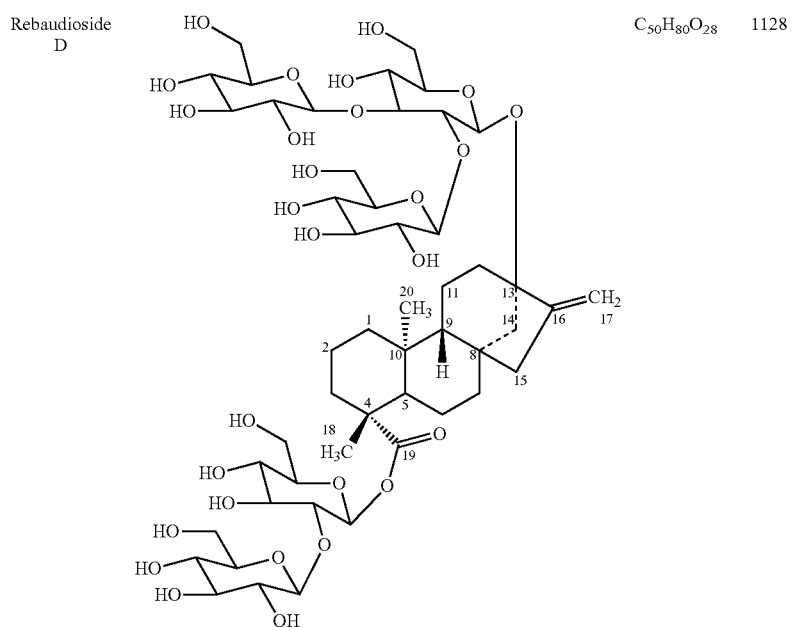 | $C_{50}H_{80}O_{28}$ | 1128 |

TABLE 1-continued
Steviol glycosides.
| Name | Structure | Molecular Formula | Molecular Weight |
|------|-----------|-------------------|------------------|
| Rebaudioside E | 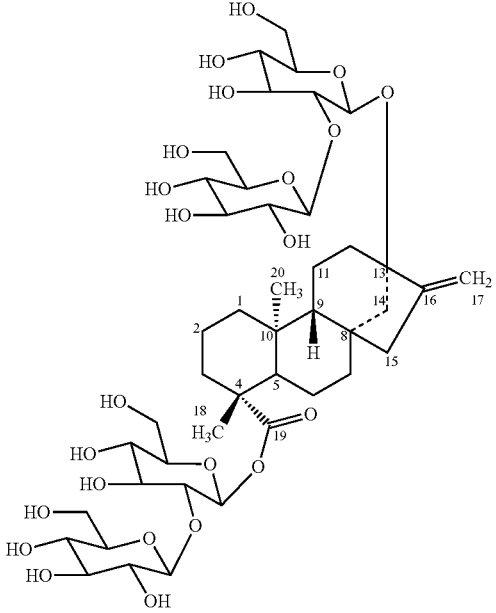 | $C_{44}H_{70}O_{23}$ | 966 |
| Rebaudioside F | 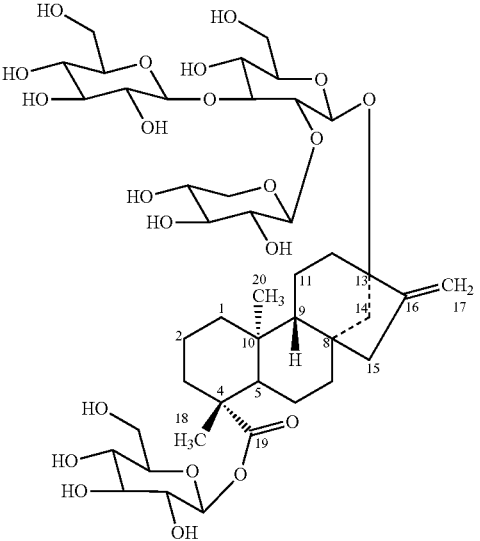 | $C_{43}H_{68}O_{22}$ | 936 |

TABLE 1-continued

Steviol glycosides.

| Name | Structure | Molecular Formula | Molecular Weight |
|---|---|---|---|
| Rebaudioside G | 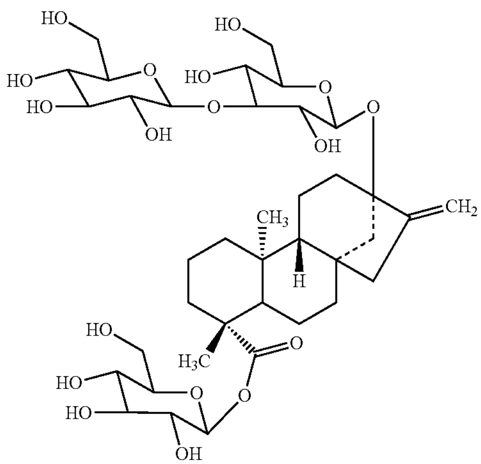 | $C_{38}H_{60}O_{18}$ | 804 |
| Rebaudioside D3 | 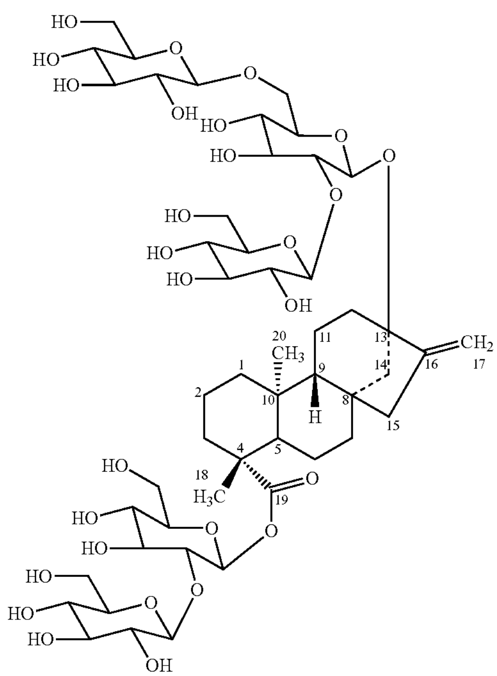 | $C_{50}H_{80}O_{28}$ | 1128 |

TABLE 1-continued

Steviol glycosides.

| Name | Structure | Molecular Formula | Molecular Weight |
|---|---|---|---|
| Rebaudioside KA | (structure) | $C_{38}H_{60}O_{18}$ | 804 |
| Dulcoside A | (structure) | $C_{38}H_{60}O_{17}$ | 788 |

On a dry weight basis, stevioside, rebaudioside A, rebaudioside C, and dulcoside A, account for 9.1, 3.8, 0.6, and 0.3% of the total weight of the steviol glycosides in the leaves, respectively, while the other steviol glycosides are present in much lower amounts. Extracts from the *Stevia rebaudiana* plant are commercially available, which typically contain stevioside and rebaudioside A as primary compounds. The other steviol glycosides typically are present in the stevia extract as minor components. For example, the amount of rebaudioside A in commercial preparations can vary from about 20% to more than 90% of the total steviol glycoside content, while the amount of rebaudioside B can be about 1-2%, the amount of rebaudioside C can be about 7-15%, and the amount of rebaudioside D can be about 2% of the total steviol glycosides.

The majority of steviol glycosides are formed by several glycosylation reactions of steviol, which are typically catalyzed by the UDP-glycosyltransferases (UGTs) using uridine 5'-diphosphoglucose (UDP-glucose) as a donor of the sugar moiety. UGTs in plants make up a very diverse group of enzymes that transfer a glucose residue from UDP-glucose to steviol. For example, glycosylation of the C-3' of the C-13-O-glucose of stevioside yields rebaudioside A; and glycosylation of the C-2' of the 19-O-glucose of the stevioside yields rebaudioside E. Further glycosylation of rebaudioside A (at C-2'-19-O-glucose) or rebaudioside E (at C-3'-13-O-glucose) produces rebaudioside D. (FIG. 1A and FIG. 1B).

Alternative sweeteners are receiving increasing attention due to awareness of many diseases in conjunction with the consumption of high-sugar foods and beverages. Although artificial sweeteners are available, many artificial sweeteners such as dulcin, sodium cyclamate and saccharin have been banned or restricted by some countries due to concerns over their safety. Therefore, non-caloric sweeteners of natural origin are becoming increasingly popular. One of the main obstacles for the widespread use of stevia sweeteners are their undesirable taste attributes. Accordingly, there exists a need to develop alternative sweeteners and methods for their production to provide the best combination of sweetness potency and flavor profile.

SUMMARY OF THE DISCLOSURE

The present disclosure relates generally to natural sweeteners. More particularly, the present disclosure relates to non-caloric sweeteners and methods for synthesizing the non-caloric sweeteners.

Synthetic Rebaudioside V.

In one aspect, the present disclosure is directed to a synthetic rebaudioside (rebaudioside V) consisting of a chemical structure:

Reb V

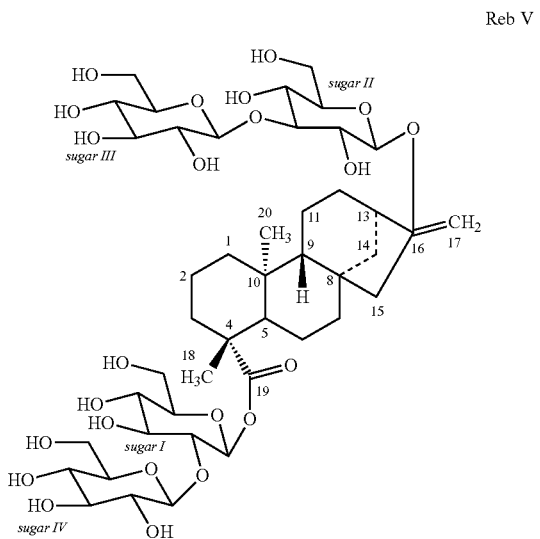

Synthetic Rebaudioside W.

In one aspect, the present disclosure is directed to a synthetic rebaudioside (rebaudioside W) consisting of a chemical structure:

Reb W

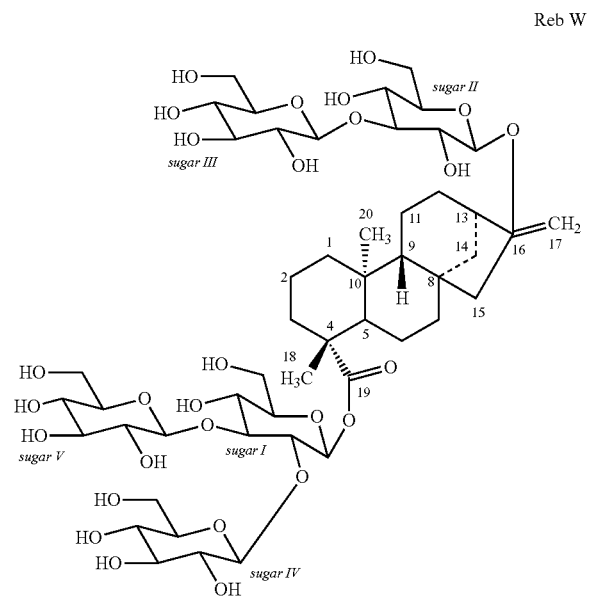

Method of Producing Rebaudioside V from Rebaudioside G.

In another aspect, the present disclosure is directed to a method for synthesizing rebaudioside V from rebaudioside G. The method includes preparing a reaction mixture comprising rebaudioside G, substrates selected from the group consisting of sucrose, uridine diphosphate (UDP) and uridine diphosphate-glucose (UDP-glucose), and a HV1 UDP-glycosyltransferase, with or without sucrose synthase (SUS); and incubating the reaction mixture for a sufficient time to produce rebaudioside V, wherein a glucose is covalently coupled to the rebaudioside G to produce rebaudioside V.

Method of Producing Rebaudioside V from Rebaudioside G.

In another aspect, the present disclosure is directed to a method for synthesizing rebaudioside V from rebaudioside G. The method includes preparing a reaction mixture comprising rebaudioside G, substrates selected from the group consisting of sucrose, uridine diphosphate (UDP) and uridine diphosphate-glucose (UDP-glucose), a uridine diphospho glycosyltransferase (UDP-glycosyltransferase) selected from the group consisting of a uridine diphospho glycosyltransferase (EUGT11), a UDP-glycosyltransferase-Sucrose synthase (SUS) fusion enzyme, with or without sucrose synthase (SUS); and incubating the reaction mixture for a sufficient time to produce rebaudioside V, wherein a glucose is covalently coupled to the rebaudioside G to produce rebaudioside V.

Method of Producing Rebaudioside V from Rebaudioside KA.

In another aspect, the present disclosure is directed to a method for synthesizing rebaudioside V from rebaudioside KA. The method includes preparing a reaction mixture comprising rebaudioside KA, substrates selected from the group consisting of sucrose, uridine diphosphate (UDP) and uridine diphosphate-glucose (UDP-glucose), a uridine diphospho glycosyltransferase (UDP-glycosyltransferase) selected from the group consisting of a UDP-glycosyltransferase (UGT76G1; SEQ ID NO:1) and a UDP-glycosyltransferase-Sucrose synthase fusion enzyme, with or without sucrose synthase (SUS); and incubating the reaction mixture for a sufficient time to produce rebaudioside V, wherein a glucose is covalently coupled to the rebaudioside KA to produce rebaudioside V.

Method of Producing Rebaudioside V from Rubusoside.

In another aspect, the present disclosure is directed to a method for synthesizing rebaudioside V from rubusoside. The method includes preparing a reaction mixture comprising rubusoside, substrates selected from the group consisting of sucrose, uridine diphosphate (UDP) and uridine diphosphate-glucose (UDP-glucose), uridine diphospho glycosyltransferases (UDP-glycosyltransferase) selected from the group consisting of a UDP-glycosyltransferase (UGT76G1), HV1 and a UDP-glycosyltransferase-Sucrose synthase fusion enzyme, with or without sucrose synthase (SUS); and incubating the reaction mixture for a sufficient time to produce rebaudioside V, wherein a glucose is covalently coupled to the rubusoside to produce rebaudioside KA. Continually, a glucose is covalently coupled to the rebaudioside KA to produce rebaudioside V. A glucose is covalently coupled to the rubusoside to produce rebaudioside G. Continually, a glucose is covalently coupled to the rebaudioside G to produce rebaudioside V.

Method of Producing Rebaudioside V from Rubusoside.

In another aspect, the present disclosure is directed to a method for synthesizing rebaudioside V from rubusoside.

The method includes preparing a reaction mixture comprising rubusoside, substrates selected from the group consisting of sucrose, uridine diphosphate (UDP) and uridine diphosphate-glucose (UDP-glucose), uridine dipospho glycosyltransferases (UDP-glycosyltransferase) selected from the group consisting of a UDP-glycosyltransferase (UGT76G1), EUGT11 and a UDP-glycosyltransferase-Sucrose synthase fusion enzyme, with or without sucrose synthase; and incubating the reaction mixture for a sufficient time to produce rebaudioside V, wherein a glucose is covalently coupled to the rubusoside to produce rebaudioside KA and a glucose is covalently coupled to the rebaudioside KA to produce rebaudioside V. A glucose is covalently coupled to the rubusoside to product rebaudioside G and a glucose is covalently coupled to the rebaudioside G to produce rebaudioside V.

Method of producing Rebaudioside W from Rebaudioside V.

In another aspect, the present disclosure is directed to a method for synthesizing rebaudioside W from rebaudioside V. The method includes preparing a reaction mixture comprising rebaudioside V, substrates selected from the group consisting of sucrose, uridine diphosphate (UDP) and uridine diphosphate-glucose (UDP-glucose), a uridine dipospho glycosyltransferase (UDP-glycosyltransferase) selected from the group consisting of a UDP-glycosyltransferase (UGT76G1) and a UDP-glycosyltransferase-Sucrose synthase fusion enzyme, with or without sucrose synthase; and incubating the reaction mixture for a sufficient time to produce rebaudioside W, wherein a glucose is covalently coupled to the rebaudioside V to produce rebaudioside W.

Method of Producing Rebaudioside W from Rebaudioside G.

In another aspect, the present disclosure is directed to a method for synthesizing rebaudioside W from rebaudioside G. The method includes preparing a reaction mixture comprising rebaudioside G, substrates selected from the group consisting of sucrose, uridine diphosphate (UDP) and uridine diphosphate-glucose (UDP-glucose), uridine dipospho glycosyltransferases (UDP-glycosyltransferase) selected from the group consisting of a UDP-glycosyltransferase (UGT76G1), a UDP-glycosyltransferase-Sucrose synthase fusion enzyme and a HV1; with or without sucrose synthase; and incubating the reaction mixture for a sufficient time to produce rebaudioside W, wherein a glucose is covalently coupled to the rebaudioside G to produce rebaudioside V by HV1. Continually, a glucose is covalently coupled to the rebaudioside V to produce rebaudioside W by UGT76G1.

Method of Producing Rebaudioside W from Rebaudioside G.

In another aspect, the present disclosure is directed to a method for synthesizing rebaudioside W from rebaudioside G. The method includes preparing a reaction mixture comprising rebaudioside G, substrates selected from the group consisting of sucrose, uridine diphosphate (UDP) and uridine diphosphate-glucose (UDP-glucose), uridine diphospho glycosyltransferases (UDP-glycosyltransferase) selected from the group consisting of a UGT76G1, an EUGT11, and a UDP-glycosyltransferase-Sucrose synthase fusion enzyme; and incubating the reaction mixture for a sufficient time to produce rebaudioside W, wherein a glucose is covalently coupled to the rebaudioside G to produce rebaudioside V by EUGT11. Continually, a glucose is covalently coupled to the rebaudioside V to produce rebaudioside W by UGT76G1.

Method of Producing Rebaudioside W from Rebaudioside KA.

In another aspect, the present disclosure is directed to a method for synthesizing rebaudioside W from rebaudioside KA. The method includes preparing a reaction mixture comprising rebaudioside KA; substrates selected from the group consisting of sucrose, uridine diphosphate (UDP) and uridine diphosphate-glucose (UDP-glucose); a uridine dipospho glycosyltransferase (UDP-glycosyltransferase) selected from the group consisting of a UDP-glycosyltransferase (UGT76G1), and a UDP-glycosyltransferase-Sucrose synthase fusion enzyme, with or without sucrose synthase; and incubating the reaction mixture for a sufficient time to produce rebaudioside W, wherein a glucose is covalently coupled to the rebaudioside KA to produce rebaudioside V. Continually, a glucose is covalently coupled to the rebaudioside V to produce rebaudioside W.

Method of Producing of Rebaudioside W from Rubusoside.

In another aspect, the present disclosure is directed to a method for synthesizing rebaudioside D from rubusoside. The method includes preparing a reaction mixture comprising rubusoside, substrates selected from the group consisting of sucrose, uridine diphosphate (UDP) and uridine diphosphate-glucose (UDP-glucose), uridine diphospho glycosyltransferases (UDP-glycosyltransferase) selected from the group consisting of an UGT76G1, a HV1, and a UDP-glycosyltransferase-Sucrose synthase fusion enzyme, with or without sucrose synthase; and incubating the reaction mixture for a sufficient time to produce rebaudioside W.

Method of Producing of Rebaudioside W from Rubusoside.

In another aspect, the present disclosure is directed to a method for synthesizing rebaudioside W from rubusoside. The method includes preparing a reaction mixture comprising rubusoside, substrates selected from the group consisting of sucrose, uridine diphosphate (UDP) and uridine diphosphate-glucose (UDP-glucose), uridine diphospho glycosyltransferases (UDP-glycosyltransferase) selected from the group consisting of an UGT76G1, an EUGT11, and a UDP-glycosyltransferase-Sucrose synthase fusion enzyme, with or without sucrose synthase; and incubating the reaction mixture for a sufficient time to produce rebaudioside W.

Method of Producing a Mixture of Stevioside and Rebaudioside KA from Rubusoside.

In another aspect, the present disclosure is directed to a method for synthesizing a mixture of stevioside and rebaudioside KA from rubusoside. The method includes preparing a reaction mixture comprising rubusoside, substrates selected from the group consisting of sucrose, uridine diphosphate (UDP) and uridine diphosphate-glucose (UDP-glucose), a UDP-glycosyltransferase selected from the group consisting of EUGT11 and a UDP-glycosyltransferase-Sucrose synthase fusion enzyme, with or without sucrose synthase; and incubating the reaction mixture for a sufficient time to produce a mixture of stevioside and rebaudioside KA, wherein a glucose is covalently coupled to C2'-19-O-glucose of rubusoside to produce rebaudioside KA; a glucose is covalently coupled to C2'-13-O-glucose of rubusoside to produce stevioside.

Method of Producing Rebaudioside KA from Rubusoside.

In another aspect, the present disclosure is directed to a method for synthesizing a rebaudioside KA from rubusoside. The method includes preparing a reaction mixture comprising rubusoside, substrates selected from the group consisting of sucrose, uridine diphosphate (UDP) and uridine diphosphate-glucose (UDP-glucose), and HV1, with or without sucrose synthase; and incubating the reaction mixture for a sufficient time to produce rebaudioside KA, wherein a glucose is covalently coupled to the C2'-19-O-glucose of rubusoside to produce a rebaudioside KA.

Method of Producing Rebaudioside G from Rubusoside.

In another aspect, the present disclosure is directed to a method for synthesizing a rebaudioside G from rubusoside. The method includes preparing a reaction mixture comprising rubusoside, substrates selected from the group consisting of sucrose, uridine diphosphate (UDP) and uridine diphosphate-glucose (UDP-glucose), a UDP-glycosyltransferase selected from the group consisting of UGT76G1 and a UDP-glycosyltransferase-Sucrose synthase fusion enzyme, with or without sucrose synthase; and incubating the reaction mixture for a sufficient time to produce rebaudioside G, wherein a glucose is covalently coupled to the C3'-13-O-glucose of rubusoside to produce a rebaudioside G.

Method of Producing Rebaudioside E from Rebaudioside KA.

In another aspect, the present disclosure is directed to a method for synthesizing rebaudioside E from rebaudioside KA. The method includes preparing a reaction mixture comprising rebaudioside KA, substrates selected from the group consisting of sucrose, uridine diphosphate (UDP) and uridine diphosphate-glucose (UDP-glucose) and HV1 UDP-glycosyltransferase, with or without sucrose synthase; and incubating the reaction mixture for a sufficient time to produce rebaudioside E, wherein a glucose is covalently coupled to the C2' 13-O-glucose of rebaudioside KA to produce rebaudioside E.

Method of Producing Rebaudioside E from Rebaudioside KA.

In another aspect, the present disclosure is directed to a method for synthesizing rebaudioside E from rebaudioside KA. The method includes preparing a reaction mixture comprising rebaudioside KA, substrates selected from the group consisting of sucrose, uridine diphosphate (UDP) and uridine diphosphate-glucose (UDP-glucose), a UDP-glycosyltransferase selected from the group consisting of an EUGT11 and a UDP-glycosyltransferase-Sucrose synthase fusion enzyme, with or without sucrose synthase; and incubating the reaction mixture for a sufficient time to produce rebaudioside E, wherein a glucose is covalently coupled to the C2' 13-O-glucose of rebaudioside KA to produce rebaudioside E.

Method of Producing Rebaudioside E from Rubusoside.

In another aspect, the present disclosure is directed to a method for synthesizing rebaudioside E from rubusoside. The method includes preparing a reaction mixture comprising rubusoside, substrates selected from the group consisting of sucrose, uridine diphosphate (UDP) and uridine diphosphate-glucose (UDP-glucose), and a UDP-glycosyltransferase from the group of EUGT11 and a UDP-glycosyltransferase-Sucrose synthesis fusion enzyme, with or without sucrose synthase; and incubating the reaction mixture for a sufficient time to produce rebaudioside E, wherein a glucose is covalently coupled to rubusoside to produce a mixture of rebaudioside KA and stevioside. Continually, a glucose is covalently coupled to rebaudioside KA and stevioside to produce rebaudioside E.

Method of Producing Rebaudioside E from Rubusoside.

In another aspect, the present disclosure is directed to a method for synthesizing rebaudioside E from rubusoside. The method includes preparing a reaction mixture comprising rubusoside, substrates selected from the group consisting of sucrose, uridine diphosphate (UDP) and uridine diphosphate-glucose (UDP-glucose) and HV1 UDP-glycosyltransferase, with or without sucrose synthase; incubating the reaction mixture for a sufficient time to produce rebaudioside E, wherein a glucose is covalently coupled to the rubusoside to produce rebaudioside KA; and further incubating the rebaudioside KA with HV1 to produce rebaudioside E.

Method of Producing Rebaudioside D3 from Rubusoside.

In another aspect, the present disclosure is directed to a method for synthesizing rebaudioside D3 from rubusoside. The method includes preparing a reaction mixture comprising rubusoside, substrates selected from the group consisting of sucrose, uridine diphosphate (UDP) and uridine diphosphate-glucose (UDP-glucose), a UDP-glycosyltransferase from the group of an EUGT11 and a UDP-glycosyltransferase-Sucrose synthase fusion enzyme, with or without sucrose synthase; incubating the reaction mixture for a sufficient time to produce a mixture of stevioside and rebaudioside D3, wherein a glucose is covalently coupled to the rubusoside to produce a mixture of stevioside and rebaudioside KA; further incubating the mixture of stevioside and rebaudioside KA with EUGT11 to produce rebaudioside E, wherein a glucose is covalently coupled to the stevioside and the rebaudioside KA to produce rebaudioside E; and further incubating the rebaudioside E with EUGT11 to produce rebaudioside D3, wherein a glucose is covalently coupled to the rebaudioside E to produce rebaudioside D3.

Method of Producing Rebaudioside D3 from Rebaudioside KA.

In another aspect, the present disclosure is directed to a method for synthesizing rebaudioside D3 from rebaudioside KA. The method includes preparing a reaction mixture comprising rebaudioside KA, substrates selected from the group consisting of sucrose, uridine diphosphate (UDP) and uridine diphosphate-glucose (UDP-glucose), a UDP-glycosyltransferase selected from the group consisting of an EUGT11 and a UDP-glycosyltransferase-Sucrose synthase fusion enzyme, with or without sucrose synthase; incubating the reaction mixture for a sufficient time to produce rebaudioside D3, wherein a glucose is covalently coupled to the rebaudioside KA to produce rebaudioside E; further incubating the mixture of rebaudioside E with EUGT11 to produce rebaudioside D3, wherein a glucose is covalently coupled to the rebaudioside E to produce rebaudioside D3.

Method of Producing Rebaudioside Z from Rebaudioside E.

In another aspect, the present disclosure is directed to a method for synthesizing rebaudioside Z from rebaudioside E. The method includes preparing a reaction mixture comprising rebaudioside E, substrates selected from the group consisting of sucrose, uridine diphosphate (UDP) and uridine diphosphate-glucose (UDP-glucose), HV1 and sucrose synthase; incubating the reaction mixture for a sufficient time to produce rebaudioside Z, wherein a glucose is covalently coupled to the C2'-13-O-glucose of rebaudioside E to produce rebaudioside Z1. A glucose is covalently coupled to C2'-19-O-glucose of rebaudioside E to produce rebaudioside Z2.

Method of Producing Rebaudioside M from Rebaudioside D.

In another aspect, the present disclosure is directed to a method for synthesizing rebaudioside M from rebaudioside D. The method includes preparing a reaction mixture comprising rebaudioside D, substrates selected from the group consisting of sucrose, uridine diphosphate (UDP), uridine diphosphate-glucose (UDP-glucose), and combinations thereof, and a UDP-glycosyltransferase selected from the group consisting of UGT76G1, a UDP-glycosyltransferase-Sucrose synthase fusion enzyme, and combinations thereof, with or without sucrose synthase; and incubating the reaction mixture for a sufficient time to produce rebaudioside M, wherein a glucose is covalently coupled to the rebaudioside D to produce rebaudioside M.

Method of Producing Rebaudioside D and Rebaudioside M from Stevioside.

In another aspect, the present disclosure is directed to a method for synthesizing rebaudioside D and rebaudioside M from stevioside. The method includes preparing a reaction mixture comprising stevioside, substrates selected from the group consisting of sucrose, uridine diphosphate (UDP), uridine diphosphate-glucose (UDP-glucose), and combinations thereof, and a UDP-glycosyltransferase selected from the group consisting of HV1, UGT76G1, a UDP-glycosyltransferase-Sucrose synthase fusion enzyme, and combinations thereof, with or without sucrose synthase; and incubating the reaction mixture for a sufficient time to produce rebaudioside M. In certain embodiments, a glucose is covalently coupled to the stevioside to produce rebaudioside A and/or rebaudioside E. Continually, a glucose is covalently coupled to the rebaudioside A and/or rebaudioside E to produce rebaudioside D, and a glucose is covalently coupled to the rebaudioside D to produce rebaudioside M.

Method of Producing Rebaudioside D and Rebaudioside M from Rebaudioside A.

In another aspect, the present disclosure is directed to a method for synthesizing rebaudioside D and rebaudioside M from rebaudioside A. The method includes preparing a reaction mixture comprising rebaudioside A, substrates selected from the group consisting of sucrose, uridine diphosphate (UDP), uridine diphosphate-glucose (UDP-glucose), and combinations thereof, and a UDP-glycosyltransferase selected from the group consisting of HV1, UGT76G1, a UDP-glycosyltransferase-Sucrose synthase fusion enzyme, and combinations thereof, with or without sucrose synthase; and incubating the reaction mixture for a sufficient time to produce rebaudioside M, wherein a glucose is covalently coupled to the rebaudioside A to produce rebaudioside D, and a glucose is covalently coupled to the rebaudioside D to produce rebaudioside M.

Method of Producing Rebaudioside D and Rebaudioside M from Rebaudioside E.

In another aspect, the present disclosure is directed to a method for synthesizing rebaudioside D and rebaudioside M from rebaudioside E. The method includes preparing a reaction mixture comprising rebaudioside E, substrates selected from the group consisting of sucrose, uridine diphosphate (UDP), uridine diphosphate-glucose (UDP-glucose), and combinations thereof, and a UDP-glycosyltransferase selected from the group consisting of an UGT76G1, a UDP-glycosyltransferase-Sucrose synthase fusion enzyme, and combinations thereof, with or without sucrose synthase; and incubating the reaction mixture for a sufficient time to produce rebaudioside M, wherein a glucose is covalently coupled to the rebaudioside E to produce rebaudioside D, and wherein a glucose is covalently coupled to the rebaudioside D to produce rebaudioside M.

In another aspect, the present disclosure is directed to an orally consumable product comprising a sweetening amount of a rebaudioside selected from rebaudioside V, rebaudioside W, rebaudioside G, rebaudioside KA, rebaudioside M, and combinations thereof, wherein the orally consumable product is selected from the group consisting of a beverage product and a consumable product.

In another aspect, the present disclosure is directed to a beverage product comprising a sweetening amount of a rebaudioside selected from rebaudioside V, rebaudioside W, rebaudioside G, rebaudioside KA, rebaudioside M, and combinations thereof. The rebaudioside is present in the beverage product at a concentration of about 5 ppm to about 100 ppm. In some embodiments, low concentrations of rebaudioside, e.g., below 100 ppm, has an equivalent sweetness to sucrose solutions having concentrations between 10,000 and 30,000 ppm.

In another aspect, the present disclosure is directed to a consumable product comprising a sweetening amount of a rebaudioside selected from rebaudioside V, rebaudioside W, rebaudioside G, rebaudioside KA, rebaudioside M, and combinations thereof. The rebaudioside is present in the consumable product at a concentration of about 5 ppm to about 100 ppm. In some embodiments, low concentrations of rebaudioside, e.g., below 100 ppm, has an equivalent sweetness to sucrose solutions having concentrations between 10,000 and 30,000 ppm.

In another aspect, the present disclosure is directed to a sweetener consisting of a chemical structure:

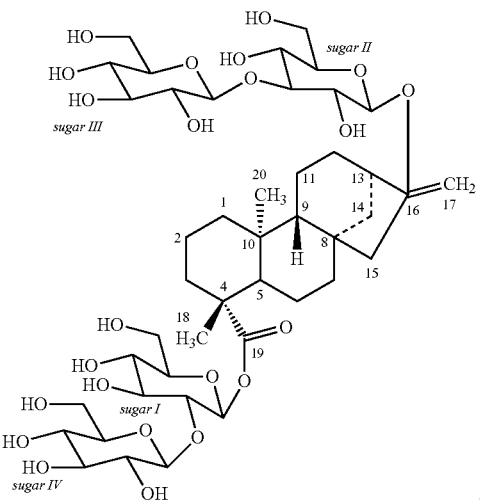

Reb V

In another aspect, the present disclosure is directed to a sweetener consisting of a chemical structure:

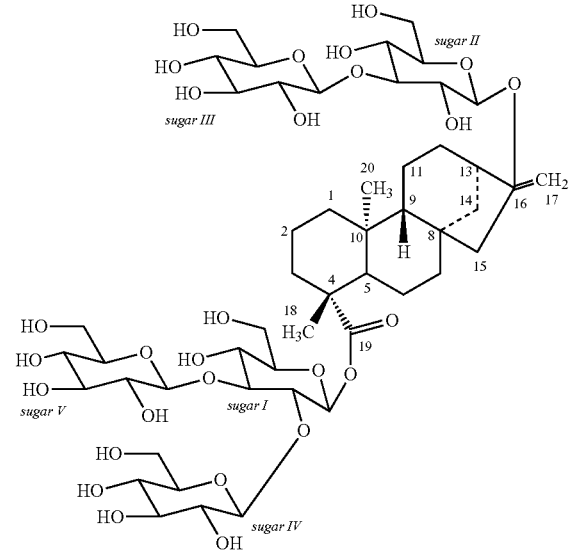

Reb W

In certain embodiments that can be combined with any of the preceding embodiments, the rebaudioside V or the rebaudioside W or the rebaudioside G or the rebaudioside KA or the rebaudioside M can be the only sweetener, and the product has a sweetness intensity equivalent to about 1% to about 4% (w/v-%) sucrose solution. In certain embodiments that can be combined with any of the preceding embodiments, the orally consumable product further can include an additional sweetener, where the product has a sweetness intensity equivalent to about 1% to about 10% (w/v-%) sucrose solution. In certain embodiments that can be combined with any of the preceding embodiments, every sweetening ingredient in the product can be a high intensity sweetener. In certain embodiments that can be combined with any of the preceding embodiments, every sweetening ingredient in the product can be a natural high intensity sweetener. In certain embodiments that can be combined with any of the preceding embodiments, the additional sweetener can be one or more sweeteners selected from a stevia extract, a steviol glycoside, stevioside, rebaudioside A, rebaudioside B, rebaudioside C, rebaudioside D, rebaudioside D3, rebaudioside E, rebaudioside F, rebaudioside G, rebaudioside KA, rebaudioside M, dulcoside A, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, mogroside IV, siamenoside I, mogroside V, monatin, thaumatin, monellin, brazzein, L-alanine, glycine, Lo Han Guo, hernandulcin, phyllodulcin, trilobtain, and combinations thereof. In certain embodiments that can be combined with any of the preceding embodiments, the beverage product and consumable product can further include one or more additives selected from a carbohydrate, a polyol, an amino acid or salt thereof, a poly-amino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoids, an alcohol, a polymer, and combinations thereof. In certain embodiments that can be combined with any of the preceding embodiments, the rebaudioside V has a purity of about 50% to about 100% by weight before it is added into the product. In certain embodiments that can be combined with any of the preceding embodiments, the W has a purity of about 50% to about 100% by weight before it is added into the product. In certain embodiments that can be combined with any of the preceding embodiments, the rebaudioside V in the product is a rebaudioside V polymorph or amorphous rebaudioside V. In certain embodiments that can be combined with any of the preceding embodiments, the rebaudioside V in the product is a rebaudioside V stereoisomer. In certain embodiments that can be combined with any of the preceding embodiments, the rebaudioside W in the product is a rebaudioside W polymorph or amorphous rebaudioside W. In certain embodiments that can be combined with any of the preceding embodiments, the rebaudioside W in the product is a rebaudioside W stereoisomer.

Other aspects of the present disclosure relate to a method of preparing a beverage product and a consumable product by including synthesized rebaudioside selected from rebaudioside V, rebaudioside W, rebaudioside KA, rebaudioside M, and rebaudioside G into the product or into the ingredients for making the beverage product and the consumable product, where rebaudioside selected from rebaudioside V, rebaudioside W, rebaudioside KA, rebaudioside M, and rebaudioside G is present in the product at a concentration of from about 5 ppm to about 100 ppm. Other aspects of the present disclosure relate to a method for enhancing the sweetness of a beverage product and a consumable product by adding from about 5 ppm to about 100 ppm of synthesized rebaudioside selected from rebaudioside V, rebaudioside W, rebaudioside KA, rebaudioside M, and rebaudioside G into the beverage product and the consumable product, where the added synthesized rebaudioside selected from rebaudioside V, rebaudioside W, rebaudioside KA, rebaudioside M, and rebaudioside G enhances the sweetness of the beverage product and the consumable product, as compared to a corresponding a beverage product and a consumable product lacking the synthesized rebaudioside selected from rebaudioside V, rebaudioside W, rebaudioside KA, rebaudioside M, and rebaudioside G.

In certain embodiments that can be combined with any of the preceding embodiments, rebaudioside V is the only sweetener, and the product has a sweetness intensity equivalent to about 1% to about 4% (w/v-%) sucrose solution. In certain embodiment that can be combined with any of the proceeding embodiments, rebaudioside KA is the only sweetener, and the product has a sweetness intensity equivalent to about 1% to about 4% (w/v-%) sucrose solution. In certain embodiments that can be combined with any of the proceeding embodiments, rebaudioside G is the only sweetener, and the product has a sweetness intensity equivalent to about 1% to about 4% (w/v-%) sucrose solution. In certain embodiments that can be combined with any of the preceding embodiments, rebaudioside W is the only sweetener, and the product has a sweetness intensity equivalent to about 1% to about 4% (w/v-%) sucrose solution. In certain embodiments that can be combined with any of the preceding embodiments, rebaudioside M is the only sweetener, and the product has a sweetness intensity equivalent to about 1% to about 4% (w/v-%) sucrose solution. In certain embodiments that can be combined with any of the preceding embodiments, the method further includes adding an additional sweetener, where the product has a sweetness intensity equivalent to about 1% to about 10% (w/v-%) sucrose solution.

Other aspects of the present disclosure relate to a method for preparing a sweetened beverage product or a sweetened consumable product by: a) providing a beverage product or a consumable product containing one or more sweetener; and b) adding from about 5 ppm to about 100 ppm of a synthesized rebaudioside selected from rebaudioside V, rebaudioside W, rebaudioside KA, rebaudioside M, and rebaudioside G, and combinations thereof into the beverage product or the consumable product.

In certain embodiments that can be combined with any of the preceding embodiments, the method further includes adding one or more additives to the beverage product or the consumable product. In certain embodiments that can be combined with any of the preceding embodiments, the orally consumable product further contains one or more additives. In certain embodiments that can be combined with any of the preceding embodiments, the one or more additives are selected from a carbohydrate, a polyol, an amino acid or salt thereof, a poly-amino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoids, an alcohol, a polymer, and combinations thereof. In certain embodiments that may be combined with any of the preceding embodiments, every sweetening ingredient in the product is a high intensity sweetener. In certain embodiments that can be combined with any of the preceding embodiments, every sweetening ingredient in the product is a natural high intensity sweetener. In certain embodiments that can be combined with any of the preceding embodiments, the sweetener is selected from a stevia extract, a steviol glycoside, stevioside, rebaudioside A, rebaudioside B, rebaudioside C, rebaudioside D, rebaudioside D3, rebaudioside E, rebaudioside F, rebaudioside G, rebaudioside KA, rebaudioside M, dulcoside A, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, mogroside IV, siamenoside I, mogroside V, monatin, thaumatin, monellin, brazzein, L-alanine, glycine, Lo Han Guo, hernandulcin, phyllodulcin, trilobtain, and combinations thereof. In certain embodiments that can be combined with any of the preceding embodiments, the rebaudioside V has a purity of about 50% to about 100% by weight before it is added into the product. In certain embodiments that can be combined with any of the preceding embodiments, the rebaudioside V in the product is a rebaudioside V polymorph or amorphous rebaudioside V. In certain embodiments that can be combined with any of the preceding embodiments, the rebaudioside W has a purity of about 50% to about 100% by weight before it is added into the product. In certain embodiments that can be combined with any of the preceding embodiments, the rebaudioside W in the product is a rebaudioside W polymorph or amorphous rebaudioside W.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

Figure 1A:
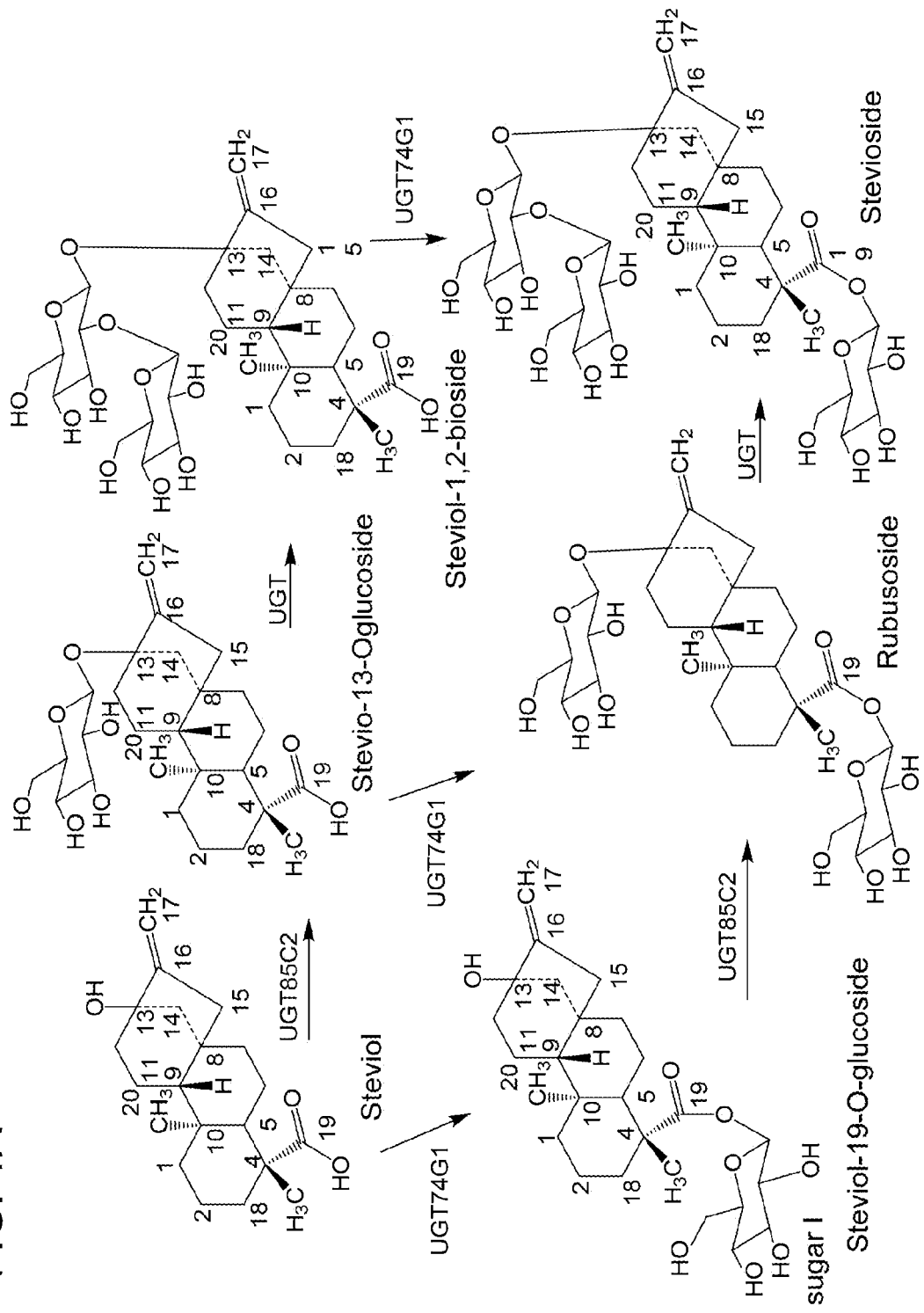
FIG. 1A and FIG. 1B depict a steviol glycosides biosynthesis pathway from steviol.
Figure 1B:
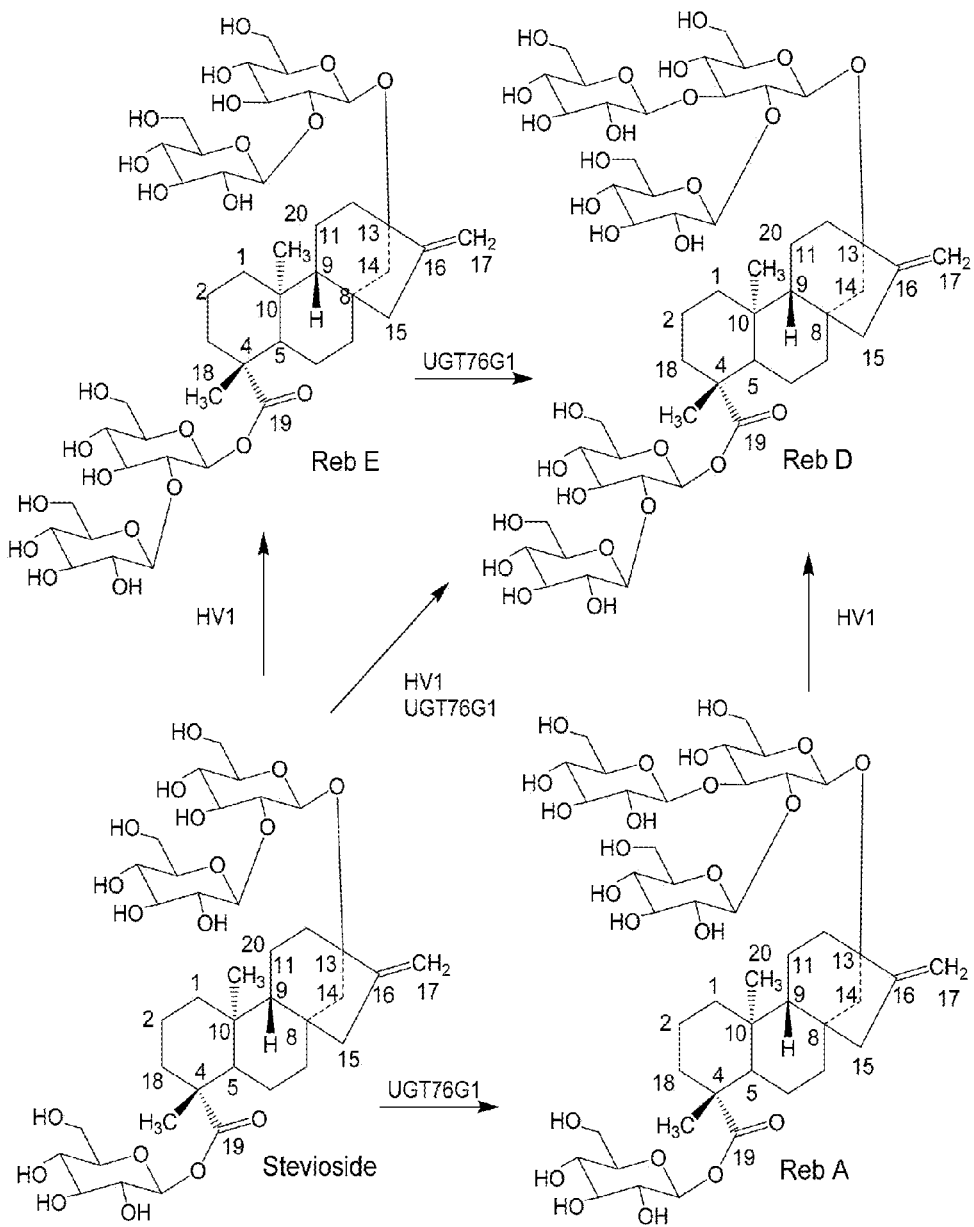

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

The term "complementary" is used according to its ordinary and customary meaning as understood by a person of ordinary skill in the art, and is used without limitation to describe the relationship between nucleotide bases that are capable to hybridizing to one another. For example, with respect to DNA, adenosine is complementary to thymine and cytosine is complementary to guanine. Accordingly, the subject technology also includes isolated nucleic acid fragments that are complementary to the complete sequences as reported in the accompanying Sequence Listing as well as those substantially similar nucleic acid sequences.

The terms "nucleic acid" and "nucleotide" are used according to their respective ordinary and customary meanings as understood by a person of ordinary skill in the art, and are used without limitation to refer to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified or degenerate variants thereof (e.g., degenerate codon substitutions) and complementary sequences, as well as the sequence explicitly indicated.

The term "isolated" is used according to its ordinary and customary meaning as understood by a person of ordinary skill in the art, and when used in the context of an isolated nucleic acid or an isolated polypeptide, is used without limitation to refer to a nucleic acid or polypeptide that, by the hand of man, exists apart from its native environment and is therefore not a product of nature. An isolated nucleic acid or polypeptide can exist in a purified form or can exist in a non-native environment such as, for example, in a transgenic host cell.

The terms "incubating" and "incubation" as used herein refers to a process of mixing two or more chemical or biological entities (such as a chemical compound and an enzyme) and allowing them to interact under conditions favorable for producing a steviol glycoside composition.

The term "degenerate variant" refers to a nucleic acid sequence having a residue sequence that differs from a reference nucleic acid sequence by one or more degenerate codon substitutions. Degenerate codon substitutions can be achieved by generating sequences in which the third position of one or more selected (or all) codons is substituted with mixed base and/or deoxyinosine residues. A nucleic acid sequence and all of its degenerate variants will express the same amino acid or polypeptide.

The terms "polypeptide," "protein," and "peptide" are used according to their respective ordinary and customary meanings as understood by a person of ordinary skill in the art; the three terms are sometimes used interchangeably, and are used without limitation to refer to a polymer of amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein," "polypeptide," and "peptide" are used interchangeably herein when referring to a polynucleotide product. Thus, exemplary polypeptides include polynucleotide products, naturally occurring proteins, homologs, orthologs, paralogs, fragments and other equivalents, variants, and analogs of the foregoing.

The terms "polypeptide fragment" and "fragment," when used in reference to a reference polypeptide, are used according to their ordinary and customary meanings to a person of ordinary skill in the art, and are used without limitation to refer to a polypeptide in which amino acid residues are deleted as compared to the reference polypeptide itself, but where the remaining amino acid sequence is usually identical to the corresponding positions in the reference polypeptide. Such deletions can occur at the amino-terminus or carboxy-terminus of the reference polypeptide, or alternatively both.

The term "functional fragment" of a polypeptide or protein refers to a peptide fragment that is a portion of the full length polypeptide or protein, and has substantially the same biological activity, or carries out substantially the same function as the full length polypeptide or protein (e.g., carrying out the same enzymatic reaction).

The terms "variant polypeptide," "modified amino acid sequence" or "modified polypeptide," which are used interchangeably, refer to an amino acid sequence that is different from the reference polypeptide by one or more amino acids, e.g., by one or more amino acid substitutions, deletions, and/or additions. In an aspect, a variant is a "functional variant" which retains some or all of the ability of the reference polypeptide.

The term "functional variant" further includes conservatively substituted variants. The term "conservatively substituted variant" refers to a peptide having an amino acid sequence that differs from a reference peptide by one or more conservative amino acid substitutions, and maintains some or all of the activity of the reference peptide. A "conservative amino acid substitution" is a substitution of an amino acid residue with a functionally similar residue. Examples of conservative substitutions include the substitution of one non-polar (hydrophobic) residue such as isoleucine, valine, leucine or methionine for another; the substitution of one charged or polar (hydrophilic) residue for another such as between arginine and lysine, between glutamine and asparagine, between threonine and serine; the substitution of one basic residue such as lysine or arginine for another; or the substitution of one acidic residue, such as aspartic acid or glutamic acid for another; or the substitution of one aromatic residue, such as phenylalanine, tyrosine, or tryptophan for another. Such substitutions are expected to have little or no effect on the apparent molecular weight or isoelectric point of the protein or polypeptide. The phrase "conservatively substituted variant" also includes peptides wherein a residue is replaced with a chemically-derivatized residue, provided that the resulting peptide maintains some or all of the activity of the reference peptide as described herein.

The term "variant," in connection with the polypeptides of the subject technology, further includes a functionally active polypeptide having an amino acid sequence at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical to the amino acid sequence of a reference polypeptide.

The term "homologous" in all its grammatical forms and spelling variations refers to the relationship between polynucleotides or polypeptides that possess a "common evolutionary origin," including polynucleotides or polypeptides from superfamilies and homologous polynucleotides or proteins from different species (Reeck et al., Cell 50:667, 1987). Such polynucleotides or polypeptides have sequence homology, as reflected by their sequence similarity, whether in terms of percent identity or the presence of specific amino acids or motifs at conserved positions. For example, two homologous polypeptides can have amino acid sequences that are at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, and even 100% identical.

"Percent (%) amino acid sequence identity" with respect to the variant polypeptide sequences of the subject technology refers to the percentage of amino acid residues in a candidate sequence that are identical with the amino acid residues of a reference polypeptide after aligning the sequences and introducing gaps, if necessary, to achieve the maximum percent sequence identity, and not considering any conservative substitutions as part of the sequence identity.

Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example, the % amino acid sequence identity may be determined using the sequence comparison program NCBI-BLAST2. The NCBI-BLAST2 sequence comparison program may be downloaded from ncbi.nlm.nih.gov. NCBI BLAST2 uses several search parameters, wherein all of those search parameters are set to default values including, for example, unmask yes, strand=all, expected occurrences 10, minimum low complexity length=15/5, multi-pass e-value=0.01, constant for multi-pass=25, dropoff for final gapped alignment=25 and scoring matrix=BLOSUM62. In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

In this sense, techniques for determining amino acid sequence "similarity" are well known in the art. In general, "similarity" refers to the exact amino acid to amino acid comparison of two or more polypeptides at the appropriate place, where amino acids are identical or possess similar chemical and/or physical properties such as charge or hydrophobicity. A so-termed "percent similarity" may then be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded therein, and comparing this to a second amino acid sequence. In general, "identity" refers to an exact nucleotide to nucleotide or amino acid to amino acid correspondence of two polynucleotides or polypeptide sequences, respectively. Two or more polynucleotide sequences can be compared by determining their "percent identity", as can two or more amino acid sequences. The programs available in the Wisconsin Sequence Analysis Package, Version 8 (available from Genetics Computer Group, Madison, Wis.), for example, the GAP program, are capable of calculating both the identity between two polynucleotides and the identity and similarity between two polypeptide sequences, respectively. Other programs for calculating identity or similarity between sequences are known by those skilled in the art.

An amino acid position "corresponding to" a reference position refers to a position that aligns with a reference sequence, as identified by aligning the amino acid sequences. Such alignments can be done by hand or by using well-known sequence alignment programs such as ClustalW2, Blast 2, etc.

Unless specified otherwise, the percent identity of two polypeptide or polynucleotide sequences refers to the percentage of identical amino acid residues or nucleotides across the entire length of the shorter of the two sequences.

"Coding sequence" is used according to its ordinary and customary meaning as understood by a person of ordinary skill in the art, and is used without limitation to refer to a DNA sequence that encodes for a specific amino acid sequence.

"Suitable regulatory sequences" is used according to its ordinary and customary meaning as understood by a person of ordinary skill in the art, and is used without limitation to refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" is used according to its ordinary and customary meaning as understood by a person of ordinary skill in the art, and is used without limitation to refer to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different cell types, or at different stages of development, or in response to different environmental conditions. Promoters, which cause a gene to be expressed in most cell types at most times, are commonly referred to as "constitutive promoters." It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression" as used herein, is used according to its ordinary and customary meaning as understood by a person of ordinary skill in the art, and is used without limitation to refer to the transcription and stable accumulation of sense (mRNA) or antisense RNA derived from the nucleic acid fragment of the subject technology. "Overexpression" refers to the production of a gene product in transgenic or recombinant organisms that exceeds levels of production in normal or non-transformed organisms.

"Transformation" is used according to its ordinary and customary meaning as understood by a person of ordinary skill in the art, and is used without limitation to refer to the transfer of a polynucleotide into a target cell. The transferred polynucleotide can be incorporated into the genome or chromosomal DNA of a target cell, resulting in genetically stable inheritance, or it can replicate independent of the host chromosomal. Host organisms containing the transformed nucleic acid fragments are referred to as "transgenic" or "recombinant" or "transformed" organisms.

The terms "transformed," "transgenic," and "recombinant," when used herein in connection with host cells, are used according to their ordinary and customary meanings as understood by a person of ordinary skill in the art, and are used without limitation to refer to a cell of a host organism, such as a plant or microbial cell, into which a heterologous nucleic acid molecule has been introduced. The nucleic acid molecule can be stably integrated into the genome of the host cell, or the nucleic acid molecule can be present as an extrachromosomal molecule. Such an extrachromosomal molecule can be auto-replicating. Transformed cells, tissues, or subjects are understood to encompass not only the end product of a transformation process, but also transgenic progeny thereof.

The terms "recombinant," "heterologous," and "exogenous," when used herein in connection with polynucleotides, are used according to their ordinary and customary meanings as understood by a person of ordinary skill in the art, and are used without limitation to refer to a polynucleotide (e.g., a DNA sequence or a gene) that originates from a source foreign to the particular host cell or, if from the same source, is modified from its original form. Thus, a heterologous gene in a host cell includes a gene that is endogenous to the particular host cell but has been modified through, for example, the use of site-directed mutagenesis or other recombinant techniques. The terms also include non-naturally occurring multiple copies of a naturally occurring DNA sequence. Thus, the terms refer to a DNA segment that is foreign or heterologous to the cell, or homologous to the cell but in a position or form within the host cell in which the element is not ordinarily found.

Similarly, the terms "recombinant," "heterologous," and "exogenous," when used herein in connection with a polypeptide or amino acid sequence, means a polypeptide or amino acid sequence that originates from a source foreign to the particular host cell or, if from the same source, is modified from its original form. Thus, recombinant DNA segments can be expressed in a host cell to produce a recombinant polypeptide.

The terms "plasmid," "vector," and "cassette" are used according to their ordinary and customary meanings as understood by a person of ordinary skill in the art, and are used without limitation to refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used herein are well known in the art and are described, for example, by Sambrook, J., Fritsch, E. F. and Maniatis, T. Molecular Cloning: A Laboratory Manual, $2^{nd}$ ed.; Cold Spring Harbor Laboratory: Cold Spring Harbor, N.Y., 1989 (hereinafter "Maniatis"); and by Silhavy, T. J., Bennan, M. L. and Enquist, L. W. Experiments with Gene Fusions; Cold Spring Harbor Laboratory: Cold Spring Harbor, N.Y., 1984; and by Ausubel, F. M. et al., In Current Protocols in Molecular Biology, published by Greene Publishing and Wiley-Interscience, 1987; the entireties of each of which are hereby incorporated herein by reference to the extent they are consistent herewith.

As used herein, "synthetic" or "organically synthesized" or "chemically synthesized" or "organically synthesizing" or "chemically synthesizing" or "organic synthesis" or "chemical synthesis" are used to refer to preparing the compounds through a series of chemical reactions; this does not include extracting the compound, for example, from a natural source.

The term "orally consumable product" as used herein refers to any beverage, food product, dietary supplement, nutraceutical, pharmaceutical composition, dental hygienic composition and cosmetic product which are contacted with the mouth of man or animal, including substances that are taken into and subsequently ejected from the mouth and substances which are drunk, eaten, swallowed, or otherwise ingested; and that are safe for human or animal consumption when used in a generally acceptable range of concentrations.

The term "food product" as used herein refers to fruits, vegetables, juices, meat products such as ham, bacon and sausage; egg products, fruit concentrates, gelatins and gelatin-like products such as jams, jellies, preserves, and the like; milk products such as ice cream, sour cream, yogurt, and sherbet; icings, syrups including molasses; corn, wheat, rye, soybean, oat, rice and barley products, cereal products, nut meats and nut products, cakes, cookies, confectionaries such as candies, gums, fruit flavored drops, and chocolates, chewing gum, mints, creams, icing, ice cream, pies and breads. "Food product" also refers to condiments such as herbs, spices and seasonings, flavor enhancers, such as monosodium glutamate. "Food product" further refers to also includes prepared packaged products, such as dietetic sweeteners, liquid sweeteners, tabletop flavorings, granulated flavor mixes which upon reconstitution with water provide non-carbonated drinks, instant pudding mixes, instant coffee and tea, coffee whiteners, malted milk mixes, pet foods, livestock feed, tobacco, and materials for baking applications, such as powdered baking mixes for the preparation of breads, cookies, cakes, pancakes, donuts and the like. "Food product" also refers to diet or low-calorie food and beverages containing little or no sucrose.

As used herein, the term "stereoisomer" is a general term for all isomers of individual molecules that differ only in the orientation of their atoms in space. "Stereoisomer" includes enantiomers and isomers of compounds with more than one chiral center that are not mirror images of one another (diastereomers).

As used herein, the term "amorphous rebaudioside V" refers to a non-crystalline solid form of rebaudioside V. As used herein, the term "amorphous rebaudioside W" refers to a non-crystalline solid form of rebaudioside W.

As used herein, the term "sweetness intensity" refers to the relative strength of sweet sensation as observed or experienced by an individual, e.g., a human, or a degree or amount of sweetness detected by a taster, for example on a Brix scale.

As used herein, the term "enhancing the sweetness" refers to the effect of rebaudioside V and/or rebaudioside W in increasing, augmenting, intensifying, accentuating, magnifying, and/or potentiating the sensory perception of one or more sweetness characteristics of a beverage product or a consumable product of the present disclosure without changing the nature or quality thereof, as compared to a corresponding orally consumable product that does not contain rebaudioside V and/or rebaudioside W.

As used herein, the term "off-taste(s)" refers to an amount or degree of taste that is not characteristically or usually found in a beverage product or a consumable product of the present disclosure. For example, an off-taste is an undesirable taste of a sweetened consumable to consumers, such as, a bitter taste, a licorice-like taste, a metallic taste, an aversive taste, an astringent taste, a delayed sweetness onset, a lingering sweet aftertaste, and the like, etc.

As used herein, the term "w/v-%" refers to the weight of a compound, such as a sugar, (in grams) for every 100 ml of a liquid orally consumable product of the present disclosure containing such compound. As used herein, the term "w/w-%" refers to the weight of a compound, such as a sugar, (in grams) for every gram of an orally consumable product of the present disclosure containing such compound.

As used herein, the term "ppm" refers to part(s) per million by weight, for example, the weight of a compound, such as rebaudioside V and/or rebaudioside W (in milligrams) per kilogram of an orally consumable product of the present disclosure containing such compound (i.e., mg/kg) or the weight of a compound, such as rebaudioside V and/or rebaudioside W (in milligrams) per liter of an orally consumable product of the present disclosure containing such compound (i.e., mg/L); or by volume, for example the volume of a compound, such as rebaudioside V and/or rebaudioside W (in milliliters) per liter of an orally consumable product of the present disclosure containing such compound (i.e., ml/L).

In accordance with the present disclosure, non-caloric sweeteners and methods for synthesizing the non-caloric sweeteners are disclosed. Also in accordance with the present disclosure an enzyme and methods of using the enzyme to prepare the non-caloric sweeteners are disclosed.

Synthetic Non-Caloric Sweeteners: Synthetic Rebaudioside V

In one aspect, the present disclosure is directed to a synthetic non-caloric sweetener. The synthetic non-caloric sweetener is a synthetic rebaudioside-type steviol glycoside and has been given the name, "Rebaudioside V". Rebaudioside V ("Reb V") is a steviol glycoside having four β-D-glucosyl units in its structure connected to the aglycone steviol, a steviol aglycone moiety with a Glc β1-3-Glc β1 unit at C-13 in the form of ether linkage and another Glc β1-2-Glc β1 unit at C-19 position in the form of an ester linkage.

Rebaudioside V has the molecular formula $C_{44}H_{70}O_{23}$ and the IUPAC name, 13-[(3-O-β-D-glucopyranosyl-β-D-glucopyranosyl)oxy] ent-kaur-16-en-19-oic acid-(2-O-β-D-glucopyranosyl-β-D-glucopyranosyl) ester on the basis of extensive 1D and 2D NMR as well as high resolution mass spectral data and hydrolysis studies.

Synthetic Non-Caloric Sweeteners: Synthetic Rebaudioside W

In one aspect, the present disclosure is directed to a synthetic non-caloric sweetener. The synthetic non-caloric sweetener is a synthetic rebaudioside-type steviol glycoside and has been given the name, "Rebaudioside W". Rebaudioside W ("Reb W") is a steviol glycoside having five β-D-glucosyl units in its structure connected to the aglycone steviol, a steviol aglycone moiety with a Glc β1-3-Glc β1 unit at C-13 in the form of ether linkage and a Glc β1-2(Glc β1-3)-Glc β1 unit at C-19 position in the form of an ester linkage.

Rebaudioside W has the molecular formula $C_5H_{80}O_{28}$ and the IUPAC name, 13-[(3-O-β-D-glucopyranosyl-β-D-glucopyranosyl)oxy] ent-kaur-16-en-19-oic acid-[(2-O-β-D-glucopyranosyl-3-O-β-D-glucopyranosyl-β-D-glucopyranosyl) ester.

Synthetic Non-Caloric Sweeteners: Synthetic Rebaudioside KA

In one aspect, the present disclosure is directed to a synthetic non-caloric sweetener. The synthetic non-caloric sweetener is a synthetic rebaudioside-type steviol glycoside and has been given the name, "Rebaudioside KA". Rebaudioside KA ("Reb KA") is a steviol glycoside having three β-D-glucosyl units in its structure connected to the aglycone steviol, a steviol aglycone moiety with a Glc β1 unit at C-13 in the form of ether linkage and a Glc β1-2-Glc β1 unit at C-19 in the form of ether linkage. Rebaudioside KA has the molecular formula $C_{38}H_{60}O_{18}$ and the IUPAC name, 13-β-D-glucopyranosyloxy] ent-kaur-16-en-19-oic acid-(2-O-β-D-glucopyranosyl-β-D-glucopyranosyl) ester on the basis of extensive 1D and 2D NMR as well as high resolution mass spectral data and hydrolysis studies.

Synthetic Non-Caloric Sweeteners: Synthetic Rebaudioside G

In one aspect, the present disclosure is directed to a synthetic non-caloric sweetener. The synthetic non-caloric sweetener is a synthetic rebaudioside-type steviol glycoside and has been given the name, "Rebaudioside G". Rebaudioside G ("Reb G") is a steviol glycoside having three β-D-glucosyl units in its structure connected to the aglycone steviol, a steviol aglycone moiety with a Glc β1-3-Glc β1 unit at C-13 in the form of ether linkage and a Glc β1 unit at C-19 in the form of ether linkage.

Rebaudioside G has the molecular formula $C_{38}H_{60}O_{18}$ and the IUPAC name, 13-[(3-O-β-D-glucopyranosyl-β-D-glucopyranosyl)oxy] ent-kaur-16-en-19-oic acid-β-D-glucopyranosyl) ester on the basis of extensive 1D and 2D NMR as well as high resolution mass spectral data and hydrolysis studies.

Synthetic Non-Caloric Sweeteners: Synthetic Rebaudioside M

In one aspect, the present disclosure is directed to a synthetic non-caloric sweetener. The synthetic non-caloric sweetener is a synthetic rebaudioside-type steviol glycoside and has been given the name, "Rebaudioside M". Rebaudioside M ("Reb M") is a steviol glycoside having six β-D-glucosyl units in its structure connected to the aglycone steviol, a steviol aglycone moiety with a Glc β1-2(Glc β1-3)-Glc β1 unit at the C-13 position in the form of an ether linkage and a Glc β1-2(Glc β1-3)-Glc β1 unit at the C-19 position in the form of an ester linkage.

Rebaudioside M has the molecular formula $C_{56}H_{90}O_{33}$ and the IUPAC name, 13-[(2-O-β-D-glucopyranosyl-3-O-β-D-glucopyranosyl-β-D-glucopyranosyl)oxy] ent-kaur-16-en-19-oic acid-[(2-O-β-D-glucopyranosyl-3-O-β-D-glucopyranosyl-β-D-glucopyranosyl)ester on the basis of extensive 1D and 2D NMR as well as high resolution mass spectral data and hydrolysis studies.

Methods of Synthesizing Steviol Glycosides

Method of Producing Rebaudioside V from Rebaudioside G.

In another aspect, the present disclosure is directed to a method for synthesizing rebaudioside V from rebaudioside G. The method comprises preparing a reaction mixture comprising rebaudioside G; substrates selected from the group consisting of sucrose, uridine diphosphate (UDP) and uridine diphosphate-glucose (UDP-glucose); and a HV1 UDP-glycosyltransferase; with or without sucrose synthase (SUS) and incubating the reaction mixture for a sufficient time to produce rebaudioside V, wherein a glucose is covalently coupled to the rebaudioside G to produce rebaudioside V.

Method of Producing Rebaudioside V from Rebaudioside G.

In another aspect, the present disclosure is directed to a method for synthesizing rebaudioside V from rebaudioside G. The method comprises preparing a reaction mixture comprising rebaudioside G; substrates selected from the group consisting of sucrose, uridine diphosphate (UDP) and uridine diphosphate-glucose (UDP-glucose); a uridine diposphoglycosyltransferase (UDP-glycosyltransferase) selected from the group consisting of an EUGT11, a UDP-glycosyltransferase-Sucrose synthase (SUS) fusion enzyme; with or without sucrose synthase (SUS) and incubating the reaction mixture for a sufficient time to produce rebaudioside V, wherein a glucose is covalently coupled to the rebaudioside G to produce rebaudioside V.

Method of producing Rebaudioside V from Rebaudioside KA.

In another aspect, the present disclosure is directed to a method for synthesizing rebaudioside V from rebaudioside KA. The method comprises preparing a reaction mixture comprising rebaudioside KA; substrates selected from the group consisting of sucrose, uridine diphosphate (UDP) and uridine diphosphate-glucose (UDP-glucose); a uridine dipospho glycosyltransferases (UDP-glycosyltransferase) selected from the group consisting of a UDP-glycosyltransferase (UGT76G1) and a UDP-glycosyltransferase-Sucrose synthase fusion enzyme; with or without sucrose synthase (SUS) and incubating the reaction mixture for a sufficient time to produce rebaudioside V, wherein a glucose is covalently coupled to the rebaudioside KA to produce rebaudioside V.

Method of Producing Rebaudioside V from Rubusoside.

In another aspect, the present disclosure is directed to a method for synthesizing rebaudioside V from rubusoside. The method comprises preparing a reaction mixture comprising rubusoside; substrates selected from the group consisting of sucrose, uridine diphosphate (UDP) and uridine diphosphate-glucose (UDP-glucose); uridine dipospho glycosyltransferase(s) (UDP-glycosyltransferase) selected from the group consisting of a UDP-glycosyltransferase (UGT76G1), HV1 and a UDP-glycosyltransferase-Sucrose synthase fusion enzyme; with or without sucrose synthase (SUS) and incubating the reaction mixture for a sufficient time to produce rebaudioside V, wherein a glucose is covalently coupled to the rubusoside to produce rebaudioside KA. Continually, a glucose is covalently coupled to the rebaudioside KA to produce rebaudioside V.

Method of Producing of Rebaudioside V from Rubusoside.

In another aspect, the present disclosure is directed to a method for synthesizing a mixture of rebaudioside A and rebaudioside V from rubusoside. The method comprises preparing a reaction mixture comprising rubusoside; substrates selected from the group consisting of sucrose, uridine diphosphate (UDP) and uridine diphosphate-glucose (UDP-glucose); uridine dipospho glycosyltransferase(s) (UDP-glycosyltransferase) selected from the group consisting of a UDP-glycosyltransferase (UGT76G1), EUGT11 and a UDP-glycosyltransferase-Sucrose synthase fusion enzyme; with or without sucrose synthase; and incubating the reaction mixture for a sufficient time to produce rebaudioside V, wherein a glucose is covalently coupled to the rubusoside to produce rebaudioside KA and a glucose is covalently coupled to the rebaudioside KA to produce rebaudioside V. A glucose is covalently coupled to the rubusoside to produce rebaudioside G. Continually, a glucose is covalently coupled to the rebaudioside G to produce rebaudioside V.

Method of producing Rebaudioside W from Rebaudioside V.

In another aspect, the present disclosure is directed to a method for synthesizing rebaudioside W from rebaudioside V. The method comprises preparing a reaction mixture comprising rebaudioside V; substrates selected from the group consisting of sucrose, uridine diphosphate (UDP) and uridine diphosphate-glucose (UDP-glucose); an uridine dipospho glycosyltransferase (UDP-glycosyltransferase) selected from the group consisting of a UDP-glycosyltransferase (UGT76G1) and a UDP-glycosyltransferase-Sucrose synthase fusion enzyme; with or without sucrose synthase and incubating the reaction mixture for a sufficient time to produce rebaudioside W, wherein a glucose is covalently coupled to the rebaudioside V to produce rebaudioside W.

Method of Producing Rebaudioside W from Rebaudioside G.

In another aspect, the present disclosure is directed to a method for synthesizing rebaudioside W from rebaudioside G. The method comprises preparing a reaction mixture comprising rebaudioside G; substrates selected from the group consisting of sucrose, uridine diphosphate (UDP) and uridine diphosphate-glucose (UDP-glucose); an uridine dipospho glycosyltransferase (UDP-glycosyltransferase) selected from the group consisting of a uridine diphospho glycosyltransferase (UGT76G1), a UDP-glycosyltransferase-Sucrose synthase fusion enzyme and a HV1; with or without sucrose synthase; and incubating the reaction mixture for a sufficient time to produce rebaudioside W, wherein a glucose is covalently coupled to the rebaudioside G to produce rebaudioside V by HV1. Continually, a glucose is covalently coupled to the rebaudioside V to produce rebaudioside W by UGT76G1.

Method of Producing Rebaudioside W from Rebaudioside G.

In another aspect, the present disclosure is directed to a method for synthesizing rebaudioside W from rebaudioside G. The method comprises preparing a reaction mixture comprising rebaudioside G; substrates selected from the group consisting of sucrose, uridine diphosphate (UDP) and uridine diphosphate-glucose (UDP-glucose); an uridine diphospho glycosyltransferase (UDP-glycosyltransferase) selected from the group consisting of a UGT76G1, an EUGT11, and a UDP-glycosyltransferase-Sucrose synthase fusion enzyme; and incubating the reaction mixture for a sufficient time to produce rebaudioside W, wherein a glucose is covalently coupled to the rebaudioside G to produce rebaudioside V by EUGT11. Continually, a glucose is covalently coupled to the rebaudioside V to produce rebaudioside W by UGT76G1.

Method of Producing Rebaudioside W from Rebaudioside KA.

In another aspect, the present disclosure is directed to a method for synthesizing rebaudioside W from rebaudioside KA. The method comprises preparing a reaction mixture comprising rebaudioside KA; substrates selected from the group consisting of sucrose, uridine diphosphate (UDP) and uridine diphosphate-glucose (UDP-glucose); an uridine dipospho glycosyltransferase (UDP-glycosyltransferase) selected from the group consisting of a uridine diphospho glycosyltransferase (UGT76G1), and a UDP-glycosyltransferase-Sucrose synthase fusion enzyme; with or without sucrose synthase; and incubating the reaction mixture for a sufficient time to produce rebaudioside W, wherein a glucose is covalently coupled to the rebaudioside KA to produce rebaudioside V. Continually, a glucose is covalently coupled to the rebaudioside V to produce rebaudioside W.

Method of Producing of Rebaudioside W from Rubusoside.

In another aspect, the present disclosure is directed to a method for synthesizing rebaudioside W from rubusoside. The method comprises preparing a reaction mixture comprising rubusoside; substrates selected from the group consisting of sucrose, uridine diphosphate (UDP) and uridine diphosphate-glucose (UDP-glucose); uridine diphospho glycosyltransferases selected from the group consisting of a UGT76G1, an HV1, and a UDP-glycosyltransferase-Sucrose synthase fusion enzyme; with or without sucrose synthase and incubating the reaction mixture for a sufficient time to produce a mixture of rebaudioside W.

Method of Producing of Rebaudioside W from Rubusoside.

In another aspect, the present disclosure is directed to a method for synthesizing rebaudioside W from rubusoside. The method comprises preparing a reaction mixture comprising rubusoside; substrates selected from the group consisting of sucrose, uridine diphosphate (UDP) and uridine diphosphate-glucose (UDP-glucose); uridine diphospho glycosyltransferases selected from the group consisting of a UGT76G1, an EUGT11, and a UDP-glycosyltransferase-Sucrose synthase fusion enzyme; with or without sucrose synthase and incubating the reaction mixture for a sufficient time to produce rebaudioside W.

Method of Producing a Mixture of Stevioside and Rebaudioside KA from Rubusoside.

In another aspect, the present disclosure is directed to a method for synthesizing a mixture of stevioside and rebaudioside KA from rubusoside. The method comprises preparing a reaction mixture comprising rubusoside; substrates selected from the group consisting of sucrose, uridine diphosphate (UDP) and uridine diphosphate-glucose (UDP-glucose); a UDP-glycosyltransferase selected from the group consisting of EUGT11 and a UDP-glycosyltransferase-Sucrose synthase fusion enzyme; with or without sucrose synthase; and incubating the reaction mixture for a sufficient time to produce a mixture of stevioside and rebaudioside KA, wherein a glucose is covalently coupled to C2'-19-O-glucose of rubusoside to produce rebaudioside KA; a glucose is convalently coupled to C2'-13-O-glucose of rubusoside to produce stevioside.

Method of Producing Rebaudioside KA from Rubusoside.

In another aspect, the present disclosure is directed to a method for synthesizing a rebaudioside KA from rubusoside. The method comprises preparing a reaction mixture comprising rubusoside; substrates selected from the group consisting of sucrose, uridine diphosphate (UDP) and uridine diphosphate-glucose (UDP-glucose); and HV1 UDP-glycosyltransferase; with or without sucrose synthase; and incubating the reaction mixture for a sufficient time to produce rebaudioside KA, wherein a glucose is covalently coupled to the C2'-19-O-glucose of rubusoside to produce a rebaudioside KA.

Method of Producing Rebaudioside G from Rubusoside.

In another aspect, the present disclosure is directed to a method for synthesizing a rebaudioside G from rubusoside. The method comprises preparing a reaction mixture comprising rubusoside; substrates selected from the group consisting of sucrose, uridine diphosphate (UDP) and uridine diphosphate-glucose (UDP-glucose); a UDP-glycosyltransferase selected from the group consisting of UGT76G1 and a UDP-glycosyltransferase-Sucrose synthase fusion enzyme; with or without sucrose synthase; and incubating the reaction mixture for a sufficient time to produce rebaudioside G, wherein a glucose is covalently coupled to the C3'-13-O-glucose of rubusoside to produce a rebaudioside G.

Method of Producing Rebaudioside E from Rebaudioside KA.

In another aspect, the present disclosure is directed to a method for synthesizing rebaudioside E from rebaudioside KA. The method comprises preparing a reaction mixture comprising rebaudioside KA; substrates selected from the group consisting of sucrose, uridine diphosphate (UDP) and uridine diphosphate-glucose (UDP-glucose); and HV1 UDP-glycosyltransferase; with or without sucrose synthase; and incubating the reaction mixture for a sufficient time to produce rebaudioside E, wherein a glucose is covalently coupled to the C2' 13-O-glucose of rebaudioside KA to produce rebaudioside E.

Method of Producing Rebaudioside E from Rebaudioside KA.

In another aspect, the present disclosure is directed to a method for synthesizing rebaudioside E from rebaudioside KA. The method comprises preparing a reaction mixture comprising rebaudioside KA; substrates selected from the group consisting of sucrose, uridine diphosphate (UDP) and uridine diphosphate-glucose (UDP-glucose); a UDP-glycosyltransferase from a group of EUGT11 and a UDP-glycosyltransferase-Sucrose synthase fusion enzyme; with or without sucrose synthase; and incubating the reaction mixture for a sufficient time to produce rebaudioside E, wherein a glucose is covalently coupled to the C2' 13-O-glucose of rebaudioside KA to produce rebaudioside E.

Method of Producing Rebaudioside E from Rubusoside.

In another aspect, the present disclosure is directed to a method for synthesizing rebaudioside E from rubusoside. The method comprises preparing a reaction mixture comprising rubusoside; a substrate selected from the group consisting of sucrose, uridine diphosphate (UDP) and uridine diphosphate-glucose (UDP-glucose); and a UDP-glycosyltransferase from the group of EUGT11 and a UDP-glycosyltransferase-Sucrose synthesis fusion enzyme; with or without sucrose synthase; incubating the reaction mixture for a sufficient time to produce rebaudioside E, wherein a glucose is covalently coupled to rubusoside to produce a mixture of rebaudioside KA and stevioside. Continually, a glucose is covalently coupled to rebaudioside KA and stevioside to produce rebaudioside E.

Method of Producing Rebaudioside E from Rubusoside.

In another aspect, the present disclosure is directed to a method for synthesizing rebaudioside E from rubusoside. The method comprises preparing a reaction mixture comprising rubusoside; substrates selected from the group consisting of sucrose, uridine diphosphate (UDP) and uridine diphosphate-glucose (UDP-glucose); and HV1 UDP-glycosyltransferase; with or without sucrose synthase; incubating the reaction mixture for a sufficient time to produce rebaudioside E, wherein a glucose is covalently coupled to the rubusoside to produce rebaudioside KA; and further incubating the rebaudioside KA with HV1 to produce rebaudioside E.

Method of Producing Rebaudioside D3 from Rubusoside.

In another aspect, the present disclosure is directed to a method for synthesizing rebaudioside D3 from rubusoside. The method comprises preparing a reaction mixture comprising rubusoside; substrates selected from the group consisting of sucrose, uridine diphosphate (UDP) and uridine diphosphate-glucose (UDP-glucose); a UDP-glycosyltransferase from the group of EUGT11 and a UDP-glycosyltransferase-Sucrose synthesis fusion enzyme; with or without sucrose synthase; incubating the reaction mixture for a sufficient time to produce rebaudioside D3, wherein a glucose is covalently coupled to the rubusoside to produce a mixture of stevioside and rebaudioside KA; further incubating the mixture of stevioside and rebaudioside KA with EUGT11 to produce rebaudioside E, wherein a glucose is covalently coupled to the stevioside and the rebaudioside KA to produce rebaudioside E; and further incubating the rebaudioside E with EUGT11 to produce rebaudioside D3, wherein a glucose is covalently coupled to the rebaudioside E to produce rebaudioside D3.

Method of Producing Rebaudioside D3 from Rebaudioside KA.

In another aspect, the present disclosure is directed to a method for synthesizing rebaudioside D3 from rebaudioside KA. The method includes preparing a reaction mixture comprising rebaudioside KA, substrates selected from the group consisting of sucrose, uridine diphosphate (UDP) and uridine diphosphate-glucose (UDP-glucose), a UDP-glycosyltransferase selected from the group consisting of an EUGT11 and a UDP-glycosyltransferase-Sucrose synthase fusion enzyme, with or without sucrose synthase; incubating the reaction mixture for a sufficient time to produce rebaudioside D3, wherein a glucose is covalently coupled to the rebaudioside KA to produce rebaudioside E; further incubating the mixture of rebaudioside E with EUGT11 to produce rebaudioside D3, wherein a glucose is covalently coupled to the rebaudioside E to produce rebaudioside D3.

Method of Producing Rebaudioside Z from Rebaudioside E.

In another aspect, the present disclosure is directed to a method for synthesizing rebaudioside Z from rebaudioside E. The method comprises preparing a reaction mixture comprising rebaudioside E; substrates selected from the group consisting of sucrose, uridine diphosphate (UDP) and uridine diphosphate-glucose (UDP-glucose); and HV1 UDP-glycosyltransferase; and sucrose synthase, incubating the reaction mixture for a sufficient time to produce rebaudioside Z, wherein a glucose is covalently coupled to the rebaudioside E to produce rebaudioside Z, wherein a glucose is covalently coupled to the C2'-13-O-glucose of rebaudioside E to produce rebaudioside Z1. A glucose is convalently coupled to C2'-19-O-glucose of rebaudioside E to produce rebaudioside Z2.

Method of Producing Rebaudioside M from Rebaudioside D.

In another aspect, the present disclosure is directed to a method for synthesizing rebaudioside M from rebaudioside D. The method includes preparing a reaction mixture comprising rebaudioside D, substrates selected from the group consisting of sucrose, uridine diphosphate (UDP), uridine diphosphate-glucose (UDP-glucose), and combinations thereof, and a UDP-glycosyltransferase selected from the group consisting of UGT76G1, a UDP-glycosyltransferase-Sucrose synthase fusion enzyme, and combinations thereof, with or without sucrose synthase; and incubating the reaction mixture for a sufficient time to produce rebaudioside M, wherein a glucose is covalently coupled to the rebaudioside D to produce rebaudioside M.

Method of Producing Rebaudioside D and Rebaudioside M from Stevioside.

In another aspect, the present disclosure is directed to a method for synthesizing rebaudioside D and rebaudioside M from stevioside. The method includes preparing a reaction mixture comprising stevioside, substrates selected from the group consisting of sucrose, uridine diphosphate (UDP), uridine diphosphate-glucose (UDP-glucose), and combinations thereof, and a UDP-glycosyltransferase selected from the group consisting of HV1, UGT76G1, a UDP-glycosyltransferase-Sucrose synthase fusion enzyme, and combinations thereof, with or without sucrose synthase; and incubating the reaction mixture for a sufficient time to produce rebaudioside D and/or rebaudioside M. For instance, in embodiments, the reaction mixture may be incubated for a sufficient time to produce rebaudioside D, and the reaction mixture comprising rebaudioside D further incubated (e.g., with UGT76G1 and/or the fusion enzyme) to produce rebaudioside M. In certain embodiments, the reaction mixture will comprise HV1 and UGT76G1. In other embodiments, the reaction mixture will comprise HV1 and the fusion enzyme.

In certain embodiments, a glucose is covalently coupled to the stevioside to produce rebaudioside A and/or rebaudioside E. For example, a glucose may be covalently coupled to the stevioside by UGT76G1 or the fusion enzyme to produce rebaudioside A and/or a glucose may be covalently coupled to the stevioside by HV1 to produce rebaudioside E. Continually, a glucose may be covalently coupled to the rebaudioside A by HV1 to produce rebaudioside D and/or a glucose may be covalently coupled to the rebaudioside E by UGT76G1 or the fusion enzyme to produce rebaudioside D. A glucose may further be covalently coupled to the rebaudioside D by UGT76G1 or the fusion enzyme to produce rebaudioside M.

Method of Producing Rebaudioside D and Rebaudioside M from Rebaudioside A.

In another aspect, the present disclosure is directed to a method for synthesizing rebaudioside D and rebaudioside M from rebaudioside A. The method includes preparing a reaction mixture comprising rebaudioside A, substrates selected from the group consisting of sucrose, uridine diphosphate (UDP), uridine diphosphate-glucose (UDP-glucose), and combinations thereof, and a UDP-glycosyltransferase selected from the group consisting of HV1, UGT76G1, a UDP-glycosyltransferase-Sucrose synthase fusion enzyme, and combinations thereof, with or without sucrose synthase; and incubating the reaction mixture for a sufficient time to produce rebaudioside D and/or rebaudioside M. For instance, in embodiments, the reaction mixture (e.g., comprising HV1) may be incubated for a sufficient time to produce rebaudioside D, and the reaction mixture comprising rebaudioside D further incubated (e.g., with UGT76G1 and/or the fusion enzyme) to produce rebaudioside M. In certain embodiments, the reaction mixture will comprise HV1 and UGT76G1. In other embodiments, the reaction mixture will comprise HV1 and the fusion enzyme.

A glucose is covalently coupled to the rebaudioside A to produce rebaudioside D. For example, a glucose may be covalently coupled to the rebaudioside A by HV1 to produce rebaudioside D. Continually, a glucose may be covalently coupled to the rebaudioside D by UGT76G1 or the fusion enzyme to produce rebaudioside M.

Method of Producing Rebaudioside D and Rebaudioside M from Rebaudioside E.

In another aspect, the present disclosure is directed to a method for synthesizing rebaudioside D and rebaudioside M from rebaudioside E. The method includes preparing a reaction mixture comprising rebaudioside E, substrates selected from the group consisting of sucrose, uridine diphosphate (UDP), uridine diphosphate-glucose (UDP-glucose), and combinations thereof, and a UDP-glycosyltransferase selected from the group consisting of an UGT76G1, a UDP-glycosyltransferase-Sucrose synthase fusion enzyme, and combinations thereof, with or without sucrose synthase; and incubating the reaction mixture for a sufficient time to produce rebaudioside D and/or rebaudioside M. For instance, in embodiments, the reaction mixture (e.g., comprising UGT76G1 and/or the fusion enzyme) may be incubated for a sufficient time to produce rebaudioside D, and the reaction mixture comprising rebaudioside D further incubated to produce rebaudioside M.

A glucose is covalently coupled to the rebaudioside E to produce rebaudioside D. For example, a glucose may be covalently coupled to the rebaudioside E by UGT76G1 or the fusion enzyme to produce rebaudioside D. Continually, a glucose may be covalently coupled to the rebaudioside D by UGT76G1 or the fusion enzyme to produce rebaudioside M.

The majority of the steviol glycosides are formed by several glycosylation reactions of steviol, which typically are catalyzed by the UDP-glycosyltransferases (UGTs) using uridine 5'-diphosphoglucose (UDP-glucose) as a donor of the sugar moiety. In plants, UGTs are a very divergent group of enzymes that transfer a glucose residue from UDP-glucose to steviol.

Uridine diphospho glycosyltransferase (UGT76G1) is a UGT with a 1,3-13-O-glucose glycosylation activity to produce related glycoside (rebaudioside A and D). Surprisingly and unexpectedly, it was discovered that UGT76G1 also has 1,3-19-O-glucose glycosylation activity to produce rebaudioside G from rubusoside, and to produce rebaudioside M from rebaudioside D. UGT76G1 can convert rebaudioside KA to Reb V and continue to form Reb W. A particularly suitable UGT76G1 has an amino acid sequence of SEQ ID NO:1.

EUGT11 (described in WO 2013022989) is a UGT having 1,2-19-O-glucose and 1,2-13-O-glucose glycosylation activity. EUGT11 is known to catalyze the production of stevioside to rebaudioside E and rebaudioside A to rebaudioside D. Surprisingly and unexpectedly, it was discovered that EUGT11 can be used in vitro to synthesize rebaudioside D3 from rebaudioside E by a new enzyme activity (β1,6-13-O-glucose glycosylation activity) (U.S. patent application Ser. No. 14/269,435, assigned to Conagen, Inc.). EUGT11 has 1,2-19-O-glucose glycosylation activity to produce rebaudioside KA from rubusoside. A particularly suitable EUGT11 has the amino acid sequence of SEQ ID NO:3.

HV1 is a UGT with a 1,2-19-O-glucose glycosylation activity to produce related steviol glycosides (rebaudioside E, D and Z). Surprisingly and unexpectedly, it was discovered that HV1 also has 1,2-19-O-glucose glycosylation activity to produce rebaudioside KA from rubusoside. HV1 also can convert Reb G to Reb V and Reb KA to Reb E. A particularly suitable HV1 has the amino acid sequence of SEQ ID NO:5.

The method can further include adding a sucrose synthase to the reaction mixture that contains the uridine diphospho (UDP) glycosyltransferase. Sucrose synthase catalyzes the chemical reaction between NDP-glucose and D-fructose to produce NDP and sucrose. Sucrose synthase is a glycosyltransferase. The systematic name of this enzyme class is NDP-glucose:D-fructose 2-alpha-D-glucosyltransferase. Other names in common use include UDP glucose-fructose glucosyltransferase, sucrose synthetase, sucrose-UDP glucosyltransferase, sucrose-uridine diphosphate glucosyltransferase, and uridine diphosphoglucose-fructose glucosyltransferase. Addition of the sucrose synthase to the reaction mixture that includes a uridine diphospho glycosyltransferase creates a "UGT-SUS coupling system". In the UGT-SUS coupling system, UDP-glucose can be regenerated from UDP and sucrose, which allows for omitting the addition of extra UDP-glucose to the reaction mixture or using UDP in the reaction mixture. Suitable sucrose synthases can be for example, an *Arabidopsis* sucrose synthase 1; an *Arabidopsis* sucrose synthase 3; and a *Vigna radiate* sucrose synthase. A particularly suitable sucrose synthase can be, for example, *Arabidopsis* sucrose synthase 1. A particularly suitable *Arabidopsis* sucrose synthase 1 is *Arabidopsis thaliana* sucrose synthase 1 (AtSUS1), having the amino acid sequence of SEQ ID NO:7.

In another aspect, uridine dipospho glycosyltransferase fusion enzyme can be used in the methods. A particularly suitable uridine dipospho glycosyltransferase fusion enzyme can be a UGT-SUS1 fusion enzyme. The UDP-glycosyltransferase can be a UDP-glycosyltransferase fusion enzyme that includes a uridine diphospho glycosyltransferase domain coupled to a sucrose synthase domain. In particular, the UDP-glycosyltransferase fusion enzyme includes a uridine diphospho glycosyltransferase domain coupled to a sucrose synthase domain. Additionally, the UGT-SUS1 fusion enzyme has sucrose synthase activity, and thus, can regenerate UDP-glucose from UDP and sucrose. A particularly suitable UGT-SUS 1 fusion enzyme can be, for example, a UGT76G1-AtSUS1 fusion enzyme (named as: "GS") having the amino acid sequence of SEQ ID NO:9. Another particularly suitable UGT-SUS1 fusion enzyme can be, for example, a EUGT11-SUS1 (named as: "EUS") having the amino acid sequence of SEQ ID NO:11.

Suitable sucrose synthase domains can be for example, an *Arabidopsis* sucrose synthase 1; an *Arabidopsis* sucrose synthase 3; and a *Vigna radiate* sucrose synthase. A particularly suitable sucrose synthase domain can be, for example, *Arabidopsis* sucrose synthase 1. A particularly suitable *Arabidopsis* sucrose synthase 1 is *Arabidopsis thaliana* sucrose synthase 1 (AtSUS1), having the amino acid sequence of SEQ ID NO:7.

The UGT76G1-AtSUS1 ("GS") fusion enzyme can have a polypeptide sequence with at least 70%, at least 80%, at least 85%, at least 90%, at least 91%, at least 92%, at least 93%, at least 94%, at least 95%, at least 96%, at least 97%, at least 98%, at least 99% and even 100% identical to the amino acid sequence set forth in SEQ ID NO:9. Suitably, the amino acid sequence of the UGT-AtSUS1 fusion enzyme has at least 80% identity to SEQ ID NO:9. More suitably, the amino acid sequence of the UGT-AtSUS1 fusion enzyme has at least 85%, at least 90%, at least 91%, at least 92%, at least 93%, at least 94%, at least 95%, at least 96%, at least 97%, at least 98%, at least 99%, and even 100% amino acid sequence identity to the amino acid sequence set forth in SEQ ID NO:9.

The isolated nucleic acid can include a nucleotide sequence encoding a polypeptide of the UGT-AtSUS1 fusion enzyme having a nucleic acid sequence that has at least 70%, at least 75%, at least 80%, at least 85%, at least 90%, at least 91%, at least 92%, at least 93%, at least 94%, at least 95%, at least 96%, at least 97%, at least 98%, at least 99%, and even 100% sequence homology to the nucleic acid sequence set forth in SEQ ID NO:10. Suitably, the isolated nucleic acid includes a nucleotide sequence encoding a polypeptide of the UDP-glycosyltransferase fusion enzyme having an amino acid sequence that is at least 80% sequence identity to the amino acid sequence set forth in SEQ ID NO:9. More suitably, the isolated nucleic acid includes a nucleotide sequence encoding a polypeptide of the UDP-glycosyltransferase fusion enzyme having an amino acid sequence that has at least 85%, at least 90%, at least 91%, at least 92%, at least 93%, at least 94%, at least 95%, at least 96%, at least 97%, at least 98%, at least 99%, and even 100% sequence identity to the amino acid sequence set forth in SEQ ID NO:9. The isolated nucleic acid thus includes those nucleotide sequences encoding functional fragments of SEQ ID NO:10, functional variants of SEQ ID NO:9, or other homologous polypeptides that have, for example, at least 80%, at least 85%, at least 90%, at least 91%, at least 92%, at least 93%, at least 94%, at least 95%, at least 96%, at least 97%, at least 98%, at least 99%, and even 100% sequence identity to SEQ ID NO:9. As known by those skilled in the art, the nucleic acid sequence encoding the UDP-glycosyltransferase can be codon optimized for expression in a suitable host organism such as, for example, bacteria and yeast.

The EUGT11-SUS1 ("EUS") fusion enzyme can have a polypeptide sequence with at least 70%, at least 80%, at least 85%, at least 90%, at least 91%, at least 92%, at least 93%, at least 94%, at least 95%, at least 96%, at least 97%, at least 98%, at least 99% and even 100% identical to the amino acid sequence set forth in SEQ ID NO:11. Suitably, the amino acid sequence of the EUGT11-SUS1 fusion enzyme has at least 80% identity to SEQ ID NO:11. More suitably, the amino acid sequence of the EUGT11-SUS1 fusion enzyme has at least 85%, at least 90%, at least 91%, at least 92%, at least 93%, at least 94%, at least 95%, at least 96%, at least 97%, at least 98%, at least 99%, and even 100% amino acid sequence identity to the amino acid sequence set forth in SEQ ID NO:11.

The isolated nucleic acid can include a nucleotide sequence encoding a polypeptide of the EUGT11-SUS1 fusion enzyme having a nucleic acid sequence that has at least 70%, at least 75%, at least 80%, at least 85%, at least 90%, at least 91%, at least 92%, at least 93%, at least 94%, at least 95%, at least 96%, at least 97%, at least 98%, at least 99%, and even 100% sequence homology to the nucleic acid sequence set forth in SEQ ID NO:12. Suitably, the isolated nucleic acid includes a nucleotide sequence encoding a polypeptide of the EUGT11-SUS1 fusion enzyme having an amino acid sequence that is at least 80% sequence identity to the amino acid sequence set forth in SEQ ID NO:11. More suitably, the isolated nucleic acid includes a nucleotide sequence encoding a polypeptide of the EUGT11-SUS1 fusion enzyme having an amino acid sequence that has at least 85%, at least 90%, at least 91%, at least 92%, at least 93%, at least 94%, at least 95%, at least 96%, at least 97%, at least 98%, at least 99%, and even 100% sequence identity to the amino acid sequence set forth in SEQ ID NO:11. The isolated nucleic acid thus includes those nucleotide sequences encoding functional fragments of SEQ ID NO:11, functional variants of SEQ ID NO:11, or other homologous polypeptides that have, for example, at least 80%, at least 85%, at least 90%, at least 91%, at least 92%, at least 93%, at least 94%, at least 95%, at least 96%, at least 97%, at least 98%, at least 99%, and even 100% sequence identity to SEQ ID NO:11. As known by those skilled in the art, the nucleic acid sequence encoding the EUGT11-SUS1 can be codon optimized for expression in a suitable host organism such as, for example, bacteria and yeast.

Orally Consumable Products

In another aspect, the present disclosure is directed to an orally consumable product having a sweetening amount of rebaudioside V, selected from the group consisting of a beverage product and a consumable product. In another aspect, the present disclosure is directed to an orally consumable product having a sweetening amount of rebaudioside W, selected from the group consisting of a beverage product and a consumable product. In another aspect, the present disclosure is directed to an orally consumable product having a sweetening amount of rebaudioside KA, selected from the group consisting of a beverage product and a consumable product. In another aspect, the present disclosure is directed to an orally consumable product having a sweetening amount of rebaudioside G, selected from the group consisting of a beverage product and a consumable product. In another aspect, the present disclosure is directed to an orally consumable product having a sweetening amount of rebaudioside M, selected from the group consisting of a beverage product and a consumable product.

The orally consumable product can have a sweetness intensity equivalent to about 1% (w/v-%) to about 4% (w/v-%) sucrose solution.

The orally consumable product can have from about 5 ppm to about 100 ppm rebaudioside V. The orally consumable product can have from about 5 ppm to about 100 ppm rebaudioside W. The orally consumable product can have from about 5 ppm to about 100 ppm rebaudioside KA. The orally consumable product can have from about 5 ppm to about 100 ppm rebaudioside G. The orally consumable product can have from about 5 ppm to about 100 ppm rebaudioside M.

The rebaudioside V can be the only sweetener in the orally consumable product. The rebaudioside W can be the only sweetener in the orally consumable product. The rebaudioside KA can be the only sweetener in the orally consumable product. The rebaudioside G can be the only sweetener in the orally consumable product. The rebaudioside M can be the only sweetener in the orally consumable product.

The orally consumable product can also have at least one additional sweetener. The at least one additional sweetener can be a natural high intensity sweetener, for example. The additional sweetener can be selected from a stevia extract, a steviol glycoside, stevioside, rebaudioside A, rebaudioside B, rebaudioside C, rebaudioside D, rebaudioside D3, rebaudioside E, rebaudioside F, dulcoside A, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside, mogroside IV, siamenoside I, mogroside V, monatin, thaumatin, monellin, brazzein, L-alanine, glycine, Lo Han Guo, hernandulcin, phyllodulcin, trilobtain, and combinations thereof.

The orally consumable product can also have at least one additive. The additive can be, for example, a carbohydrate, a polyol, an amino acid or salt thereof, a polyamino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoids, an alcohol, a polymer, and combinations thereof.

In one aspect, the present disclosure is directed to a beverage product comprising a sweetening amount of rebaudioside V. In one aspect, the present disclosure is directed to a beverage product comprising a sweetening amount of rebaudioside W. In one aspect, the present disclosure is directed to a beverage product comprising a sweetening amount of rebaudioside KA. In one aspect, the present disclosure is directed to a beverage product comprising a sweetening amount of rebaudioside G. In one aspect, the present disclosure is directed to a beverage product comprising a sweetening amount of rebaudioside M.

The beverage product can be, for example, a carbonated beverage product and a non-carbonated beverage product. The beverage product can also be, for example, a soft drink, a fountain beverage, a frozen beverage; a ready-to-drink beverage; a frozen and ready-to-drink beverage, coffee, tea, a dairy beverage, a powdered soft drink, a liquid concentrate, flavored water, enhanced water, fruit juice, a fruit juice flavored drink, a sport drink, and an energy drink.

In some embodiments, a beverage product of the present disclosure can include one or more beverage ingredients such as, for example, acidulants, fruit juices and/or vegetable juices, pulp, etc., flavorings, coloring, preservatives, vitamins, minerals, electrolytes, erythritol, tagatose, glycerine, and carbon dioxide. Such beverage products may be provided in any suitable form, such as a beverage concentrate and a carbonated, ready-to-drink beverage.

In certain embodiments, beverage products of the present disclosure can have any of numerous different specific formulations or constitutions. The formulation of a beverage product of the present disclosure can vary to a certain extent, depending upon such factors as the product's intended market segment, its desired nutritional characteristics, flavor profile, and the like. For example, in certain embodiments, it can generally be an option to add further ingredients to the formulation of a particular beverage product. For example, additional (i.e., more and/or other) sweeteners can be added, flavorings, electrolytes, vitamins, fruit juices or other fruit products, tastents, masking agents and the like, flavor enhancers, and/or carbonation typically may be added to any such formulations to vary the taste, mouthfeel, nutritional characteristics, etc. In embodiments, the beverage product can be a cola beverage that contains water, about 5 ppm to about 100 ppm rebaudioside V, an acidulant, and flavoring. In embodiments, the beverage product can be a cola beverage that contains water, about 5 ppm to about 100 ppm rebaudioside W, an acidulant, and flavoring. In embodiments, the beverage product can be a cola beverage that contains water, about 5 ppm to about 100 ppm rebaudioside M, an acidulant, and flavoring. Exemplary flavorings can be, for example, cola flavoring, citrus flavoring, and spice flavorings. In some embodiments, carbonation in the form of carbon dioxide can be added for effervescence. In other embodiments, preservatives can be added, depending upon the other ingredients, production technique, desired shelf life, etc. In certain embodiments, caffeine can be added. In some embodiments, the beverage product can be a cola-flavored carbonated beverage, characteristically containing carbonated water, sweetener, kola nut extract and/or other flavoring, caramel coloring, one or more acids, and optionally other ingredients.

Suitable amounts of rebaudioside V, rebaudioside W, rebaudioside KA, rebaudioside M, or rebaudioside G present in the beverage product can be, for example, from about 5 ppm to about 100 ppm. In some embodiments, low concentrations of rebaudioside V, rebaudioside W, rebaudioside KA, rebaudioside M, or rebaudioside G, for example, less than 100 ppm, and has an equivalent sweetness to sucrose solutions having concentrations between 10,000 ppm to 30,000 ppm. The final concentration that ranges from about 5 ppm to about 100 ppm, from about 5 ppm to about 95 ppm, from about 5 ppm to about 90 ppm, from about 5 ppm to about 85 ppm, from about 5 ppm to about 80 ppm, from about 5 ppm to about 75 ppm, from about 5 ppm to about 70 ppm, from about 5 ppm to about 65 ppm, from about 5 ppm to about 60 ppm, from about 5 ppm to about 55 ppm, from about 5 ppm to about 50 ppm, from about 5 ppm to about 45 ppm, from about 5 ppm to about 40 ppm, from about 5 ppm to about 35 ppm, from about 5 ppm to about 30 ppm, from about 5 ppm to about 25 ppm, from about 5 ppm to about 20 ppm, from about 5 ppm to about 15 ppm, or from about 5 ppm to about 10 ppm. Alternatively, rebaudioside V or rebaudioside W can be present in beverage products of the present disclosure at a final concentration that ranges from about 5 ppm to about 100 ppm, from about 10 ppm to about 100 ppm, from about 15 ppm to about 100 ppm, from about 20 ppm to about 100 ppm, from about 25 ppm to about 100 ppm, from about 30 ppm to about 100 ppm, from about 35 ppm to about 100 ppm, from about 40 ppm to about 100 ppm, from about 45 ppm to about 100 ppm, from about 50 ppm to about 100 ppm, from about 55 ppm to about 100 ppm, from about 60 ppm to about 100 ppm, from about 65 ppm to about 100 ppm, from about 70 ppm to about 100 ppm, from about 75 ppm to about 100 ppm, from about 80 ppm to about 100 ppm, from about 85 ppm to about 100 ppm, from about 90 ppm to about 100 ppm, or from about 95 ppm to about 100 ppm.

In another aspect, the present disclosure is directed to a consumable comprising a sweetening amount of rebaudioside V. In another aspect, the present disclosure is directed to a consumable comprising a sweetening amount of rebaudioside W. In another aspect, the present disclosure is directed to a consumable comprising a sweetening amount of rebaudioside KA. In another aspect, the present disclosure is directed to a consumable comprising a sweetening amount of rebaudioside G. In another aspect, the present disclosure is directed to a consumable comprising a sweetening amount of rebaudioside M. The consumable can be, for example, a food product, a nutraceutical, a pharmaceutical, a dietary supplement, a dental hygienic composition, an edible gel composition, a cosmetic product and a tabletop flavoring.

As used herein, "dietary supplement(s)" refers to compounds intended to supplement the diet and provide nutrients, such as vitamins, minerals, fiber, fatty acids, amino acids, etc. that may be missing or may not be consumed in sufficient quantities in a diet. Any suitable dietary supplement known in the art may be used. Examples of suitable dietary supplements can be, for example, nutrients, vitamins, minerals, fiber, fatty acids, herbs, botanicals, amino acids, and metabolites.

As used herein, "nutraceutical(s)" refers to compounds, which includes any food or part of a food that may provide medicinal or health benefits, including the prevention and/or treatment of disease or disorder (e.g., fatigue, insomnia, effects of aging, memory loss, mood disorders, cardiovascular disease and high levels of cholesterol in the blood, diabetes, osteoporosis, inflammation, autoimmune disorders, etc.). Any suitable nutraceutical known in the art may be used. In some embodiments, nutraceuticals can be used as supplements to food and beverages and as pharmaceutical formulations for enteral or parenteral applications which may be solid formulations, such as capsules or tablets, or liquid formulations, such as solutions or suspensions.

In some embodiments, dietary supplements and nutraceuticals can further contain protective hydrocolloids (such as gums, proteins, modified starches), binders, film-forming agents, encapsulating agents/materials, wall/shell materials, matrix compounds, coatings, emulsifiers, surface active agents, solubilizing agents (oils, fats, waxes, lecithins, etc.), adsorbents, carriers, fillers, co-compounds, dispersing agents, wetting agents, processing aids (solvents), flowing agents, taste-masking agents, weighting agents, jellyfying agents, gel-forming agents, antioxidants and antimicrobials.

As used herein, a "gel" refers to a colloidal system in which a network of particles spans the volume of a liquid medium. Although gels mainly are composed of liquids, and thus exhibit densities similar to liquids, gels have the structural coherence of solids due to the network of particles that spans the liquid medium. For this reason, gels generally appear to be solid, jelly-like materials. Gels can be used in a number of applications. For example, gels can be used in foods, paints, and adhesives. Gels that can be eaten are referred to as "edible gel compositions." Edible gel compositions typically are eaten as snacks, as desserts, as a part of staple foods, or along with staple foods. Examples of suitable edible gel compositions can be, for example, gel desserts, puddings, jams, jellies, pastes, trifles, aspics, marshmallows, gummy candies, and the like. In some embodiments, edible gel mixes generally are powdered or granular solids to which a fluid may be added to form an edible gel composition. Examples of suitable fluids can be, for example, water, dairy fluids, dairy analogue fluids, juices, alcohol, alcoholic beverages, and combinations thereof. Examples of suitable dairy fluids can be, for example, milk, cultured milk, cream, fluid whey, and mixtures thereof. Examples of suitable dairy analogue fluids can be, for example, soy milk and non-dairy coffee whitener.

As used herein, the term "gelling ingredient" refers to any material that can form a colloidal system within a liquid medium. Examples of suitable gelling ingredients can be, for example, gelatin, alginate, carageenan, gum, pectin, konjac, agar, food acid, rennet, starch, starch derivatives, and combinations thereof. It is well known to those in the art that the amount of gelling ingredient used in an edible gel mix or an edible gel composition can vary considerably depending on a number of factors such as, for example, the particular gelling ingredient used, the particular fluid base used, and the desired properties of the gel.

Gel mixes and gel compositions of the present disclosure can be prepared by any suitable method known in the art. In some embodiments, edible gel mixes and edible gel compositions of the present disclosure can be prepared using other ingredients in addition to the gelling agent. Examples of other suitable ingredients can be, for example, a food acid, a salt of a food acid, a buffering system, a bulking agent, a sequestrant, a cross-linking agent, one or more flavors, one or more colors, and combinations thereof.

Any suitable pharmaceutical composition known in the art may be used. In certain embodiments, a pharmaceutical composition of the present disclosure can contain from about 5 ppm to about 100 ppm of rebaudioside V, and one or more pharmaceutically acceptable excipients. In certain embodiments, a pharmaceutical composition of the present disclosure can contain from about 5 ppm to about 100 ppm of rebaudioside W, and one or more pharmaceutically acceptable excipients. In certain embodiments, a pharmaceutical composition of the present disclosure can contain from about 5 ppm to about 100 ppm of rebaudioside KA, and one or more pharmaceutically acceptable excipients. In certain embodiments, a pharmaceutical composition of the present disclosure can contain from about 5 ppm to about 100 ppm of rebaudioside G, and one or more pharmaceutically acceptable excipients. In certain embodiments, a pharmaceutical composition of the present disclosure can contain from about 5 ppm to about 100 ppm of rebaudioside M, and one or more pharmaceutically acceptable excipients. In some embodiments, pharmaceutical compositions of the present disclosure can be used to formulate pharmaceutical drugs containing one or more active agents that exert a biological effect. Accordingly, in some embodiments, pharmaceutical compositions of the present disclosure can contain one or more active agents that exert a biological effect. Suitable active agents are well known in the art (e.g., The Physician's Desk Reference). Such compositions can be prepared according to procedures well known in the art, for example, as described in Remington's Pharmaceutical Sciences, Mack Publishing Co., Easton, Pa., USA.

Rebaudioside V, rebaudioside W, rebaudioside KA, rebaudioside M, or rebaudioside G can be used with any suitable dental and oral hygiene compositions known in the art. Examples of suitable dental and oral hygiene compositions can be, for example, toothpastes, tooth polishes, dental floss, mouthwashes, mouth rinses, dentrifices, mouth sprays, mouth refreshers, plaque rinses, dental pain relievers, and the like.

Suitable amounts of rebaudioside V, rebaudioside W, rebaudioside KA, rebaudioside M, or rebaudioside G present in the consumable can be, for example, from about 5 parts per million (ppm) to about 100 parts per million (ppm). In some embodiments, low concentrations of rebaudioside V, rebaudioside W, rebaudioside KA, rebaudioside M, or rebaudioside G, for example, less than 100 ppm, has an equivalent sweetness to sucrose solutions having concentrations between 10,000 ppm to 30,000 ppm. The final concentration that ranges from about 5 ppm to about 100 ppm, from about 5 ppm to about 95 ppm, from about 5 ppm to about 90 ppm, from about 5 ppm to about 85 ppm, from about 5 ppm to about 80 ppm, from about 5 ppm to about 75 ppm, from about 5 ppm to about 70 ppm, from about 5 ppm to about 65 ppm, from about 5 ppm to about 60 ppm, from about 5 ppm to about 55 ppm, from about 5 ppm to about 50 ppm, from about 5 ppm to about 45 ppm, from about 5 ppm to about 40 ppm, from about 5 ppm to about 35 ppm, from about 5 ppm to about 30 ppm, from about 5 ppm to about 25 ppm, from about 5 ppm to about 20 ppm, from about 5 ppm to about 15 ppm, or from about 5 ppm to about 10 ppm. Alternatively, rebaudioside V or rebaudioside W can be present in consumable products of the present disclosure at a final concentration that ranges from about 5 ppm to about 100 ppm, from about 10 ppm to about 100 ppm, from about 15 ppm to about 100 ppm, from about 20 ppm to about 100 ppm, from about 25 ppm to about 100 ppm, from about 30 ppm to about 100 ppm, from about 35 ppm to about 100 ppm, from about 40 ppm to about 100 ppm, from about 45 ppm to about 100 ppm, from about 50 ppm to about 100 ppm, from about 55 ppm to about 100 ppm, from about 60 ppm to about 100 ppm, from about 65 ppm to about 100 ppm, from about 70 ppm to about 100 ppm, from about 75 ppm to about 100 ppm, from about 80 ppm to about 100 ppm, from about 85 ppm to about 100 ppm, from about 90 ppm to about 100 ppm, or from about 95 ppm to about 100 ppm.

In certain embodiments, from about 5 ppm to about 100 ppm of rebaudioside V, rebaudioside W, rebaudioside KA, rebaudioside M, or rebaudioside G is present in food product compositions. As used herein, "food product composition(s)" refers to any solid or liquid ingestible material that can, but need not, have a nutritional value and be intended for consumption by humans and animals.

Examples of suitable food product compositions can be, for example, confectionery compositions, such as candies, mints, fruit flavored drops, cocoa products, chocolates, and the like; condiments, such as ketchup, mustard, mayonnaise, and the like; chewing gums; cereal compositions; baked goods, such as breads, cakes, pies, cookies, and the like; dairy products, such as milk, cheese, cream, ice cream, sour cream, yogurt, sherbet, and the like; tabletop sweetener compositions; soups; stews; convenience foods; meats, such as ham, bacon, sausages, jerky, and the like; gelatins and gelatin-like products such as jams, jellies, preserves, and the like; fruits; vegetables; egg products; icings; syrups including molasses; snacks; nut meats and nut products; and animal feed.

Food product compositions can also be herbs, spices and seasonings, natural and synthetic flavors, and flavor enhancers, such as monosodium glutamate. In some embodiments, food product compositions can be, for example, prepared packaged products, such as dietetic sweeteners, liquid sweeteners, granulated flavor mixes, pet foods, livestock feed, tobacco, and materials for baking applications, such as powdered baking mixes for the preparation of breads, cookies, cakes, pancakes, donuts and the like. In other embodiments, food product compositions can also be diet and low-calorie food and beverages containing little or no sucrose.

In certain embodiments that may be combined with any of the preceding embodiments, the rebaudioside V, rebaudioside W, rebaudioside KA, rebaudioside M, or rebaudioside G is the only sweetener, and the product has a sweetness intensity equivalent to about 1% to about 4% (w/v-%) sucrose solution. In certain embodiments that can be combined with any of the preceding embodiments, the consumable products and beverage products can further include an additional sweetener, where the product has a sweetness intensity equivalent to about 1% to about 10% (w/v-%) sucrose solution. In certain embodiments that can be combined with any of the preceding embodiments, every sweetening ingredient in the product is a high intensity sweetener. In certain embodiments that can be combined with any of the preceding embodiments, every sweetening ingredient in the product can a natural high intensity sweetener. In certain embodiments that can be combined with any of the preceding embodiments, the additional sweetener contains one or more sweeteners selected from a stevia extract, a steviol glycoside, stevioside, rebaudioside A, rebaudioside B, rebaudioside C, rebaudioside D, rebaudioside D3, rebaudioside F, dulcoside A, rubusoside, steviolbioside, sucrose, high fructose corn syrup, fructose, glucose, xylose, arabinose, rhamnose, erythritol, xylitol, mannitol, sorbitol, inositol, AceK, aspartame, neotame, sucralose, saccharine, naringin dihydrochalcone (NarDHC), neohesperidin dihydrochalcone (NDHC), rubusoside mogroside IV, siamenoside I, mogroside V, monatin, thaumatin, monellin, brazzein, L-alanine, glycine, Lo Han Guo, hernandulcin, phyllodulcin, trilobtain, and combinations thereof. In certain embodiments that can be combined with any of the preceding embodiments, the consumable products and beverage products can further include one or more additives selected from a carbohydrate, a polyol, an amino acid or salt thereof, a poly-amino acid or salt thereof, a sugar acid or salt thereof, a nucleotide, an organic acid, an inorganic acid, an organic salt, an organic acid salt, an organic base salt, an inorganic salt, a bitter compound, a flavorant, a flavoring ingredient, an astringent compound, a protein, a protein hydrolysate, a surfactant, an emulsifier, a flavonoids, an alcohol, a polymer, and combinations thereof. In certain embodiments that can be combined with any of the preceding embodiments, the rebaudioside D3 has a purity of about 50% to about 100% by weight before it is added into the product.

Sweetener

In another aspect, the present disclosure is directed to a sweetener consisting of a chemical structure:

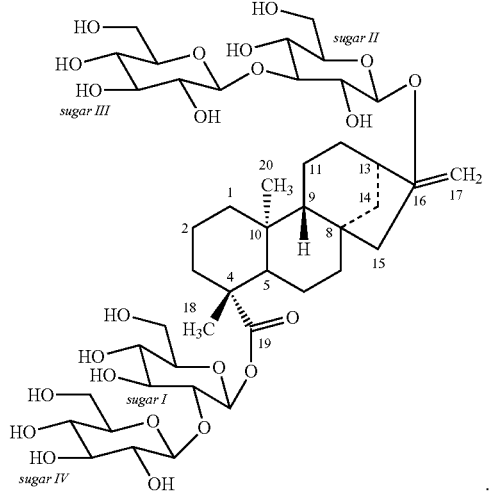
Reb V

In another aspect, the present disclosure is directed to a sweetener consisting of a chemical structure:

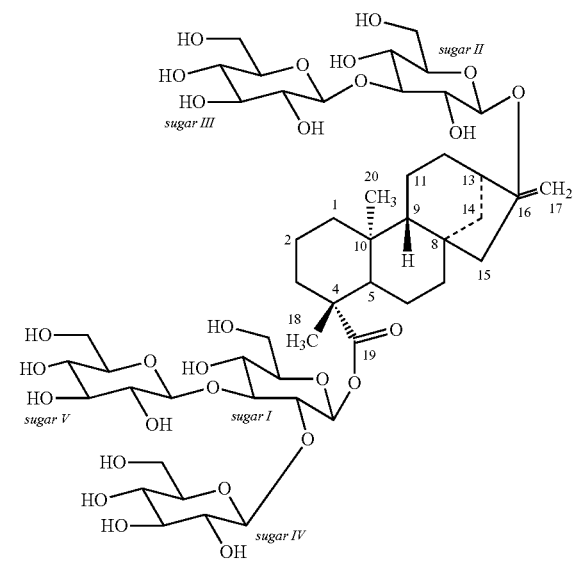
Reb W

In another aspect, the present disclosure is directed to a sweetener consisting of a chemical structure:

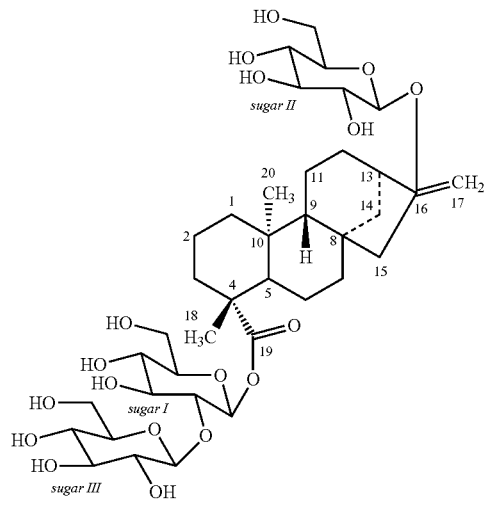
Reb KA

In another aspect, the present disclosure is directed to a sweetener consisting of a chemical structure:

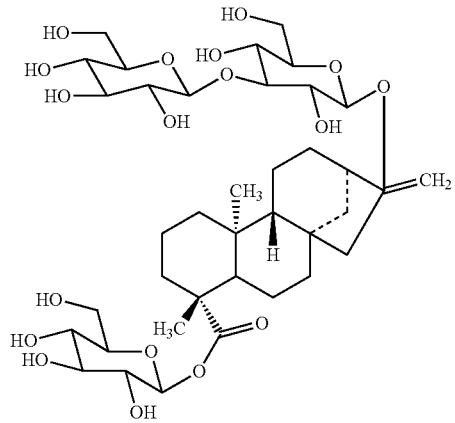
Reb G

In another aspect, the present disclosure is directed to a sweetener consisting of a chemical structure:

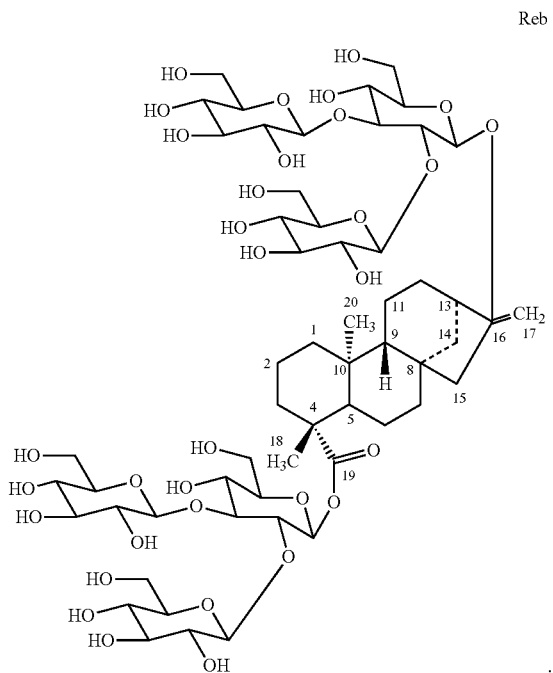

Reb M

In certain embodiments, the sweetener can further include at least one of a filler, a bulking agent and an anticaking agent. Suitable fillers, bulking agents and anticaking agents are known in the art.

In certain embodiments, rebaudioside V, rebaudioside W, rebaudioside KA, rebaudioside M, or rebaudioside G sweetener can be included and/or added at a final concentration that is sufficient to sweeten and/or enhance the sweetness of the consumable products and beverage products. The "final concentration" of rebaudioside V, rebaudioside W, rebaudioside KA, rebaudioside M, or rebaudioside G refers to the concentration of rebaudioside V, rebaudioside W, rebaudioside KA, rebaudioside M, or rebaudioside G present in the final consumable products and beverage products (i.e., after all ingredients and/or compounds have been added to produce the consumable products and beverage products). Accordingly, in certain embodiments, rebaudioside V, rebaudioside W, rebaudioside KA, rebaudioside M, or rebaudioside G is included and/or added to a compound or ingredient used to prepare the consumable products and beverage products. The rebaudioside V, rebaudioside W, rebaudioside KA, rebaudioside M, or rebaudioside G may be present in a single compound or ingredient, or multiple compounds and ingredients. In other embodiments, rebaudioside V, rebaudioside W, rebaudioside KA, rebaudioside M, or rebaudioside G is included and/or added to the consumable products and beverage products. In certain preferred embodiments, the rebaudioside V, rebaudioside W, rebaudioside KA, rebaudioside M, or rebaudioside G is included and/or added at a final concentration that ranges from about 5 ppm to about 100 ppm, from about 5 ppm to about 95 ppm, from about 5 ppm to about 90 ppm, from about 5 ppm to about 85 ppm, from about 5 ppm to about 80 ppm, from about 5 ppm to about 75 ppm, from about 5 ppm to about 70 ppm, from about 5 ppm to about 65 ppm, from about 5 ppm to about 60 ppm, from about 5 ppm to about 55 ppm, from about 5 ppm to about 50 ppm, from about 5 ppm to about 45 ppm, from about 5 ppm to about 40 ppm, from about 5 ppm to about 35 ppm, from about 5 ppm to about 30 ppm, from about 5 ppm to about 25 ppm, from about 5 ppm to about 20 ppm, from about 5 ppm to about 15 ppm, or from about 5 ppm to about 10 ppm. Alternatively, the rebaudioside V or rebaudioside W is included and/or added at a final concentration that ranges from about 5 ppm to about 100 ppm, from about 10 ppm to about 100 ppm, from about 15 ppm to about 100 ppm, from about 20 ppm to about 100 ppm, from about 25 ppm to about 100 ppm, from about 30 ppm to about 100 ppm, from about 35 ppm to about 100 ppm, from about 40 ppm to about 100 ppm, from about 45 ppm to about 100 ppm, from about 50 ppm to about 100 ppm, from about 55 ppm to about 100 ppm, from about 60 ppm to about 100 ppm, from about 65 ppm to about 100 ppm, from about 70 ppm to about 100 ppm, from about 75 ppm to about 100 ppm, from about 80 ppm to about 100 ppm, from about 85 ppm to about 100 ppm, from about 90 ppm to about 100 ppm, or from about 95 ppm to about 100 ppm. For example, rebaudioside V or rebaudioside W may be included and/or added at a final concentration of about 5 ppm, about 10 ppm, about 15 ppm, about 20 ppm, about 25 ppm, about 30 ppm, about 35 ppm, about 40 ppm, about 45 ppm, about 50 ppm, about 55 ppm, about 60 ppm, about 65 ppm, about 70 ppm, about 75 ppm, about 80 ppm, about 85 ppm, about 90 ppm, about 95 ppm, or about 100 ppm, including any range in between these values.

In certain embodiments, rebaudioside V, rebaudioside W, rebaudioside KA, rebaudioside M, or rebaudioside G is the only sweetener included and/or added to the consumable products and the beverage products. In such embodiments, the consumable products and the beverage products have a sweetness intensity equivalent to about 1% to about 4% (w/v-%) sucrose solution, about 1% to about 3% (w/v-%) sucrose solution, or about 1% to about 2% (w/v-%) sucrose solution. Alternatively, the consumable products and the beverage products have a sweetness intensity equivalent to about 1% to about 4% (w/v-%) sucrose solution, about 2% to about 4% (w/v-%) sucrose solution, about 3% to about 4% (w/v-%) sucrose solution, or about 4%. For example, the consumable products and the beverage products may have a sweetness intensity equivalent to about 1%, about 2%, about 3%, or about 4% (w/v-%) sucrose solution, including any range in between these values.

The consumable products and beverage products of the present disclosure can include a mixture of rebaudioside V, rebaudioside W, rebaudioside KA, rebaudioside M, or rebaudioside G and one or more sweeteners of the present disclosure in a ratio sufficient to achieve a desirable sweetness intensity, nutritional characteristic, taste profile, mouthfeel, or other organoleptic factor.

The disclosure will be more fully understood upon consideration of the following non-limiting Examples.

EXAMPLES

Example 1

In this Example, full-length DNA fragments of all candidate UGT genes were synthesized.

Specifically, the cDNAs were codon optimized for *E. coli* expression (Genscript, Piscataway, N.J.). The synthesized DNA was cloned into a bacterial expression vector pETite N-His SUMO Kan Vector (Lucigen). For the nucleotide sequence encoding the UDP-glycosyltransferase fusion enzymes (UGT76G1-AtSUS1 and EUGT11-AtSUS1), a GSG-linker (encoded by the nucleotide sequence: ggttctggt) was inserted in frame between a nucleotide sequence encoding the uridine diphospho glycosyltransferase domain and the nucleotide sequence encoding the sucrose synthase 1 from *A. thaliana* (AtSUS1). Table 2 summarizes the protein and sequence identifier numbers.

TABLE 2

Sequence Identification Numbers.

| Name | SEQ ID NO | Description |
|---|---|---|
| UGT76G1 | SEQ ID NO: 1 | Amino acid |
| UGT76G1 | SEQ ID NO: 2 | Nucleic acid |
| EUGT11 | SEQ ID NO: 3 | Amino acid |
| EUGT11 | SEQ ID NO: 4 | Nucleic acid |
| HV1 | SEQ ID NO: 5 | Amino acid |
| HV1 | SEQ ID NO: 6 | Nucleic acid |
| AtSUS1 | SEQ ID NO: 7 | Amino acid |
| AtSUS1 | SEQ ID NO: 8 | Nucleic acid |
| GS fusion enzyme | SEQ ID NO: 9 | Amino acid |
| GS fusion enzyme | SEQ ID NO: 10 | Nucleic acid |
| EUS fusion enzyme | SEQ ID NO: 11 | Amino acid |
| EUS fusion enzyme | SEQ ID NO: 12 | Nucleic acid |

Each expression construct was transformed into *E. coli* BL21 (DE3), which was subsequently grown in LB media containing 50 μg/mL kanamycin at 37° C. until reaching an $OD_{600}$ of 0.8-1.0. Protein expression was induced by addition of 1 mM isopropyl β-D-1-thiogalactopyranoside (IPTG) and the culture was further grown at 16° C. for 22 hr. Cells were harvested by centrifugation (3,000×g; 10 min; 4° C.). The cell pellets were collected and were either used immediately or stored at −80° C.

Figure 2:
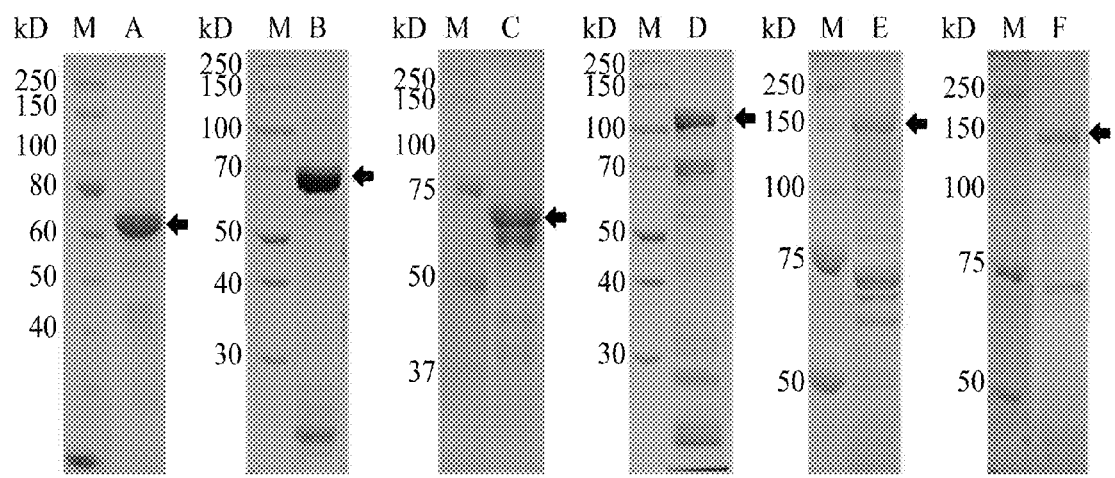
FIG. 2 depicts SDS-PAGE analysis purified recombinant proteins indicated by arrows: A: HV1, B: UGT76G1, C: EUGT11, D: AtSUS1, E: UGT76G1-SUS1 (GS), F: EUGT11-SUS1 (EUS).

The cell pellets were re-suspended in lysis buffer (50 mM potassium phosphate buffer, pH 7.2, 25 μg/ml lysozyme, 5 μg/ml DNase I, 20 mM imidazole, 500 mM NaCl, 10% glycerol, and 0.4% TRITON X-100). The cells were disrupted by sonication at 4° C., and the cell debris was clarified by centrifugation (18,000×g; 30 min). Supernatant was loaded to a equilibrated (equilibration buffer: 50 mM potassium phosphate buffer, pH 7.2, 20 mM imidazole, 500 mM NaCl, 10% glycerol) Ni-NTA (Qiagen) affinity column. After loading of protein sample, the column was washed with equilibration buffer to remove unbound contaminant proteins. The His-tagged UGT recombinant polypeptides were eluted by equilibration buffer containing 250 mM imidazole. Purified HV1 (61.4kD), UGT76G1 (65.4kD), AtSUS1 (106.3kD), EUGT11 (62kD), UGT76G1-SUS1 (GS) (157.25kD) and EUGT11-AtSUS1 (155kD) fusion proteins were shown in FIG. 2.

Example 2

In this Example, candidate UGT recombinant polypeptides were assayed for glycosyltranferase activity by using tested steviol glycosides as the substrate.

Typically, the recombinant polypeptide (10 μg) was tested in a 200 μl in vitro reaction system. The reaction system contains 50 mM potassium phosphate buffer, pH 7.2, 3 mM $MgCl_2$, 1 mg/ml steviol glycoside substrate, 1 mM UDP-glucose. The reaction was performed at 30° C. and terminated by adding 200 μL 1-butanol. The samples were extracted three times with 200 μL 1-butanol. The pooled fraction was dried and dissolved in 70 μL 80% methanol for high-performance liquid chromatography (HPLC) analysis. Rubusoside (99%, Blue California, Calif.), purified Reb G (98.8%), Reb KA (98.4%) and Reb V (80%) was used as substrate in in vitro reactions.

The UGT catalyzed glycosylation reaction was be coupled to a UDP-glucose generating reaction catalyzed by a sucrose synthase (such as AtSUS1). In this method, the UDP-glucose was generated from sucrose and UDP, such that the addition of extra UDP-glucose can be omitted. In the assay, recombinant AtSUS1 was added in UGT reaction system and UDP-glucose can be regenerated from UDP. AtSUS1 sequence (Bieniawska et al., Plant J. 2007, 49: 810-828) was synthesized and inserted into a bacterial expression vector. The recombinant AtSUS1 protein was expressed and purified by affinity chromatography.

HPLC analysis was performed using a Dionex UPLC ultimate 3000 system (Sunnyvale, Calif.), including a quaternary pump, a temperature controlled column compartment, an auto sampler and a UV absorbance detector. Phenomenex Luna $NH_2$, Luna C18 or Synergi Hydro-RP column with guard column was used for the characterization of steviol glycosides. Acetonitrile in water or in $Na_3PO_4$ buffer was used for isocratic elution in HPLC analysis. The detection wavelength was 210 nm.

Example 3

In this Example, the recombinant HV1 polypeptides were analyzed for transferring a sugar moiety to rubusoside to produce rebaudioside KA ("Minor diterpene glycosides from the leaves of *Stevia rebaudiana*". Journal of Natural Products (2014), 77(5), 1231-1235) in all reaction conditions with or without AtSUS1.

Figure 3:
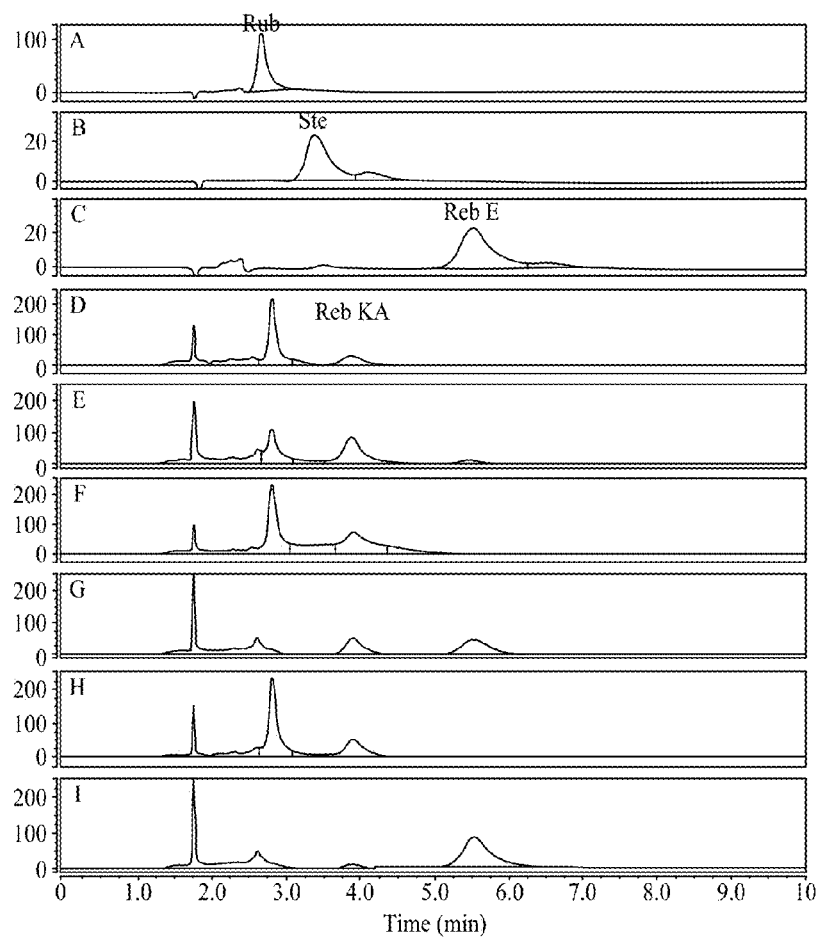
FIG. 3 depicts the HV1 catalysis reaction to produce rebaudioside KA ("Reb KA") and rebaudioside E ("Reb E") from rubusoside. A-C: showing the HPLC retention times of rubusoside ("Rub"), stevioside ("Ste") and rebaudioside E ("Reb E") standards. Reb KA enzymatically produced by HV1 alone at 6 hr (D), 12 hr (F) and 24 hours (H); Reb KA and Reb E enzymatically produced by the UGT-SUS (HV1-AtSUS1) coupling system at 6 hr (E), 12 hr (G) and 24 hr (I).

As shown in FIG. 3, the recombinant HV1 polypeptides transferred a sugar moiety to rubusoside to produce Reb KA in all reaction conditions with or without AtSUS1. Rubusoside was completely converted to Reb KA and Reb E by the recombinant HV1 in a UGT-SUS coupling reaction system (G, I). However, only partial rubososide was converted to Reb KA after 24 hours (H) by the recombinant HV1 polypeptide alone without being coupled to AtSUS1, indicating AtSUS1 enhanced the conversion efficiency in the UGT-SUS coupling system. In the HV1-AtSUS1 coupling reaction system, produced Reb KA can be continually converted to Reb E.

Example 4

In this Example, HV1 activity was analyzed using Reb E as a substrate.

Figure 4:
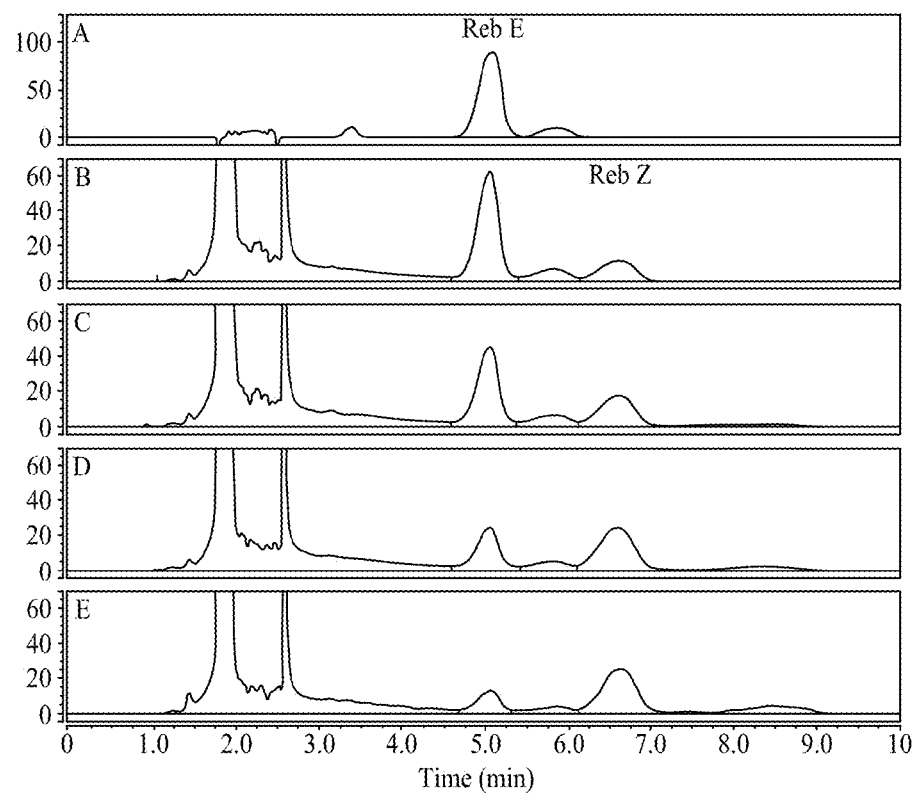
FIG. 4 depicts the conversion of Reb E to rebaudioside Z by HV1. (A): shows the HPLC retention time of rebaudioside E ("Reb E"). Rebaudioside Z ("Reb Z") enzymatically produced by HV1 in the HV1-AtSUS1 coupling system at 3 hr (B), 7 hr (C), 24 hr (D) and 44 hr (E).

Reb E substrate (0.5 mg/ml) was incubated with the recombinant HV1 polypeptide (20 μg) and AtSUS1 (20 μg) in a UGT-SUS coupling reaction system (200 μL) under conditions similar to those used in the examples above. As shown in FIG. 4, Reb Z was produced by the combination of the recombinant HV1 polypeptide and AtSUS1. These results indicated that HV1 can transfer a glucose moiety to Reb E to form RZ. FIG. 4 shows rebaudioside Z ("Reb Z") can be produced from rebaudioside E ("Reb E") catalyzed by a recombinant HV1 polypeptide and a recombinant AtSUS1 in a HV1-AtSUS1 coupling reaction system. HV1 can transfer a glucose to Reb E to produce Reb Z, mixture of Reb Z1 and Reb Z2 in the ratio between 60:40 to 70:30 (U.S. Provisional Application No. 61/898,571, assigned to Conagen Inc.).

Example 5

Figure 5:
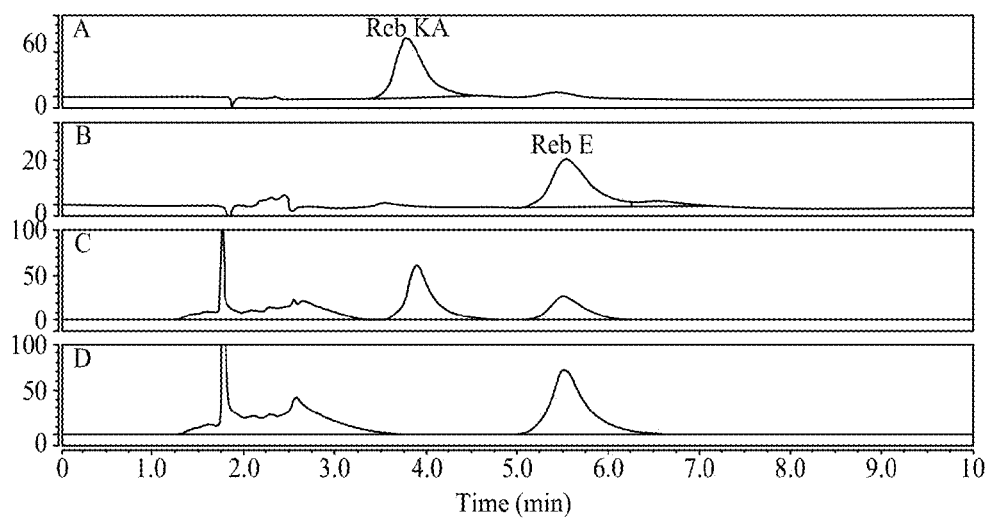
FIG. 5 depicts the conversion of Reb KA to Reb E by HV1. (A-B): show the HPLC retention times of rebaudioside KA ("Reb KA") and rebaudioside E ("Reb E") standards. Reb E enzymatically produced by HV1 alone at 12 hr (C); Reb E enzymatically produced by the UGT-SUS (HV1-AtSUS1) coupling system at 12 hr (D).

In this Example, to confirm the conversion of Reb KA to Reb E, purified Reb KA substrate was incubated with recombinant HV1 with or without AtSUS1. As shown in FIG. 5, Reb E was produced by the recombinant HV1 polypeptide in both reaction conditions. However, AtSUS1 polypeptide in a UGT-SUS coupling reaction system can enhance the reaction efficiency. All Reb KA substrate can be completely converted to Reb E in the UGT-SUS coupling system (D).

Example 6

In this Example, EUGT11 activity was analyzed using rubusoside as a substrate.

Figure 6:
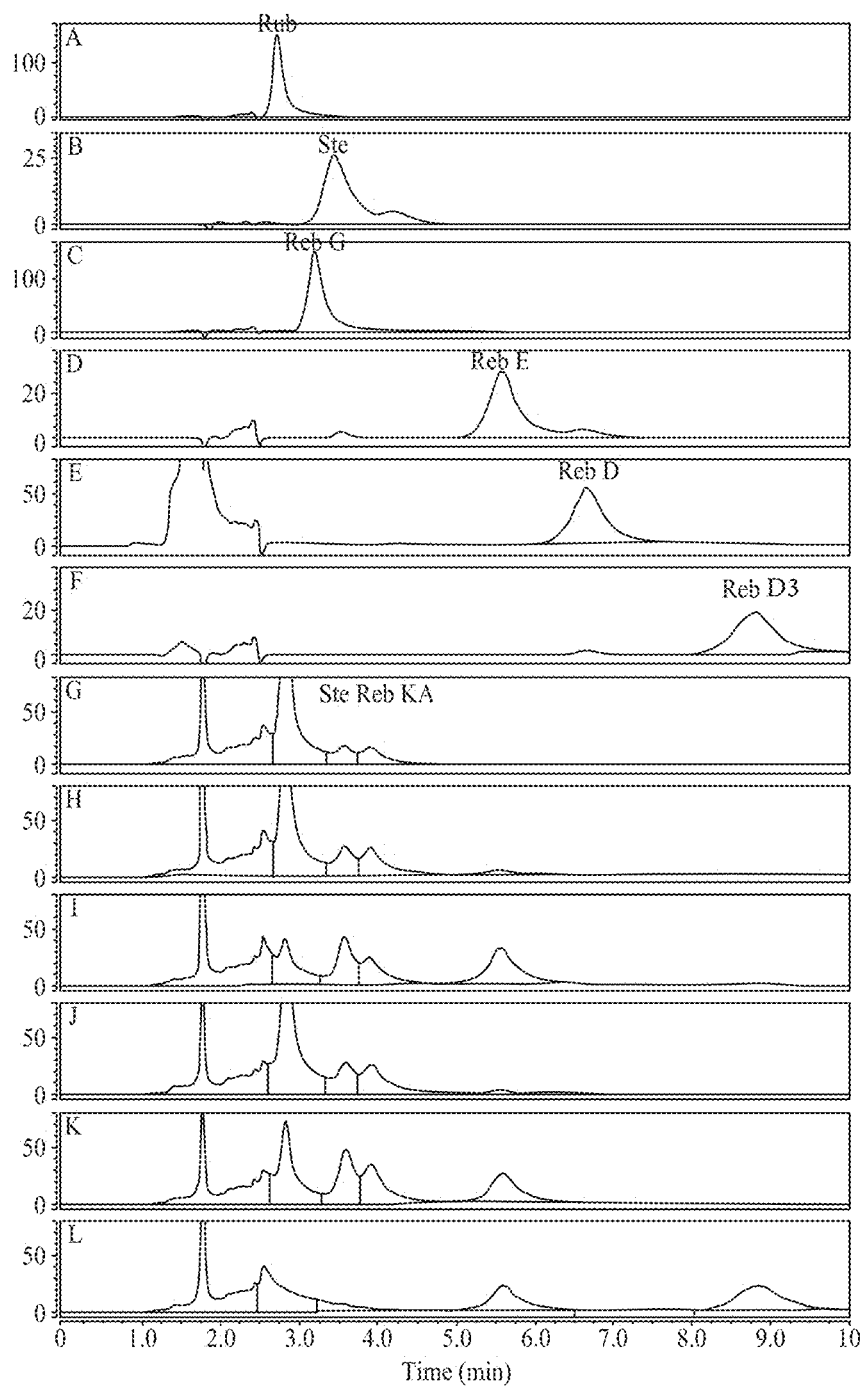
FIG. 6 depicts the EUGT11 catalysis reaction to produce Reb KA and stevioside from rubusoside. (A-F): show the HPLC retention times of rubusoside ("Rub"), stevioside ("Ste"), rebaudioside G ("Reb G"), rebaudioside E ("Reb E"), rebaudioside D ("Reb D") and rebaudioside D3 ("Reb D3") standards. Enzymatic reaction by EUGT11 alone at 12 hr (G) and 48 hr (J); enzymatic reaction by the UGT-SUS (EUGT11-AtSUS1) coupling system at 12 hr (H) and 48 hr (K); enzymatic reaction by EUS fusion protein at 12 hr (I) and 48 hr (L).

As shown in FIG. 6, EUGT11 can transfer a sugar moiety to rubusoside to produce Reb KA and stevioside in all reaction conditions with or without AtSUS1. AtSUS1 enhanced the conversion efficiency in the UGT-SUS coupling system. In the HV1-AtSUS1 coupling reaction system, Reb E can be continually converted by EUGT11. EUS fusion protein exhibited higher activity under same reaction condition. All produced Reb KA and stevioside was completely converted to Reb E by EUS at 48 hr. Reb E can be continually converted to Reb D3.

Example 7

In this Example, EUGT11 activity was analyzed using Reb KA as a substrate.

Figure 7:
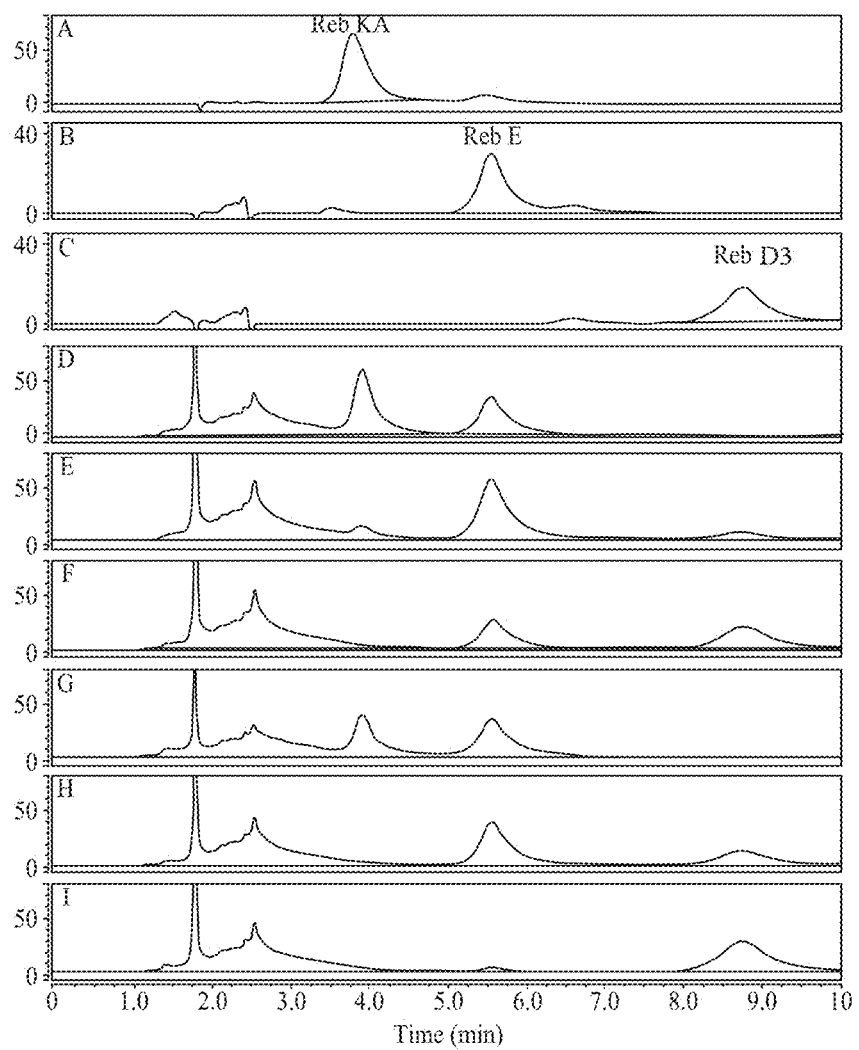
FIG. 7 depicts the conversion of Reb KA to Reb E and Reb D3 by EUGT11 and EUS fusion proteins. (A-C): showing the HPLC retention times of rebaudioside KA ("Reb KA"), rebaudioside E ("Reb E"), and rebaudioside D3 ("Reb D3") standards. Enzymatic reaction by EUGT11 alone at 12 hr (D) and 48 hr (G); enzymatic reaction by the UGT-SUS (EUGT11-AtSUS1) coupling system at 12 hr (E) and 48 hr (H); enzymatic reaction by EUS fusion protein at 12 hr (F) and 48 hr (I).

EUGT11 is a UGT with a 1,2-19-O-glucose glycosylation activity to produce related steviol glycoside (PCT Published Application WO2013/022989, assigned to Evolva SA). For example, EUGT11 can catalyze the reaction to produce Reb E from stevioside. EUGT11 also has a 1,6-13-O-glucose glycosylation activity that can transfer a glucose molecule to rebaudioside E to form rebaudioside D3 (U.S. patent application Ser. No. 14/269,435, assigned to Conagen, Inc.). In the experiments, we found EUGT11 can transfer a glucose residue to Reb KA to form Reb E. As shown in FIG. 7, EUGT11 can transfer a sugar moiety to Reb KA to produce Reb E in all reaction conditions with (E, H) or without AtSUS1 (D, G). AtSUS1 enhanced the conversion efficiency in the UGT-SUS coupling system (E, H). In the EUGT11-AtSUS1 coupling reaction system (E, H) and EUS fusion reaction system (F, I), all Reb KA was completely converted and the produced Reb E can be continually converted to Reb D3.

Example 8

In this Example, UGT76G1 activity was analyzed using rubusoside as a substrate.

UGT76G1 has 1,3-13-O-glucose glycosylation activity that can transfer a glucose molecule to stevioside to form rebaudioside A and to Reb E to form rebaudioside D. In the example, we found UGT76G1 can transfer a glucose residue to rubusoside to form rebaudioside G.

Figure 8:
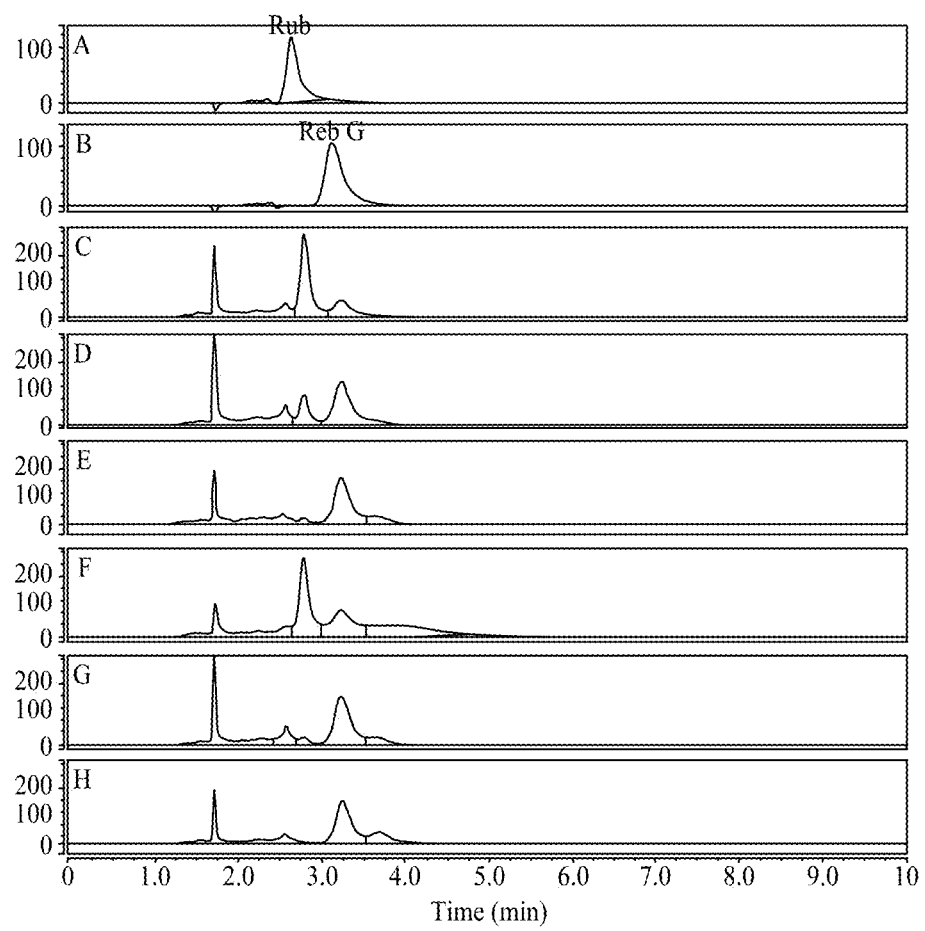
FIG. 8 depicts the UGT76G1 production of rebaudioside G in vitro. (A-B): show the HPLC retention times of rubusoside ("Rub") and rebaudioside G ("Reb G") standards. Enzymatic reaction by UGT76G1 alone at 12 hr (C) and 24 hr (F); enzymatic reaction by the UGT-SUS (EUGT11-AtSUS1) coupling system at 12 hr (D) and 24 hr (G); enzymatic reaction by GS fusion protein at 12 hr (E) and 48 hr (H).

As shown in FIG. 8, UGT76G1 can transfer a sugar moiety to rubusoside to produce Reb G in all reaction conditions with (D, G) or without AtSUS1 (C, F). AtSUS1 enhanced the conversion efficiency in the UGT-SUS coupling system. GS fusion protein exhibited higher activity under same reaction condition (E, H). All rubusoside was completely converted to Reb G by GS at 12 hr (E).

Example 9

In this Example, UGT76G1 activity was analyzed using rebaudioside KA as a substrate.

To further identify the enzymatic activity of UGT76G1, an in vitro assay was performed using rebaudioside KA as substrate. Surprisingly, a novel steviol glycoside (rebaudioside V "Reb V") was produced in an early time point. At later time points, Reb V produced in the reaction was converted to another novel steviol glycoside (rebaudioside W "RebW").

Figure 9:
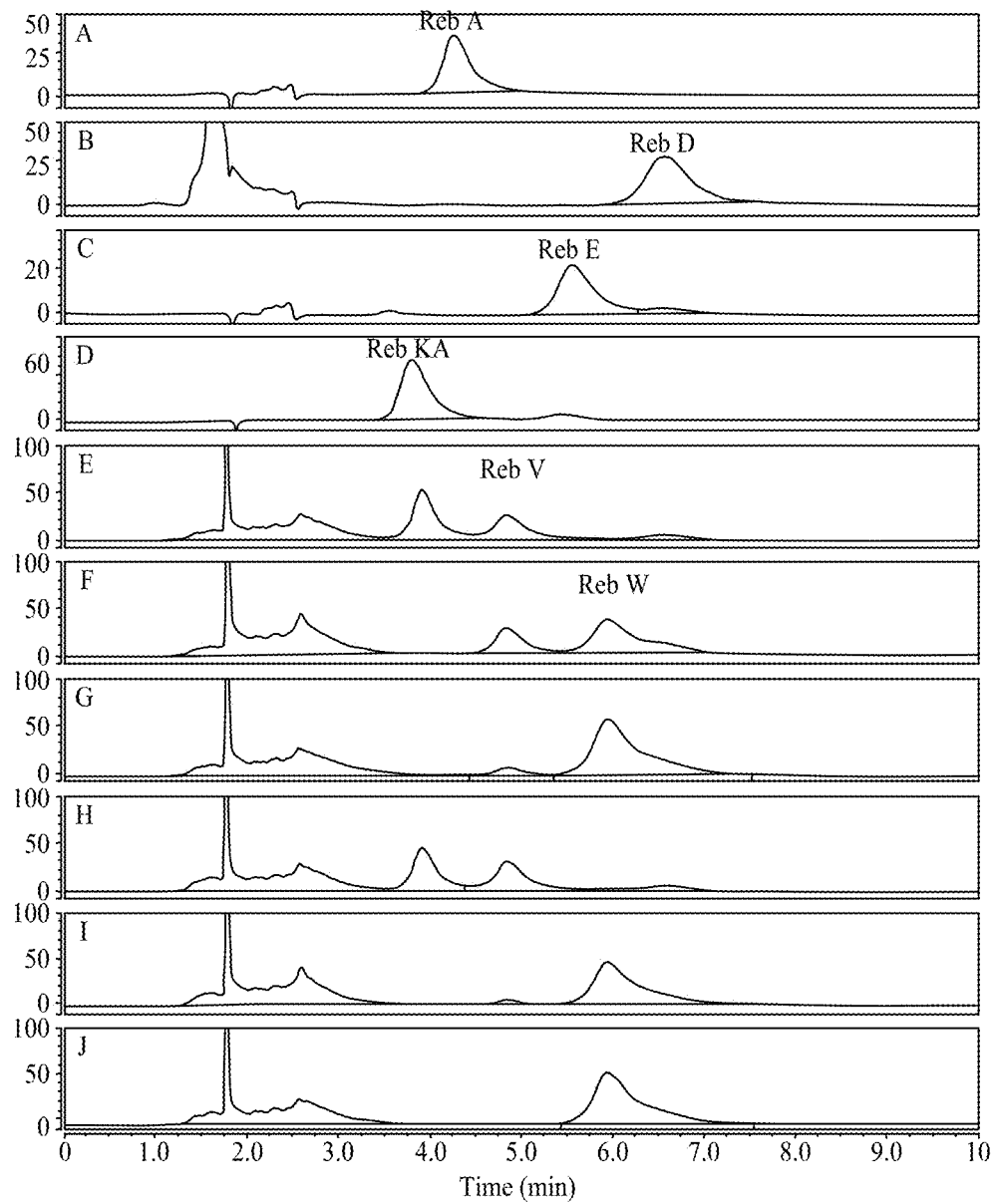
FIG. 9 depicts the UGT76G1 catalysis reaction to produce the steviol glycosides Reb V and Reb W from rebaudioside KA. (A-D): show the HPLC retention times of rubusoside ("Rub"), rebaudioside D ("Reb D"), rebaudioside E ("Reb E") and rebaudioside KA ("Reb KA") standards. Enzymatic reaction by UGT76G1 alone at 6 hr (E) and 12 hr (H); enzymatic reaction by the UGT-SUS (UGT76G1-AtSUS1) coupling system at 6 hr (F) and 12 hr (I); enzymatic reaction by GS fusion protein at 6 hr (G) and 12 hr (J).

As shown in FIG. 9, UGT76G1 can transfer a sugar moiety to Reb KA to produce Reb V in all reaction conditions with (F, I) or without AtSUS1 (E, H). AtSUS1 enhanced the conversion efficiency in the UGT-SUS coupling system (F, I). In the UGT76G1-AtSUS1 coupling reaction system (I) and GS fusion reaction system (J), produced Reb V was completely converted to Reb W at 12 hr.

Example 10

In this Example, UGT76G1 activity was analyzed using Reb V as a substrate.

Figure 10:
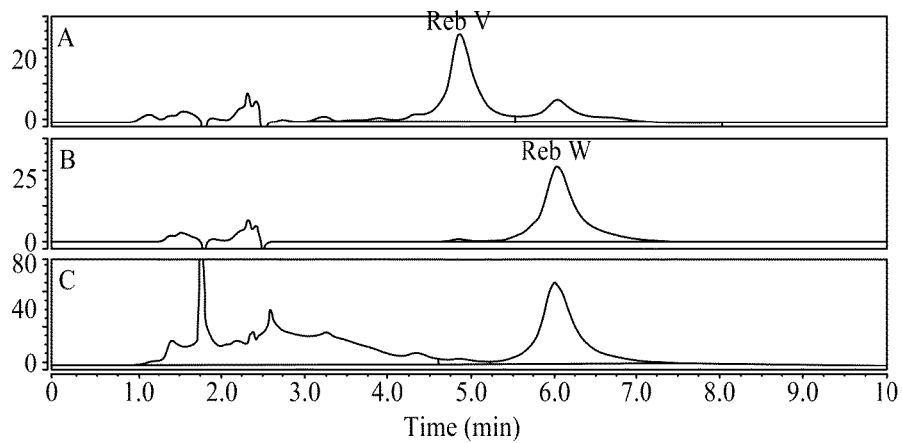
FIG. 10 depicts the UGT76G1 conversion of Reb V to Reb W in vitro. (A-B): showing the HPLC retention times of Reb V and Reb W. (C): Enzymatic reaction by the UGT76G1-AtSUS1 coupling system at 6 hr.

Purified Reb V as substrate was introduced into the reaction system. As shown in FIG. 10C, Reb V was surprisingly completely converted to Reb W by the UGT76G1 recombinant polypeptide in UGT-SUS1 coupling system at 6 hr.

Example 11

In this Example, HV1 activity was analyzed using Reb G as a substrate.

Figure 11:
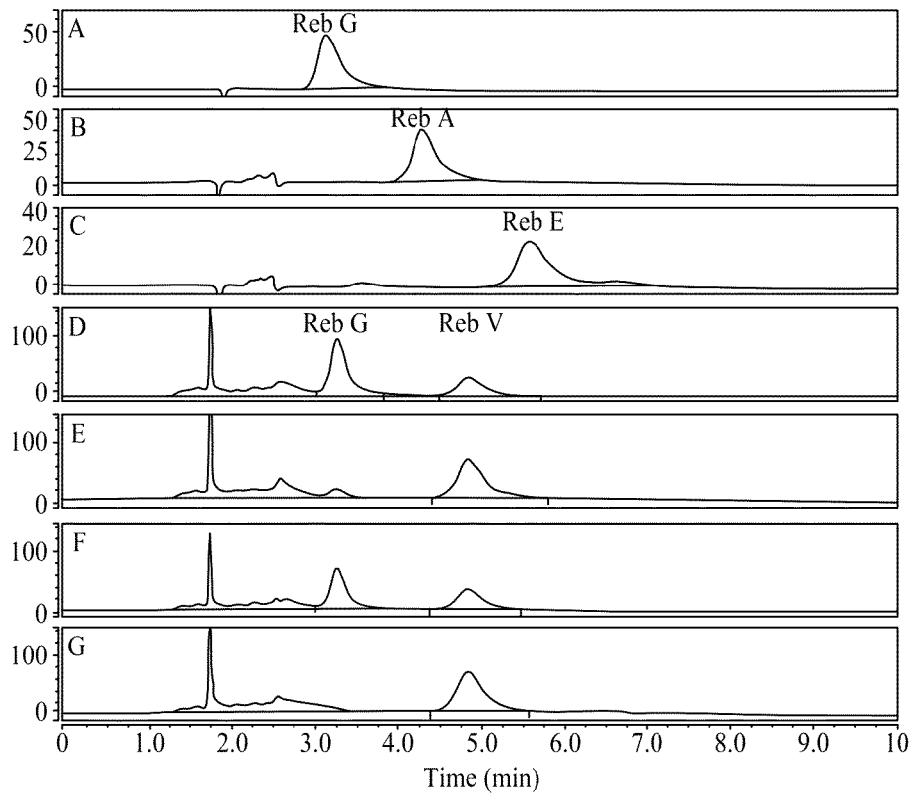
FIG. 11 depicts the HV1 conversion of Reb G to Reb V. (A-C): showing the HPLC retention times of rebaudioside G ("Reb G"), rebaudioside A ("Reb A") and rebaudioside E ("Reb E") standards. Enzymatic reaction by HV1 alone at 12 hr (D) and 24 hr (F); enzymatic reaction by the UGT-SUS (HV1-AtSUS1) coupling system at 12 hr (E) and 24 hr (G).

As shown in FIG. 11, the recombinant HV1 polypeptides transferred a sugar moiety to rebaudioside G to produce Reb V in all reaction conditions with or without AtSUS1. Reb G was completely converted to Reb V by the recombinant HV1 in a UGT-SUS coupling reaction system (E, G). However, only partial Reb G was converted to Reb V after 24 hours (F) by the recombinant HV1 polypeptide alone without being coupled to AtSUS1, indicating AtSUS1 enhanced the conversion efficiency in the UGT-SUS coupling system.

Example 12

In this Example, EUGT11 activity was analyzed using Reb G as a substrate.

Figure 12:
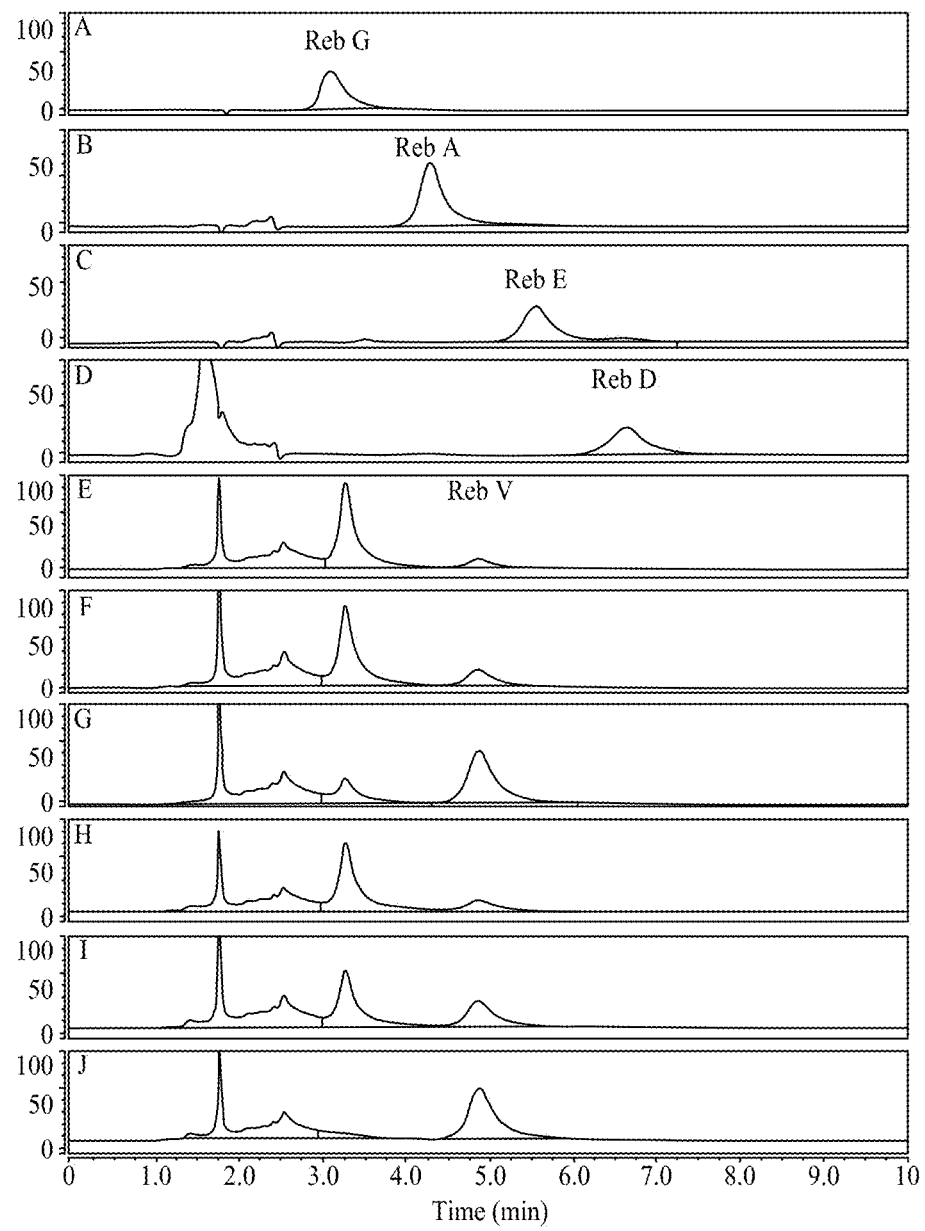
FIG. 12 depicts the EUGT11 conversion of Reb G to Reb V. (A-D): showing the HPLC retention times of rebaudioside G ("Reb G"), rebaudioside A ("Reb A"), rebaudioside E ("Reb E") and rebaudioside D ("Reb D") standards. Enzymatic reaction by EUGT11 alone at 12 hr (E) and 24 hr (H); enzymatic reaction by the UGT-SUS (EUGT11-AtSUS1) coupling system at 12 hr (F) and 24 hr (I); enzymatic reaction by EUS fusion enzyme at 12 hr (G) and 24 hr (J).

As shown in FIG. 12, the recombinant EUGT11 polypeptides transferred a sugar moiety to rebaudioside G to produce Reb V in all reaction conditions with (F, I) or without AtSUS1 (E, H). More Reb G was converted to Reb V by the recombinant EUGT11 in a UGT-SUS coupling reaction system (F, I). However, only partial Reb G was converted to Reb V by the recombinant EUGT11 polypeptide alone without being coupled to AtSUS1 (E, H), indicating AtSUS1 enhanced the conversion efficiency in the UGT-SUS coupling system. EUS fusion protein exhibited higher activity under same reaction condition (G, J). All Reb G in the reaction system was completely converted to Reb V by EUS at 24 hr (J).

Example 13

In this Example, HV1 combined with UGT76G1 activities were analyzed using rubusoside as a substrate.

Figure 13:
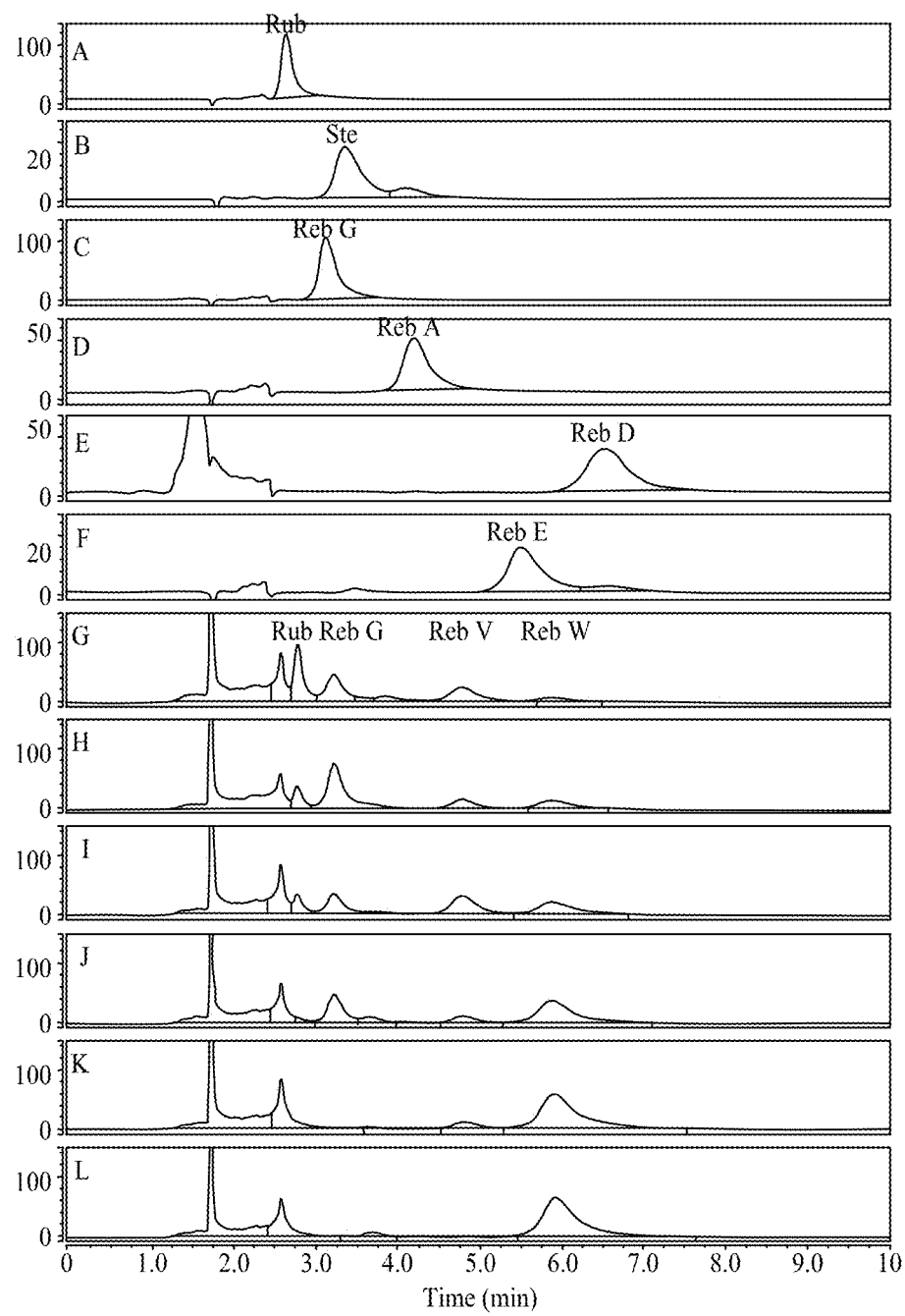
FIG. 13 depicts the in vitro production of Reb W from rubusoside catalyzed by a combination of a recombinant HV1 polypeptide, a recombinant UGT76G1, a GS fusion enzyme, and a recombinant AtSUS1. (A-F): show the standards of rubusoside ("Rub"), stevioside ("Ste"), Rebaudioside G ("Reb G"), rebaudioside A ("Reb A"), Rebaudioside D ("Reb D") and rebaudioside E ("Reb E"). Reb W enzymatically produced by HV1, UGT76G1 and AtSUS1 at 6 hours (G), 12 hr (I) and 24 hr (K); Reb W enzymatically produced by HV1 and GS fusion protein at 6 hours (H), 12 hr (J) and 24 hr (L).

Rebusoside substrate was incubated with the recombinant HV1 polypeptide, UGT76G1, and AtSUS1 in a UGT-SUS coupling reaction system under conditions similar to those used in the examples above. The products were analyzed by HPLC. As shown in FIG. 13, Reb V and Reb W was produced by the combination of the recombinant HV1 polypeptide, UGT76G1, and AtSUS1. Thus, the recombinant HV1 polypeptide, which showed a 1,2-19-O-glucose and 1,2-13-O-glucose glycosylation activity, can be used in combination with other UGT enzymes (such as UGT76G1, which showed a 1,3-13-O-glucose and 1,3-19-O-glucose glycosylation activity) for the complex, multi-step biosynthesis of steviol glycosides. If HV1 recombinant protein was combined with GS fusion protein in the reaction system, Reb V and Reb W was also produced by these UGT enzymes, indicating UGT-SUS coupling reaction can be generated by the GS fusion protein.

Example 14

In this Example, EUGT11 combined with UGT76G1 activities were analyzed using rubusoside as a substrate.

Figure 14:
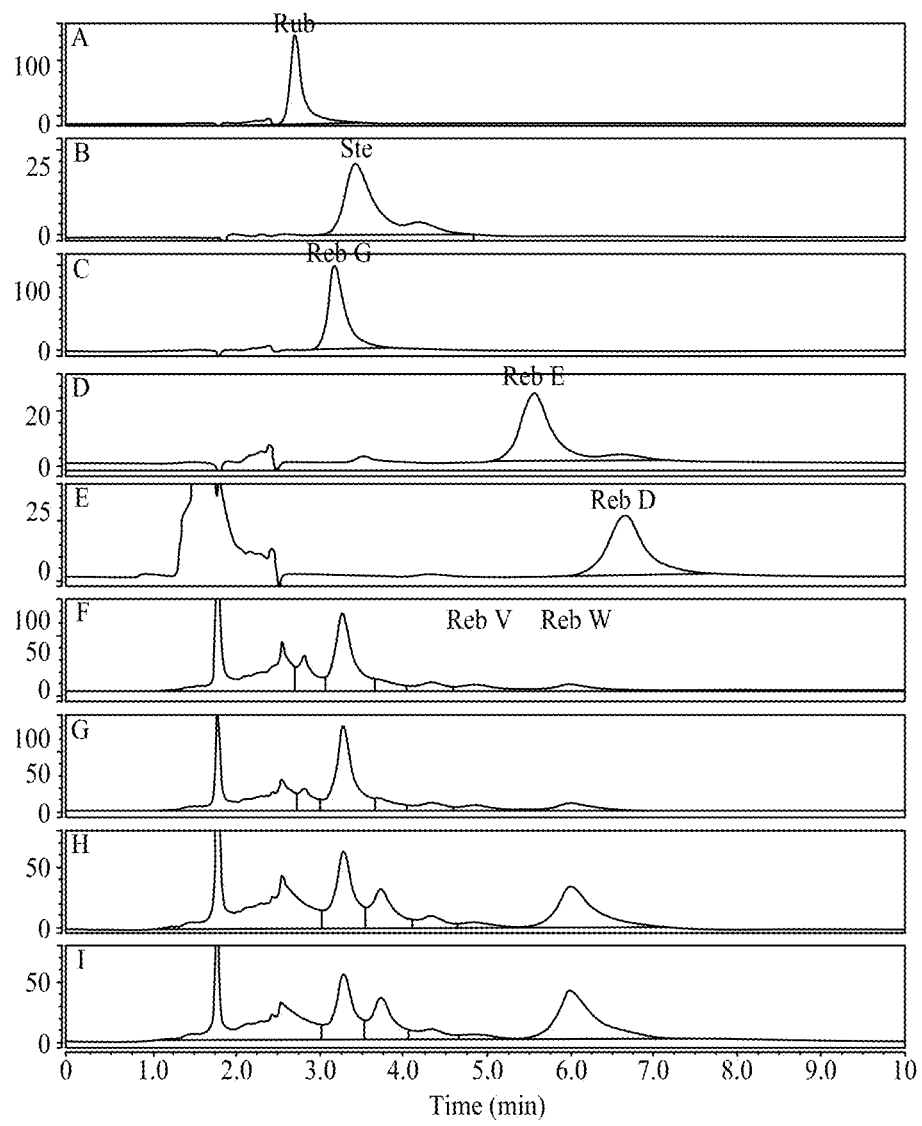
FIG. 14 depicts the in vitro production of Reb W from rubusoside catalyzed by a combination of a recombinant EUGT11 polypeptide, a recombinant UGT76G1, a GS fusion enzyme, and a recombinant AtSUS1. (A-E): show the standards of rubusoside ("Rub"), stevioside ("Ste"), rebaudioside G ("Reb G"), rebaudioside E ("Reb E") and rebaudioside D ("Reb D"). Reb W enzymatically produced by EUGT11, UGT76G1 and AtSUS1 at 12 hours (F) and 48 hr (H); Reb W enzymatically produced by EUGT11 and GS fusion protein at 12 hours (G) and 48 hr (I).

Rebusoside substrate was incubated with the recombinant EUGT11 polypeptide, UGT76G1, and AtSUS1 in a UGT-SUS coupling reaction system under conditions similar to those used in the examples above. The products were analyzed by HPLC. As shown in FIG. 14, Reb W was produced by the combination of the recombinant EUGT11 polypeptide, UGT76G1, and AtSUS1. Thus, the recombinant EUGT11 polypeptide, which showed a 1,2-19-O-glucose and 1,2-13-O-glucose glycosylation activity, can be used in combination with other UGT enzymes (such as UGT76G1, which showed a 1,3-13-O-glucose and 1,3-19-O-Glucose glycosylation activity) for the complex, multi-step biosynthesis of steviol glycosides. If EUGT11 recombinant protein was combined with GS fusion protein in the reaction system, Reb W was also produced by these UGT enzymes, indicating UGT-SUS coupling reaction can be generated by the GS fusion protein.

Example 15

In this Example, HV1 combined with UGT76G1 activities were analyzed using Reb G as a substrate.

Figure 15:
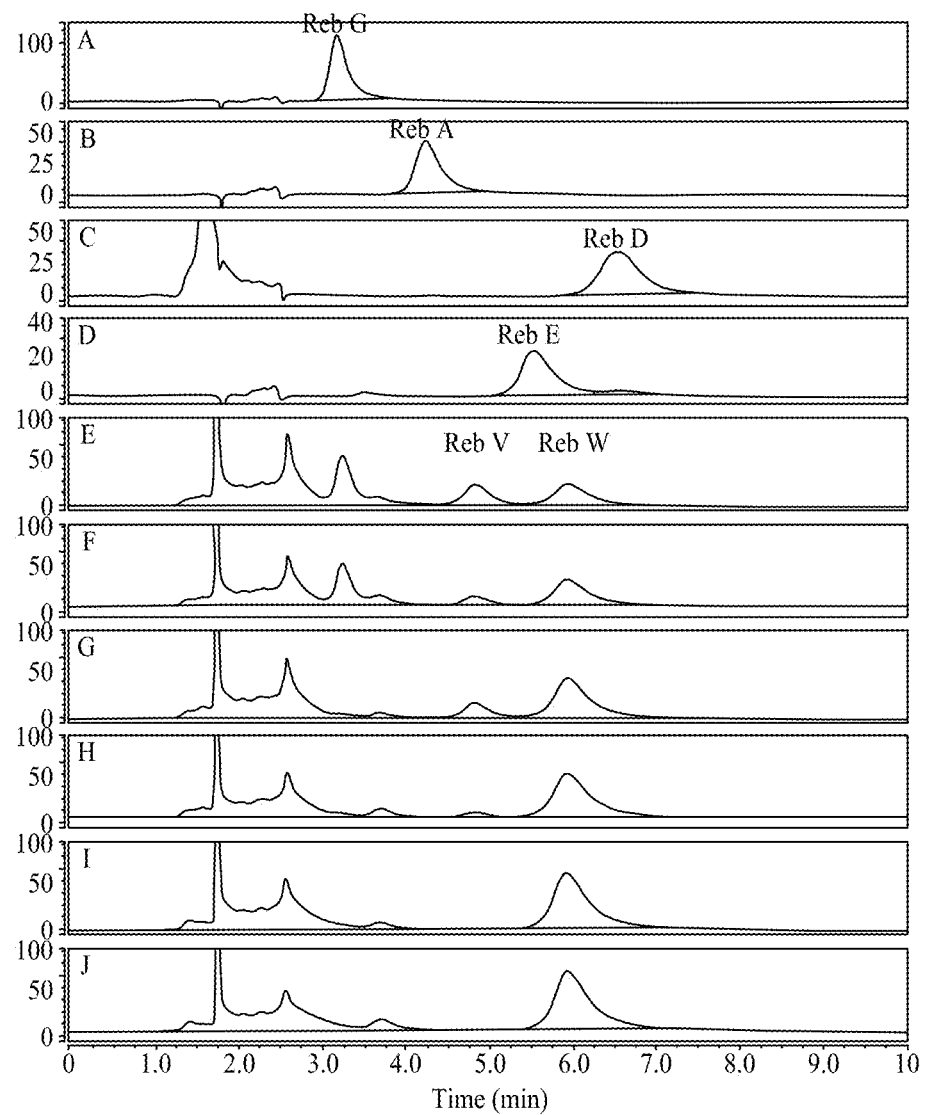
FIG. 15 depicts the in vitro production of Reb W from Reb G catalyzed by a combination of a recombinant HV1 polypeptide, a recombinant UGT76G1, a GS fusion enzyme and a recombinant AtSUS1. A-D shows the standards of rebaudioside G ("Reb G"), rebaudioside A ("Reb A"), Rebaudioside D ("Reb D"), rebaudioside and rebaudioside E ("Reb E"). Reb V and Reb W enzymatically produced by HV1, UGT76G1 and AtSUS1 at 6 hours (E), 12 hr (G) and 36 hr (I); Reb V and Reb W enzymatically produced by HV1 and GS fusion protein at 6 hours (F), 12 hr (H) and 36 hr (J).

Reb G substrate was incubated with the recombinant HV1 polypeptide, UGT76G1, and AtSUS1 in a UGT-SUS coupling reaction system under conditions similar to those used in the examples above. The products were analyzed by HPLC. As shown in FIG. 15, Reb V and Reb W was produced by the combination of the recombinant HV1 polypeptide, UGT76G1, and AtSUS1. After 12 hours, all rubusoside substrate was converted to Reb V, and after 36 hours, all produced Reb V was converted to Reb W. Thus, the recombinant HV1 polypeptide, which showed a 1,2-19-O-glucose and 1,2-13-O-glucose glycosylation activity, can be used in combination with other UGT enzymes (such as UGT76G1, which showed a 1,3-13-O-glucose and 1,3-19-O-Glucose glycosylation activity) for the complex, multi-step biosynthesis of steviol glycosides. If HV1 recombinant protein was combined with GS fusion protein in the reaction system, Reb V and Reb W was also produced by these UGT enzymes, indicating UGT-SUS coupling reaction can be generated by the GS fusion protein.

Example 16

In this Example, EUGT11 combined with UGT76G1 activities were analyzed using Reb G as a substrate.

Figure 16:
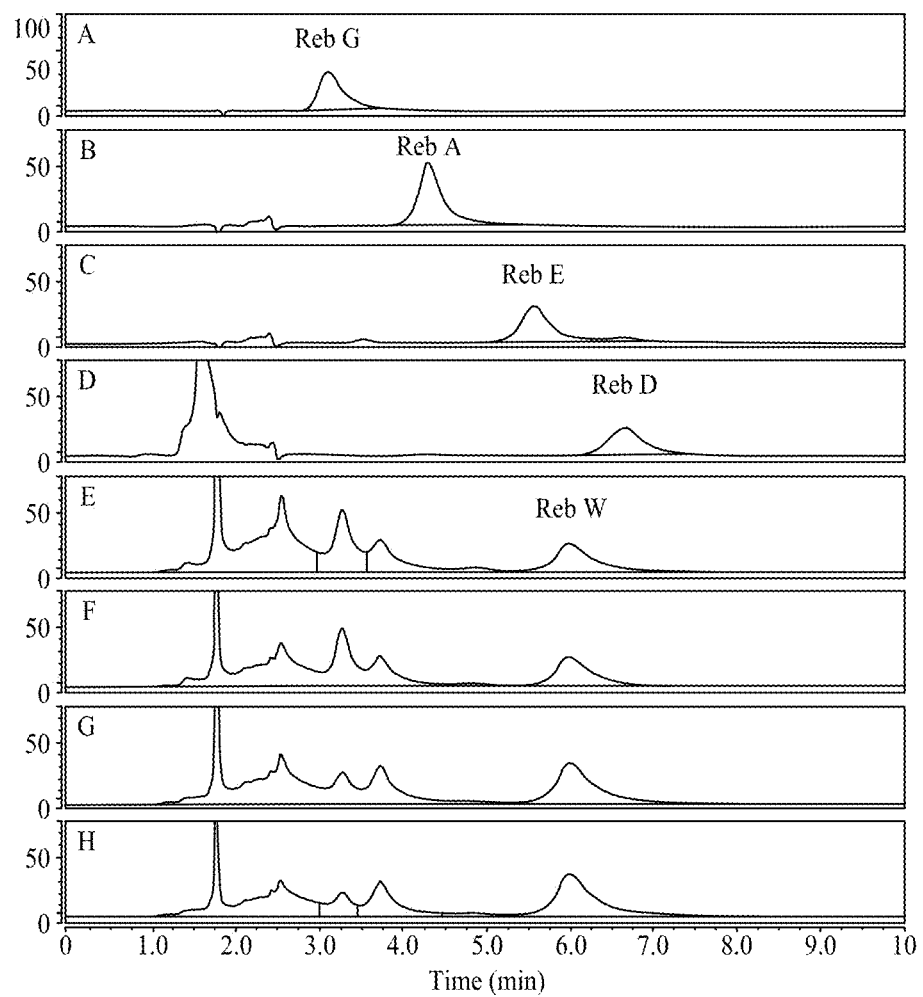
FIG. 16 depicts the in vitro production of Reb W from Reb G catalyzed by a combination of a recombinant EUGT11 polypeptide, a recombinant UGT76G1, a GS fusion enzyme, and a recombinant AtSUS1. (A-D): show the standards of rebaudioside G ("Reb G"), rebaudioside A ("Reb A"), rebaudioside E ("Reb E") and rebaudioside D ("Reb D"). Reb W enzymatically produced by EUGT11, UGT76G1 and AtSUS1 at 12 hours (E) and 48 hr (G); Reb W enzymatically produced by EUGT11 and GS fusion protein at 12 hours (F) and 48 hr (H).

Reb G substrate was incubated with the recombinant EUGT11 polypeptide, UGT76G1, and AtSUS1 in a UGT-SUS coupling reaction system under conditions similar to those used in the examples above. The products were analyzed by HPLC. As shown in FIG. 16, Reb W was produced by the combination of the recombinant EUGT11 polypeptide, UGT76G1, and AtSUS1. Thus, the recombinant EUGT11 polypeptide, which showed a 1,2-19-O-glucose and 1,2-13-O-glucose glycosylation activity, can be used in combination with other UGT enzymes (such as UGT76G1, which showed a 1,3-13-O-glucose and 1,3-19-O-Glucose glycosylation activity) for the complex, multi-step biosynthesis of steviol glycosides. If EUGT11 recombinant protein was combined with GS fusion protein in the reaction system, Reb W was also produced by these UGT enzymes, indicating UGT-SUS coupling reaction can be generated by the GS fusion protein.

Example 17

In this Example, UGT76G1 and GS fusion enzyme activity was analyzed using Reb D as a substrate.

Figure 22:
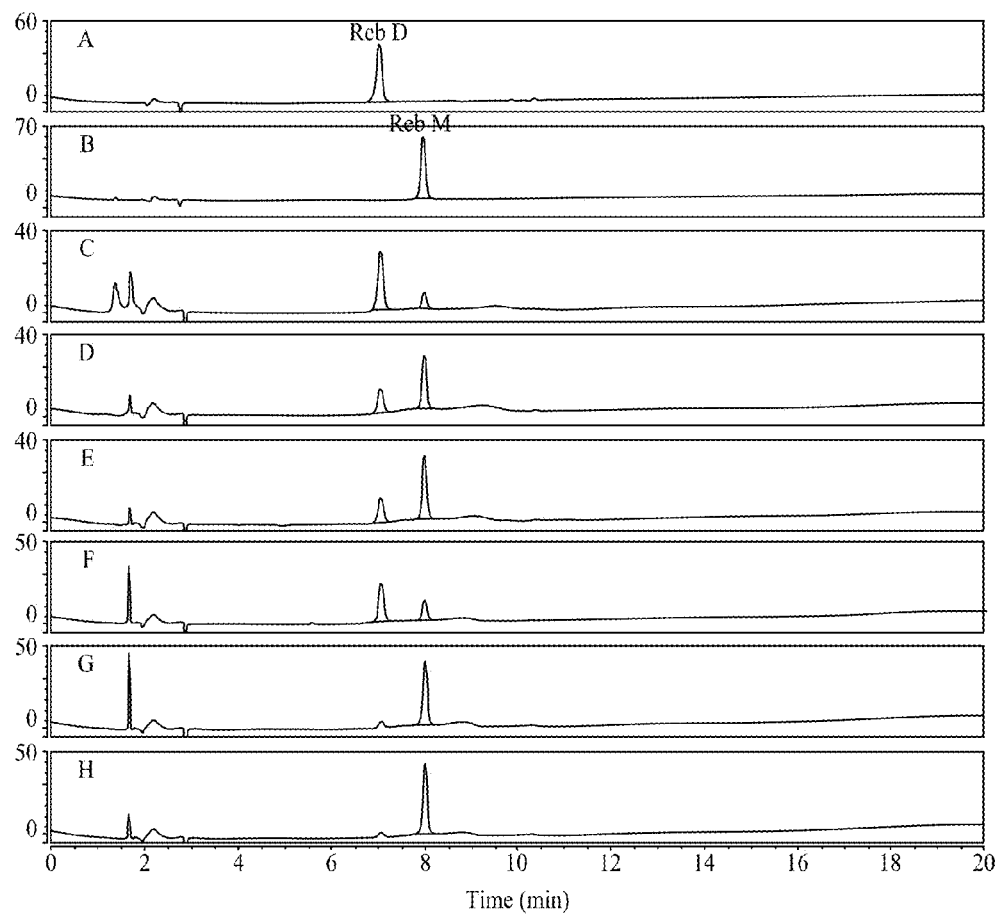
FIG. 22 depicts the in vitro production of Reb M from Reb D catalyzed by UGT76G1 and GS fusion enzyme. (A-B): showing the HPLC retention times of rebaudioside D ("Reb D") and rebaudioside M ("Reb M") standards. Enzymatic reaction by UGT76G1 alone at 3 hr (C) and 6 hr (F); enzymatic reaction by the UGT-SUS (UGT76G1-AtSUS1) coupling system at 3 hr (D) and 6 hr (G); enzymatic reaction by the GS fusion enzyme at 3 hr (E) and 6 hr (H).

Reb D substrate was incubated with the recombinant UGT76G1 under conditions similar to those used in the examples above. The products were analyzed by HPLC. As shown in FIG. 22, Reb M was produced by the UGT76G1 with (FIGS. 22 D and G) or without AtSUS1 (FIGS. 22 C and F) in the reactions. Thus, the recombinant UGT76G1 polypeptide, which showed a 1, 3-19-O-glucose glycosylation activity, can be used in biosynthesis of rebaudioside M. Reb D was completely converted to Reb M by the recombinant UGT76G1 in a UGT-SUS coupling reaction system (FIG. 22 G). However, only partial Reb D was converted to Reb M after 6 hours (F) by the recombinant UGT76G1 polypeptide alone without being coupled to AtSUS1, indicating AtSUS1 enhanced the conversion efficiency in the UGT-SUS coupling system. GS fusion protein exhibited similar activity as UGT76G1-AtSUS1 coupling reaction under same reaction condition (E, H). All Reb D was completely converted to Reb M by GS at 6 hr (H), indicating UGT-SUS coupling reaction can be generated by the GS fusion protein.

Example 18

In this Example, UGT76G1 and GS fusion enzyme activity was analyzed using Reb E as substrate.

Figure 23:
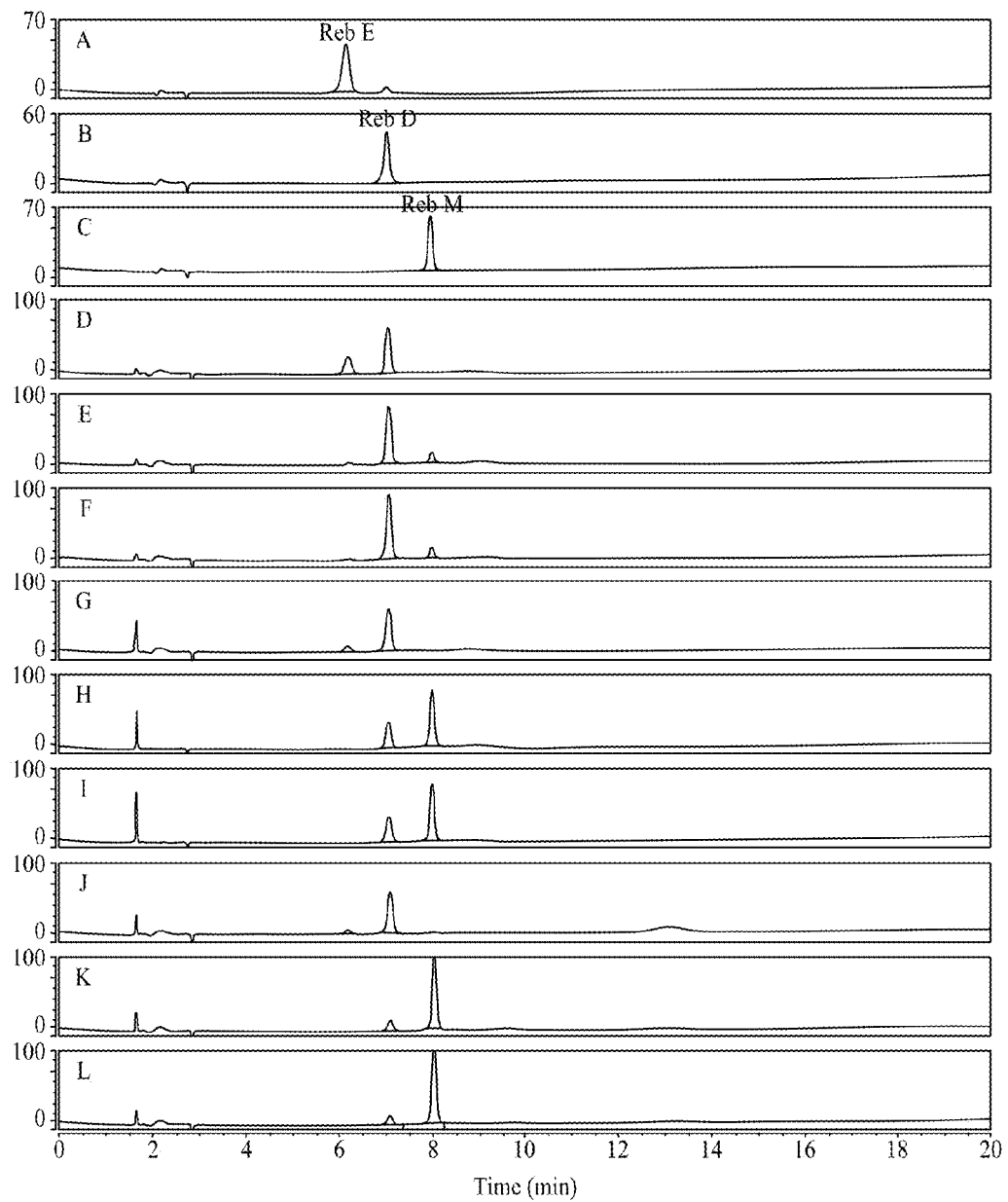
FIG. 23 depicts the in vitro production of Reb D and Reb M from Reb E catalyzed by UGT76G1 and GS fusion enzyme. (A-C): showing the HPLC retention times of rebaudioside E ("Reb E"), rebaudioside D ("Reb D") and rebaudioside M ("Reb M") standards. Enzymatic reaction by UGT76G1 alone at 3 hr (D), 12 hr (G) and 24 hr (J); enzymatic reaction by the UGT-SUS (UGT76G1-AtSUS1) coupling system at 3 hr (E), 12 hr (H) and 24 hr (K); enzymatic reaction by the GS fusion enzyme at 3 hr (F), 12 hr (I) and 24 hr (L).

Reb E substrate was incubated with the recombinant UGT76G1 or GS fusion enzyme under conditions similar to those used in the examples above. The products were analyzed by HPLC. As shown in FIG. 23, Reb D was produced by the UGT76G1 with (FIGS. 23 E, H and K) or without AtSUS1 (FIGS. 22 D, G and J) and GS fusion enzyme (FIGS. 23 F, I and L) in the reactions. Furthermore, Reb M was formed from Reb D produced in the reactions. Thus, the recombinant UGT76G1 polypeptide, which showed a 1,3-13-O-glucose and 1,3-19-O-glucose glycosylation activity, can be used in the biosynthesis of rebaudioside D and rebaudioside M. Reb E was completely converted to Reb M by the recombinant UGT76G1 in a UGT-SUS coupling reaction system after 24 hr (FIG. 23K). However, only Reb D was converted from Reb E completely after 24 hours (J) by the recombinant UGT76G1 polypeptide alone without being coupled to AtSUS1, indicating AtSUS1 enhanced the conversion efficiency in the UGT-SUS coupling system through continuing UDPG production. GS fusion protein exhibited similar activity as UGT76G1-AtSUS1 coupling reaction under same reaction condition (FIGS. 23 F, I and L), indicating UGT-SUS coupling reaction can be generated by the GS fusion protein.

Example 19

In this Example, HV1 combined with UGT76G1 activities were analyzed using stevioside as a substrate.

Figure 24:
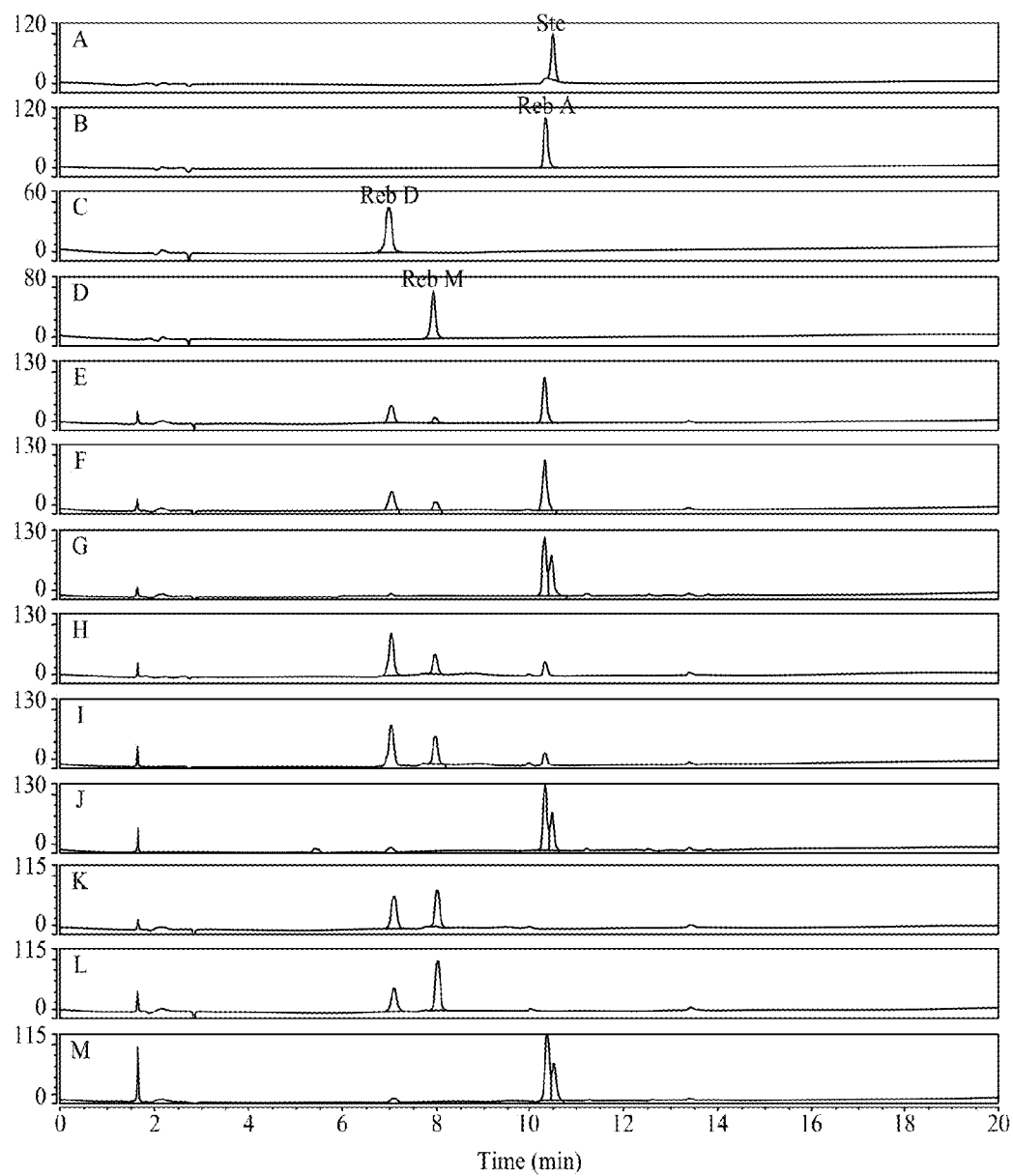
FIG. 24 depicts the in vitro production of Reb D and Reb M from stevioside catalyzed by a combination of a recombinant HV1, a recombinant UGT76G1, a GS fusion enzyme, and/or a recombinant AtSUS1. (A-D): showing the HPLC retention times of stevioside ("Ste"), rebaudioside A ("Reb A"), rebaudioside D ("Reb D") and rebaudioside M ("Reb M) standards. Enzymatic reaction by HV1 and UGT76G1 in the UGT-SUS coupling system at 6 hr (E), 12 hr (H) and 24 hr (K); enzymatic reaction by HV1 and GS fusion enzyme at 6 hr (F), 12 hr (I) and 24 hr (L). Enzymatic reaction by UGT76G1 and HV1 at 6 hr (G), 12 hr (J) and 24 hr (M).

Stevioside substrate was incubated with the recombinant HV1 polypeptide and UGT76G1 or GS fusion enzyme under conditions similar to those used in the examples above. The products were analyzed by HPLC. As shown in FIG. 24, Reb A was produced by the combination of the recombinant HV1 polypeptide and UGT76G1 in all reactions. Furthermore, Reb D and Reb M were detected in the reactions using the combination of recombinant HV1 polypeptide, UGT76G1 polypeptide and AtSUS1 (FIGS. 24 E, H and K) or the combination of recombinant GS fusion enzyme and HV1 polypeptide (FIGS. 24 F, I and L). The recombinant HV1 polypeptide, which showed a 1,2-19-O-glucose glycosylation activity, can be used in combination with other UGT enzymes (such as UGT76G1, which showed a 1,3-13-O-glucose and 1,3-19-O-glucose glycosylation activity) for the complex, multi-step biosynthesis of rebaudioside D and rebaudioside M. The results also showed that AtSUS1 enhanced the conversion efficiency in the UGT-SUS coupling system through continuing UDPG production (FIGS. 24 E, H and K). GS fusion protein exhibited similar activity as UGT76G1-AtSUS1 coupling reaction under same reaction condition (FIGS. 24 F, I and L), indicating UGT-SUS coupling reaction can be generated by the GS fusion protein.

Example 20

In this Example, HV1 combined with UGT76G1 activities were analyzed using Reb A as a substrate.

Figure 25:
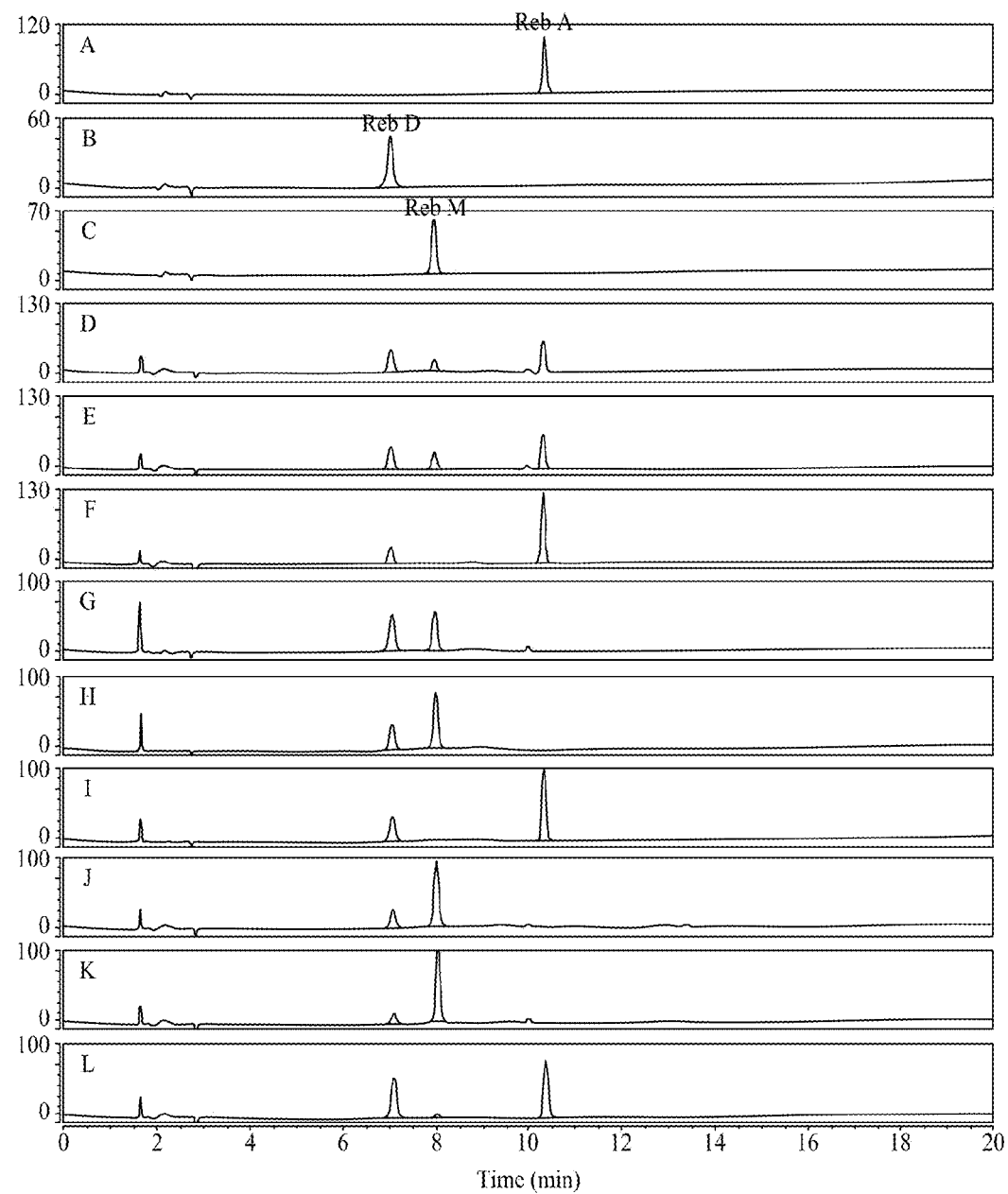
FIG. 25 depicts the in vitro production of Reb D and Reb M from rebaudioside A catalyzed by a combination of recombinant HV1, a recombinant UGT76G1, a GS fusion enzyme, and/or a recombinant AtSUS1. (A-C): showing the HPLC retention times of rebaudioside A ("Reb A"), rebaudioside D ("Reb D") and rebaudioside M ("Reb M) standards. Enzymatic reaction by HV1 and UGT76G1 in the UGT-SUS coupling system at 6 hr (D), 12 hr (G) and 24 hr (J); enzymatic reaction by HV1 and GS fusion enzyme at 6 hr (E), 12 hr (H) and 24 hr (K). Enzymatic reaction by UGT76G1 and HV1 at 6 hr (F), 12 hr (I) and 24 hr (J).

Reb A substrate was incubated with the recombinant HV1 polypeptide and UGT76G1 or GS fusion enzyme under conditions similar to those used in the examples above. The products were analyzed by HPLC. As shown in FIG. 25, Reb D was produced by the combination of the recombinant HV1 polypeptide and UGT76G1 in all reactions. Furthermore, Reb M was detected in the reactions using the combination of recombinant HV1 polypeptide, UGT76G1 polypeptide and AtSUS1 (FIGS. 25 D, G and J) or the combination of recombinant GS fusion enzyme and HV1 polypeptide (FIGS. 25 E, H and K). The recombinant HV1 polypeptide, which showed a 1,2-19-O-glucose glycosylation activity, can be used in combination with other UGT enzymes (such as UGT76G1, which showed a 1,3-19-O-glucose glycosylation activity) for the complex, multi-step biosynthesis of rebaudioside D and rebaudioside M. The results also showed that AtSUS1 enhanced the conversion efficiency in the UGT-SUS coupling system through continuing UDPG production (FIGS. 25 D, G and J). GS fusion protein exhibited similar activity as UGT76G1-AtSUS1 coupling reaction under same reaction condition (FIGS. 25 E, H and K), indicating UGT-SUS coupling reaction can be generated by the GS fusion protein.

Example 21

In this Example, the structure of Reb V was analyzed by NMR.

The material used for the characterization of Reb V was produced by using enzymatic conversion of Reb G and purified by HPLC. HRMS data were generated with a LTQ Orbitrap Discovery HRMS instrument, with its resolution set to 30 k. Scanned data from m/z 150 to 1500 in positive ion electrospray mode. The needle voltage was set to 4 kV; the other source conditions were sheath gas=25, aux gas=0, sweep gas=5 (all gas flows in arbitrary units), capillary voltage=30V, capillary temperature=300° C., and tube lens voltage=75. Sample was diluted with 2:2:1 acetonitrile:methanol:water (same as infusion eluent) and injected 50 microliters. NMR spectra were acquired on Bruker Avance DRX 500 MHz or Varian INOVA 600 MHz instruments using standard pulse sequences. The 1D ($^1$H and $^{13}$C) and 2D (TOCSY, HMQC, and HMBC) NMR spectra were performed in $C_5D_5N$.

The molecular formula of Reb V has been deduced as $C_{44}H_{70}O_{23}$ on the basis of its positive high resolution (HR) mass spectrum which showed adduct ions corresponding to $[M+Na]^+$ at m/z 989.4198; this composition was supported by the $^{13}$C NMR spectral data. The $^1$H NMR spectral data of Reb V showed the presence of two methyl singlets at δ 0.97 and 1.40, two olefinic protons as singlets at δ 5.06 and 5.71 of an exocyclic double bond, nine sp3 methylene and two sp3 methine protons between δ 0.74-2.72, characteristic for the ent-kaurane diterpenoids isolated earlier from the genus *Stevia*. The basic skeleton of ent-kaurane diterpenoids was supported by the COSY and TOCSY studies which showed key correlations: H-1/H-2; H-2/H-3; H-5/H-6; H-6/H-7; H-9/H-11; H-11/H-12. The $^1$H NMR spectrum of Reb V also showed the presence of four anomeric protons resonating at δ 5.08, 5.38, 5.57, and 6.23; suggesting four sugar units in its structure. Acid hydrolysis of Reb V with 5% $H_2SO_4$ afforded D-glucose which was identified by direct comparison with authentic sample by TLC. Enzymatic hydrolysis of Reb V furnished an aglycone which was identified as steviol by comparison of $^1$H NMR and co-TLC with standard compound. The large coupling constants observed for the four anomeric protons of the glucose moieties at δ 5.08 (d, J=7.8 Hz), 5.38 (d, J=8.1 Hz), 5.57 (d, J=8.0 Hz), and 6.23 (d, J=7.8 Hz), suggested their β-orientation as reported for steviol glycosides. The $^1$H and $^{13}$C NMR values for Reb V were assigned on the basis of TOCSY, HMQC and HMBC data and are given in Table 3.

TABLE 3

$^1$H and $^{13}$C NMR spectral data (chemical shifts and coupling constants) for Reb V and Reb G$^{a-c}$.

| | Reb V | | Reb G | |
|---|---|---|---|---|
| Position | $^1$H NMR | $^{13}$C NMR | $^1$H NMR | $^{13}$C NMR |
| 1 | 0.74 m, 1.66 m | 41.1 | 0.78 m, 1.69 m | 41.3 |
| 2 | 1.43 m, 2.18 m | 20.4 | 1.44 m, 2.20 m | 20.0 |
| 3 | 1.06 m, 2.72 d (12.8) | 38.4 | 1.05 m, 2.70 d (11.6) | 38.8 |
| 4 | — | 44.8 | — | 44.9 |
| 5 | 1.32 m | 57.9 | 1.32 m | 57.8 |
| 6 | 1.84 m, 2.20 m | 22.7 | 1.87 m, 2.24 m | 22.6 |
| 7 | 1.06 m, 1.70 m | 42.2 | 1.07 m, 1.72 m | 42.2 |
| 8 | — | 42.5 | — | 43.1 |
| 9 | 0.91 d (7.8) | 54.5 | 0.92 d (7.6) | 54.4 |
| 10 | — | 40.2 | — | 40.4 |
| 11 | 1.72 m | 21.0 | 1.75 m | 21.2 |
| 12 | 2.18 m, 2.38 m | 38.3 | 2.26 m, 2.38 m | 37.7 |
| 13 | — | 87.6 | — | 86.4 |
| 14 | 1.68 m, 2.43 m | 44.8 | 1.78 m, 2.50 m | 44.6 |
| 15 | 1.96 m, 2.24 m | 48.9 | 2.06 m, 2.32 m | 48.2 |
| 16 | — | 153.7 | — | 155.0 |
| 17 | 5.06 s, 5.71 s | 105.7 | 5.00 s, 5.49 s | 104.8 |
| 18 | 1.40 s | 29.6 | 1.32 s | 28.8 |
| 19 | — | 176.4 | — | 177.4 |
| 20 | 0.97 s | 16.7 | 1.25 s | 16.2 |
| 1' | 6.23 d (7.8) | 94.2 | 6.16 d (7.6) | 96.4 |
| 2' | 3.98 m | 74.5 | 4.01 m | 74.5 |
| 3' | 4.14 m | 79.3 | 4.09 m | 79.3 |
| 4' | 4.36 m | 71.6 | 4.34 m | 71.6 |

TABLE 3-continued $^1$H and $^{13}$C NMR spectral data (chemical shifts and coupling constants) for Reb V and Reb G$^{a-c}$.

| | Reb V | | Reb G | |
|---|---|---|---|---|
| Position | $^1$H NMR | $^{13}$C NMR | $^1$H NMR | $^{13}$C NMR |
| 5' | 4.24 m | 79.9 | 4.22 m | 79.9 |
| 6' | 4.06 m, 4.48 m | 62.6 | 4.04 m, 4.44 dd (3.2, 7.6) | 62.6 |
| 1" | 5.08 d (7.8) | 99.6 | 5.06 d (7.4) | 99.9 |
| 2" | 3.94 m | 74.7 | 3.92 m | 74.5 |
| 3" | 4.04 m | 89.3 | 4.06 m | 89.5 |
| 4" | 4.28 m | 71.2 | 4.23 m | 71.0 |
| 5" | 4.00 m | 78.2 | 4.02 m | 78.1 |
| 6" | 4.24 m, 4.58 m | 63.0 | 4.27 m, 4.56 dd (2.8, 8.4) | 63.1 |
| 1''' | 5.38 d (8.1) | 106.4 | 5.27 d (8.4) | 106.5 |
| 2''' | 4.16 m | 76.1 | 4.14 m | 76.0 |
| 3''' | 4.34 m | 79.2 | 4.37 m | 79.3 |
| 4''' | 4.26 m | 72.2 | 4.28 m | 72.2 |
| 5''' | 3.78 m | 78.8 | 3.89 m | 78.8 |
| 6''' | 4.14 m, 4.44 m | 63.2 | 4.18 m, 4.48 m | 63.2 |
| 1'''' | 5.57 d (8.0) | 105.7 | | |
| 2'''' | 3.96 m | 76.5 | | |
| 3'''' | 4.32 m | 79.6 | | |
| 4'''' | 4.20 m | 72.5 | | |
| 5'''' | 3.87 m | 79.0 | | |
| 6'''' | 4.12 m, 4.46 m | 63.5 | | |

$^a$assignments made on the basis of TOCSY, HMQC and HMBC correlations;
$^b$Chemical shift values are in δ (ppm);
$^c$Coupling constants are in Hz.

Figure 17:
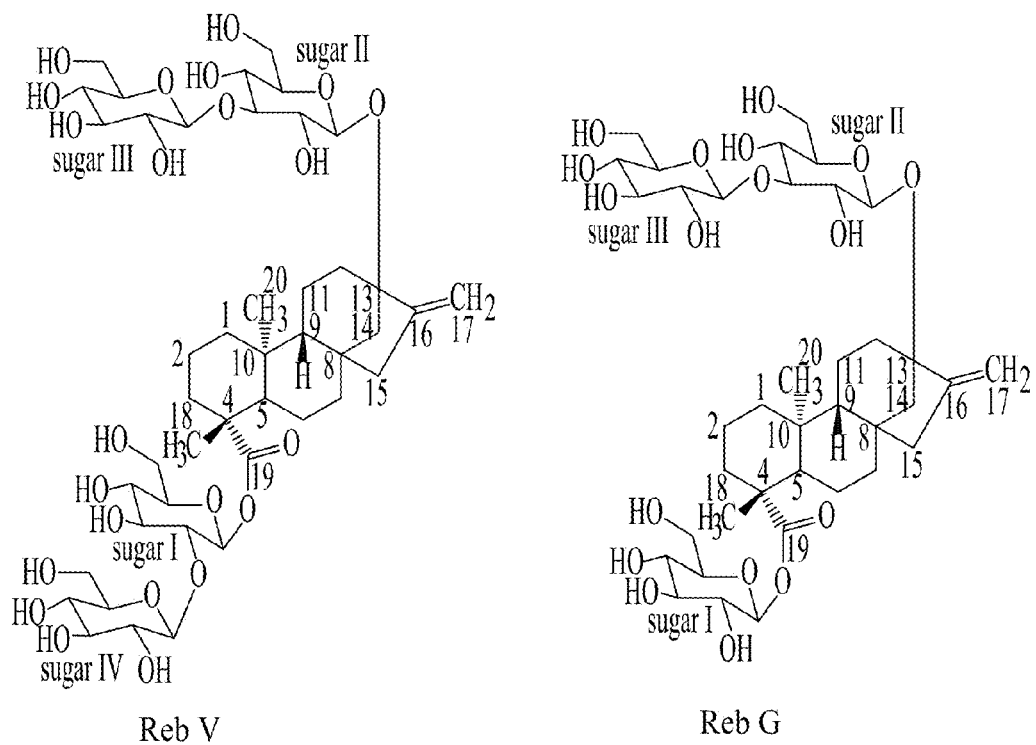
FIG. 17 depicts the structures of Reb V and Reb G.
Figure 18:
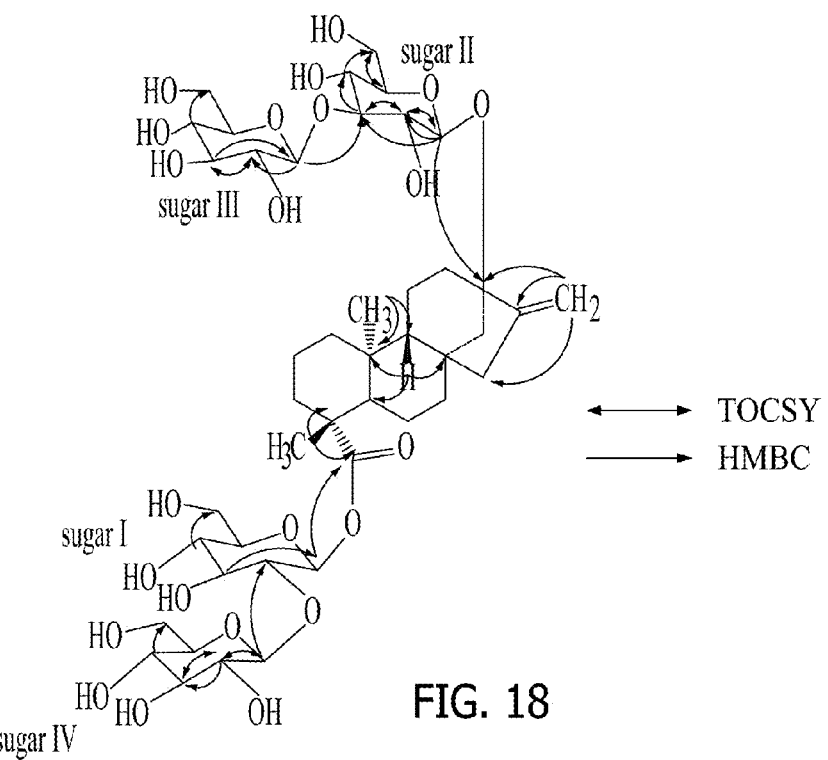
FIG. 18 depicts the key TOCSY and HMBC correlations of Reb V.

Based on the results from NMR spectral data and hydrolysis experiments of Reb V, it was concluded that there are four β-D-glucosyl units in its structure connected to the aglycone steviol. A close comparison of the $^1$H and $^{13}$C NMR values of Reb V with Reb G suggested the presence of a steviol aglycone moiety with a 3-O-β-D-glucobiosyl unit at C-13 in the form of ether linkage and another β-D-glucosyl unit at C-19 position in the form of an ester linkage, leaving the assignment of the fourth β-D-glucosyl moiety (FIG. 17). The downfield shift for both the $^1$H and $^{13}$C chemical shifts at 2-position of sugar I of the β-D-glucosyl moiety supported the presence of β-D-glucosyl unit at this position. The structure was further supported by the key TOCSY and HMBC correlations as shown in FIG. 18. Based on the results of NMR and mass spectral data as well as hydrolysis studies, the structure of Reb V produced by the enzymatic conversion of Reb G was deduced as 13-[(3-O-β-D-glucopyranosyl-β-D-glucopyranosyl)oxy] ent-kaur-16-en-19-oic acid-(2-O-β-D-glucopyranosyl-β-D-glucopyranosyl) ester.

Acid hydrolysis of Reb V. To a solution of Reb V (5 mg) in MeOH (10 ml) was added 3 ml of 5% $H_2SO_4$ and the mixture was refluxed for 24 hours. The reaction mixture was then neutralized with saturated sodium carbonate and extracted with ethyl acetate (EtOAc) (2×25 ml) to give an aqueous fraction containing sugars and an EtOAc fraction containing the aglycone part. The aqueous phase was concentrated and compared with standard sugars using the TLC systems EtOAc/n-butanol/water (2:7:1) and $CH_2Cl_2$/MeOH/water (10:6:1); the sugars were identified as D-glucose.

Enzymatic hydrolysis of Reb V. Reb V (1 mg) was dissolved in 10 ml of 0.1 M sodium acetate buffer, pH 4.5 and crude pectinase from *Aspergillus niger* (50 uL, Sigma-Aldrich, P2736) was added. The mixture was stirred at 50° C. for 96 hr. The product precipitated out during the reaction from the hydrolysis of 1 was identified as steviol by comparison of its co-TLC with standard compound and $^1$H NMR spectral data. A compound named Reb V was confirmed as 13-[(3-O-β-D-glucopyranosyl-β-D-glucopyranosyl)oxy] ent-kaur-16-en-19-oic acid-(2-O-β-D-glucopyranosyl-β-D-glucopyranosyl) ester on the basis of extensive 1D and 2D NMR as well as high resolution mass spectral data and hydrolysis studies.

Example 22

In this Example, the structure of Reb W was analyzed by NMR.

The material used for the characterization of Reb W was produced by using enzymatic conversion of Reb V and purified by HPLC. HRMS data were generated with a LTQ Orbitrap Discovery HRMS instrument, with its resolution set to 30 k. Scanned data from m/z 150 to 1500 in positive ion electrospray mode. The needle voltage was set to 4 kV; the other source conditions were sheath gas=25, aux gas=0, sweep gas=5 (all gas flows in arbitrary units), capillary voltage=30V, capillary temperature=300 C, and tube lens voltage=75. Sample was diluted with 2:2:1 acetonitrile:methanol:water (same as infusion eluent) and injected 50 microliters. NMR spectra were acquired on Bruker Avance DRX 500 MHz or Varian INOVA 600 MHz instruments using standard pulse sequences. The 1D ($^1$H and $^{13}$C) and 2D (TOCSY, HMQC, and HMBC) NMR spectra were performed in $C_5D_5N$.

The molecular formula of Reb W has been deduced as $C_{50}H_{80}O_{28}$ on the basis of its positive high resolution (HR) mass spectrum which showed adduct ions corresponding to [M+Na]$^+$ at m/z 1151.4708; this composition was supported by the $^{13}$C NMR spectral data. The $^1$H NMR spectral data of Reb W showed the presence of two methyl singlets at δ 0.92 and 1.39, two olefinic protons as singlets at δ 5.10 and 5.73 of an exocyclic double bond, nine sp3 methylene and two sp3 methine protons between δ 0.72-2.72, characteristic for the ent-kaurane diterpenoids isolated earlier from the genus *Stevia*. The basic skeleton of ent-kaurane diterpenoids was supported by the TOCSY studies which showed key correlations: H-1/H-2; H-2/H-3; H-5/H-6; H-6/H-7; H-9/H-11; H-11/H-12. The $^1$H NMR spectrum of Reb W also showed the presence of five anomeric protons resonating at δ 5.10, 5.34, 5.41, 5.81, and 6.14; suggesting five sugar units in its structure. Acid hydrolysis of Reb W with 5% $H_2SO_4$ afforded D-glucose which was identified by direct comparison with authentic sample by TLC. Enzymatic hydrolysis of Reb W furnished an aglycone which was identified as steviol by comparison of $^1$H NMR and co-TLC with standard compound. The large coupling constants observed for the five anomeric protons of the glucose moieties at δ 5.10 (d, J=7.4 Hz), 5.34 (d, J=7.9 Hz), 5.41 (d, J=7.9 Hz), 5.89 (d, J=7.9 Hz), and 6.14 (d, J=7.9 Hz), suggested their (β-orientation as reported for steviol glycosides [1-5, 9-13]. The $^1$H and $^{13}$C NMR values for Reb W were assigned on the basis of TOCSY, HMQC and HMBC data and are given in Table 4.

TABLE 4

$^1$H and $^{13}$C NMR spectral data (chemical shifts and coupling constants) for Reb W and Reb V$^{a-c}$.

| | Reb W | | Reb V | |
|---|---|---|---|---|
| Position | $^1$H NMR | $^{13}$C NMR | $^1$H NMR | $^{13}$C NMR |
| 1 | 0.72 m, 1.67 m | 41.0 | 0.78 m, 1.69 m | 41.1 |
| 2 | 1.42 m, 2.18 m | 20.4 | 1.44 m, 2.20 m | 20.4 |
| 3 | 1.06 m, 2.72 d (13.4) | 38.6 | 1.05 m, 2.70 d (11.6) | 38.4 |
| 4 | — | 44.8 | — | 44.8 |

TABLE 4-continued $^1$H and $^{13}$C NMR spectral data (chemical shifts and coupling constants) for Reb W and Reb V$^{a-c}$.

| | Reb W | | Reb V | |
|---|---|---|---|---|
| Position | $^1$H NMR | $^{13}$C NMR | $^1$H NMR | $^{13}$C NMR |
| 5 | 1.34 m | 57.9 | 1.32 m | 57.9 |
| 6 | 1.84 m, 2.18 m | 22.8 | 1.87 m, 2.24 m | 22.7 |
| 7 | 1.07 m, 1.69 m | 42.3 | 1.07 m, 1.72 m | 42.2 |
| 8 | — | 42.4 | — | 42.5 |
| 9 | 0.90 d (5.8) | 54.5 | 0.92 d (7.6) | 54.5 |
| 10 | — | 40.1 | — | 40.2 |
| 11 | 1.66 m | 21.0 | 1.75 m | 21.0 |
| 12 | 2.20 m, 2.39 m | 38.3 | 2.26 m, 2.38 m | 38.3 |
| 13 | — | 87.8 | — | 87.6 |
| 14 | 1.63 m, 2.06 m | 44.8 | 1.78 m, 2.50 m | 44.8 |
| 15 | 2.06 m, 2.04 m | 48.8 | 2.06 m, 2.32 m | 48.9 |
| 16 | — | 153.5 | — | 153.7 |
| 17 | 5.10 s, 5.73 s | 105.9 | 5.00 s, 5.49 s | 105.7 |
| 18 | 1.39 s | 29.4 | 1.32 s | 29.6 |
| 19 | — | 176.5 | — | 176.4 |
| 20 | 0.92 s | 16.6 | 1.25 s | 16.7 |
| 1' | 6.14 d (7.9) | 94.1 | 6.16 d (7.6) | 94.2 |
| 2' | 3.98 m | 79.6 | 4.01 m | 80.7 |
| 3' | 4.20 m | 88.9 | 4.09 m | 79.3 |
| 4' | 4.34 m | 70.0 | 4.34 m | 71.2 |
| 5' | 4.24 m | 79.4 | 4.22 m | 79.9 |
| 6' | 4.02 m, 4.39 | 62.6 | 4.04 m, 4.44 dd (3.2, 7.6) | 62.6 |
| 1" | 5.10 d (7.4) | 99.5 | 5.06 d (7.4) | 99.6 |
| 2" | 3.90 m | 74.7 | 3.92 m | 74.7 |
| 3" | 4.04 m | 89.3 | 4.06 m | 89.3 |
| 4" | 4.25 m | 70.4 | 4.23 m | 70.3 |
| 5" | 3.98 m | 78.6 | 4.02 m | 78.2 |
| 6" | 4.27 m, 4.54 m | 62.9 | 4.27 m, 4.56 dd (2.8, 8.4) | 63.0 |
| 1''' | 5.34 d (7.9) | 106.3 | 5.27 d (8.4) | 106.4 |
| 2''' | 4.12 m | 76.1 | 4.14 m | 76.1 |
| 3''' | 4.33 m | 79.2 | 4.37 m | 79.2 |
| 4''' | 4.25 m | 72.1 | 4.28 m | 72.2 |
| 5''' | 3.88 m | 78.8 | 3.89 m | 78.8 |
| 6''' | 4.16 m, 4.53 m | 63.0 | 4.18 m, 4.48 m | 63.2 |
| 1'''' | 5.41 d (7.9) | 105.3 | 5.27 d (8.4) | 105.7 |
| 2'''' | 4.12 m | 73.4 | 4.14 m | 76.5 |
| 3'''' | 4.28 m | 88.9 | 4.37 m | 79.6 |
| 4'''' | 4.20 m | 72.1 | 4.28 m | 72.5 |
| 5'''' | 3.78 m | 79.0 | 3.89 m | 79.0 |
| 6'''' | 4.08 m, 4.42 m | 62.9 | 4.18 m, 4.48 m | 63.5 |
| 1''''' | 5.81 d (7.9) | 104.0 | | |
| 2''''' | 4.09 m | 77.2 | | |
| 3''''' | 4.24 m | 79.3 | | |
| 4''''' | 4.14 m | 72.0 | | |
| 5''''' | 3.76 m | 79.2 | | |
| 6''''' | 4.04 m, 4.36 m | 62.3 | | |

$^a$assignments made on the basis of TOCSY, HMQC and HMBC correlations;
$^b$Chemical shift values are in δ (ppm);
$^c$Coupling constants are in Hz.

Figure 19:
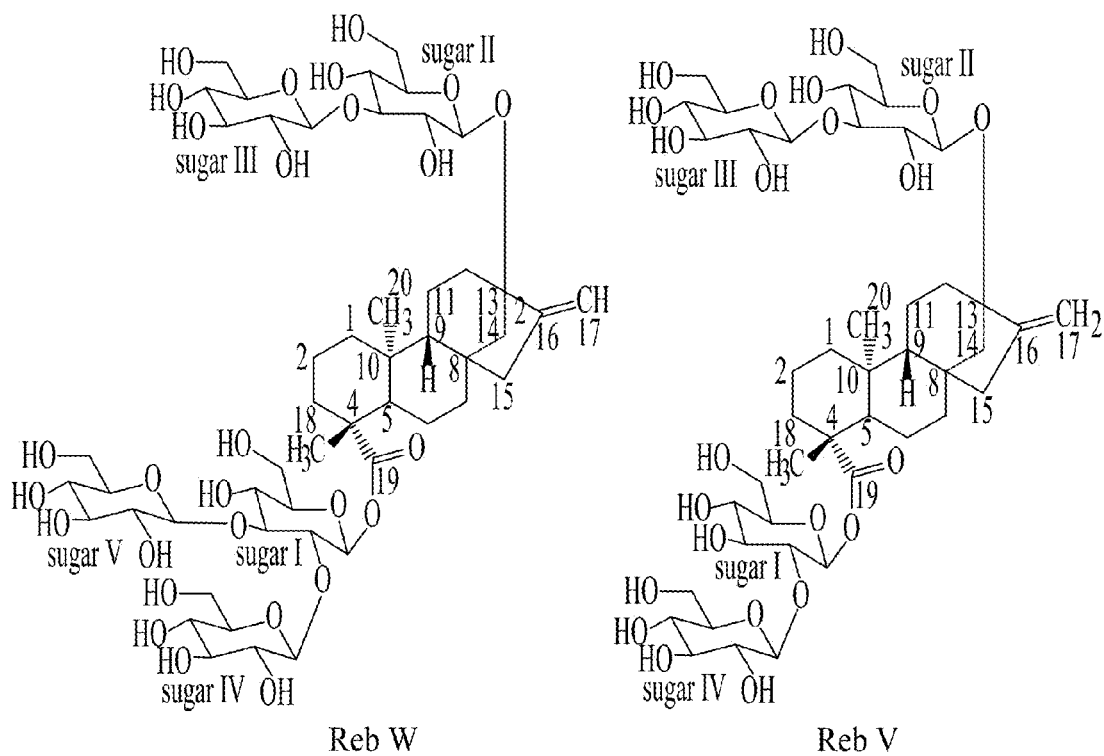
FIG. 19 depicts the structures of Reb W and Reb V.
Figure 20:
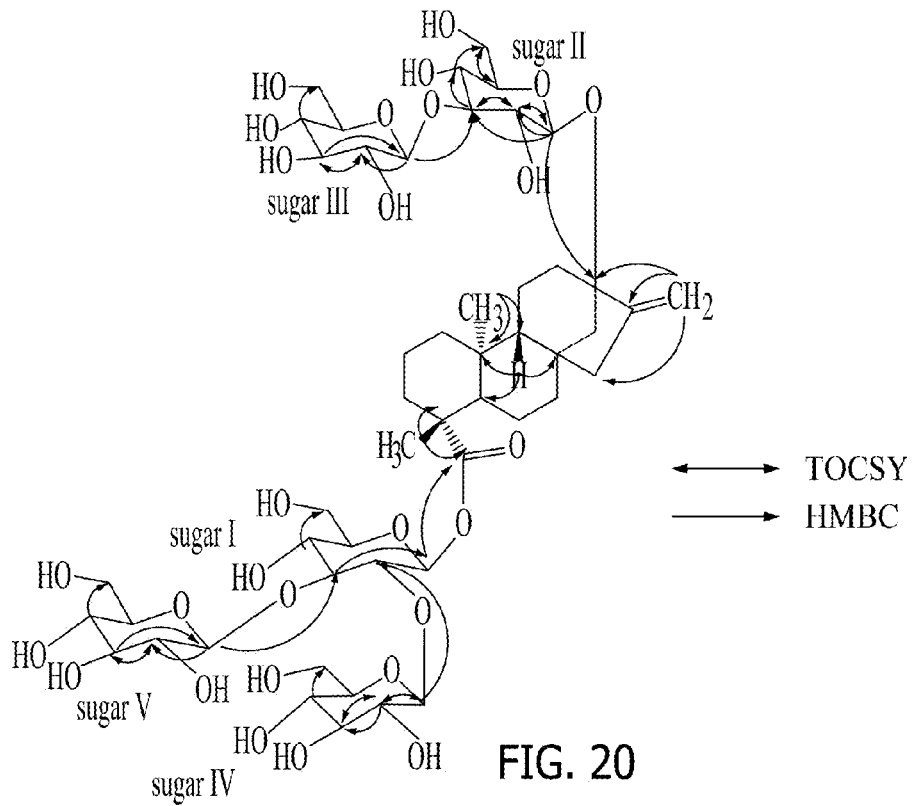
FIG. 20 depicts the key TOCSY and HMBC correlations of Reb W.
Figure 21A:
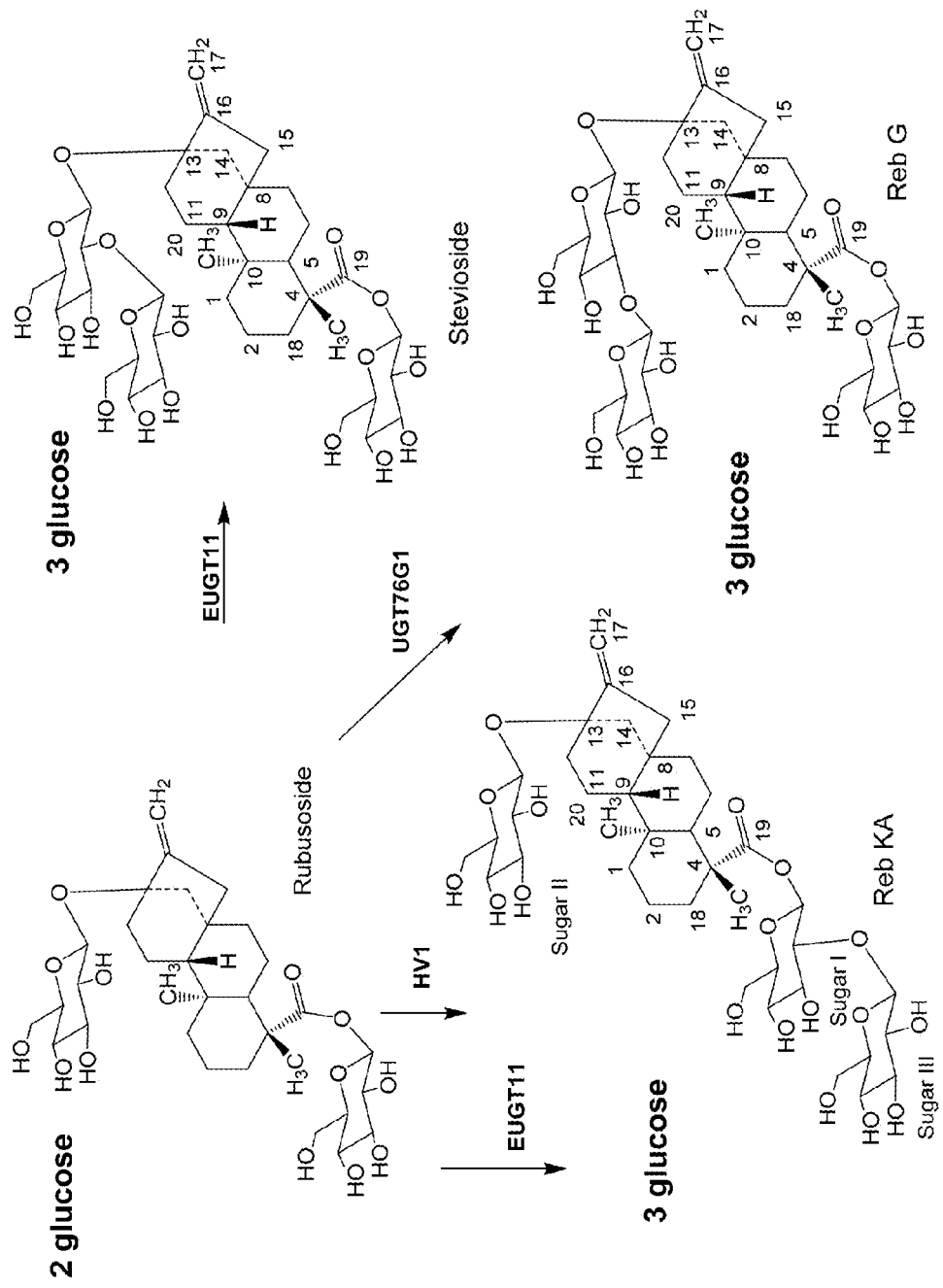
FIG. 21A, FIG. 21B, FIG. 21C, and FIG. 21D depict the biosynthesis pathway of steviol glycosides.
Figure 21B:
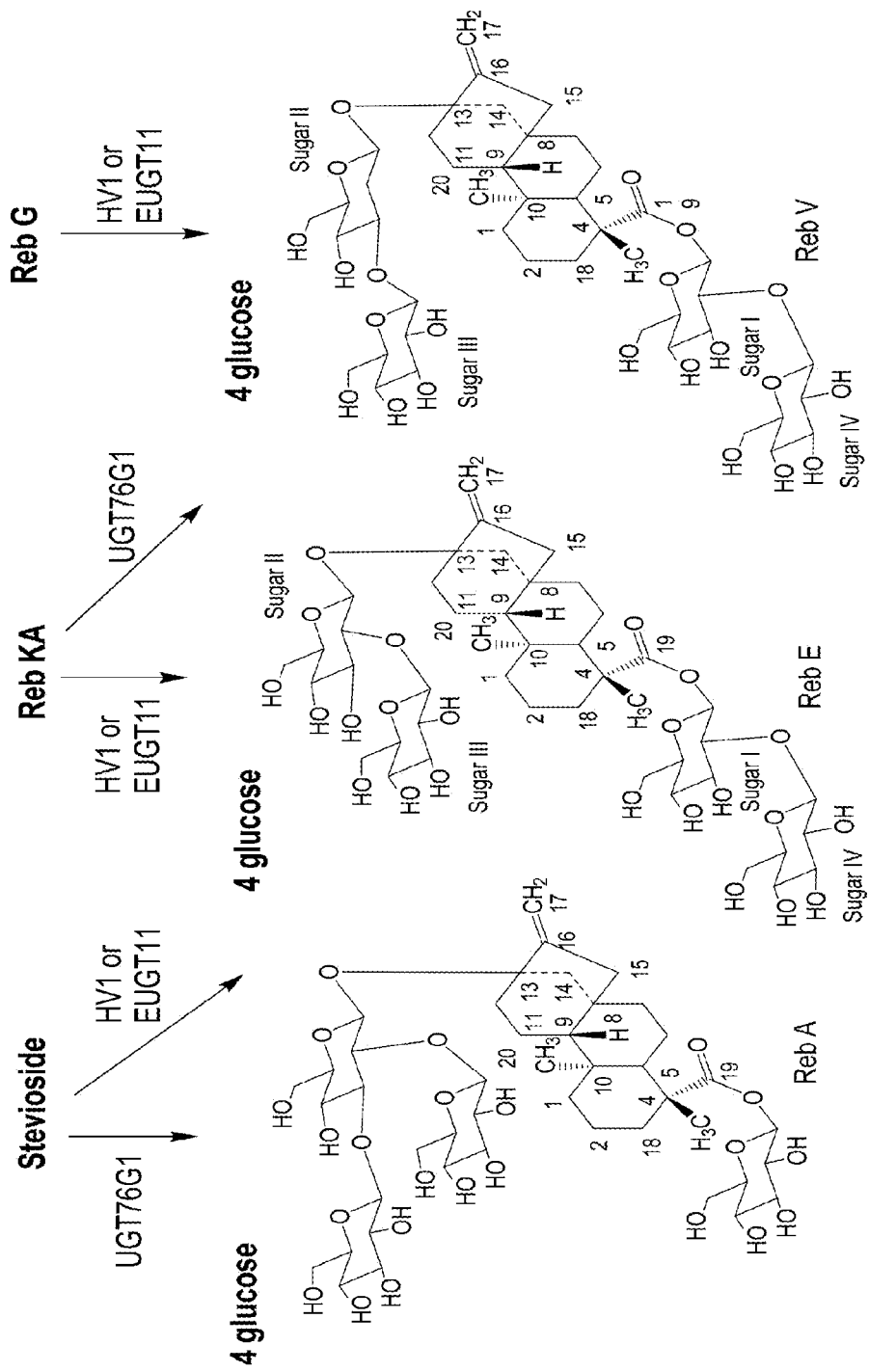
Figure 21C:
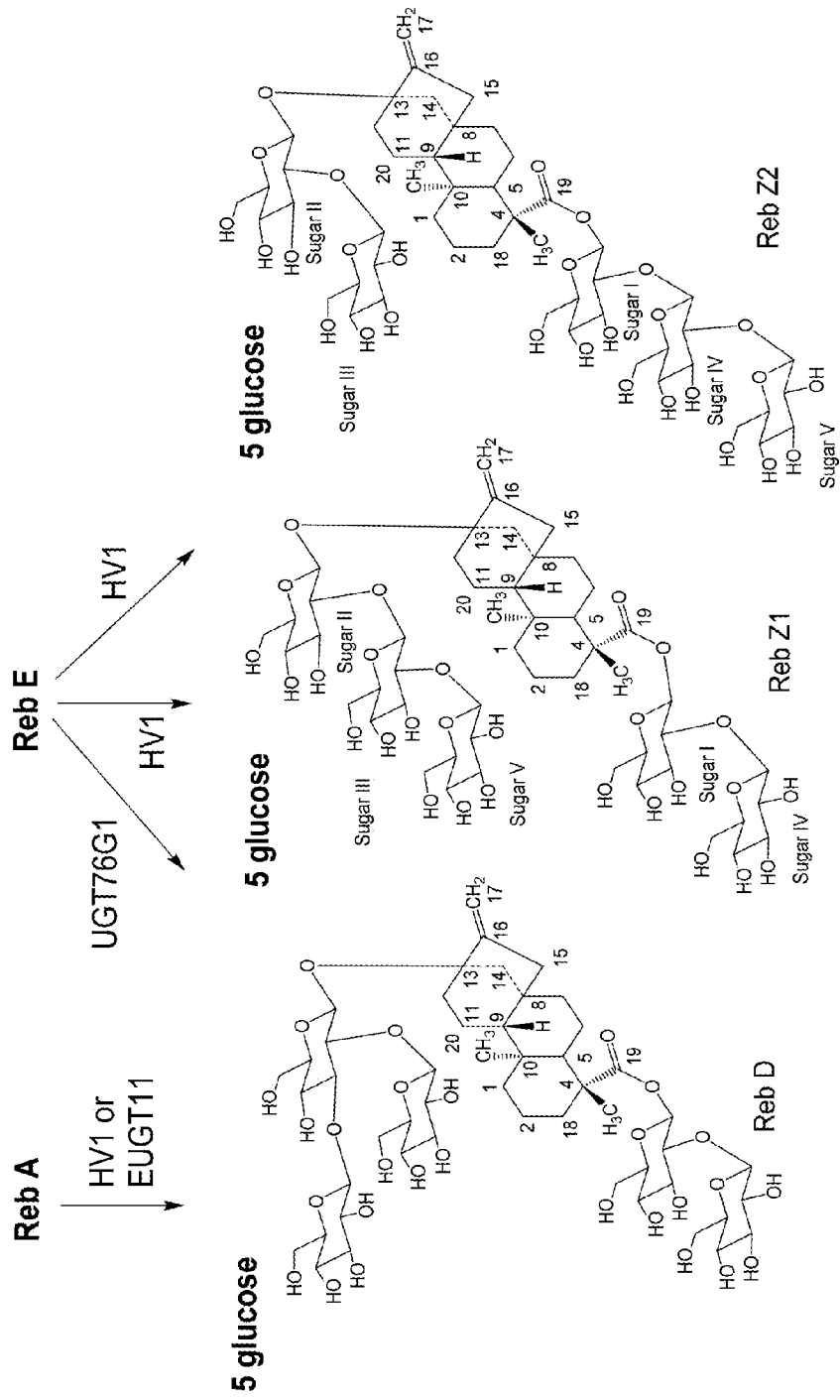
Figure 21D:
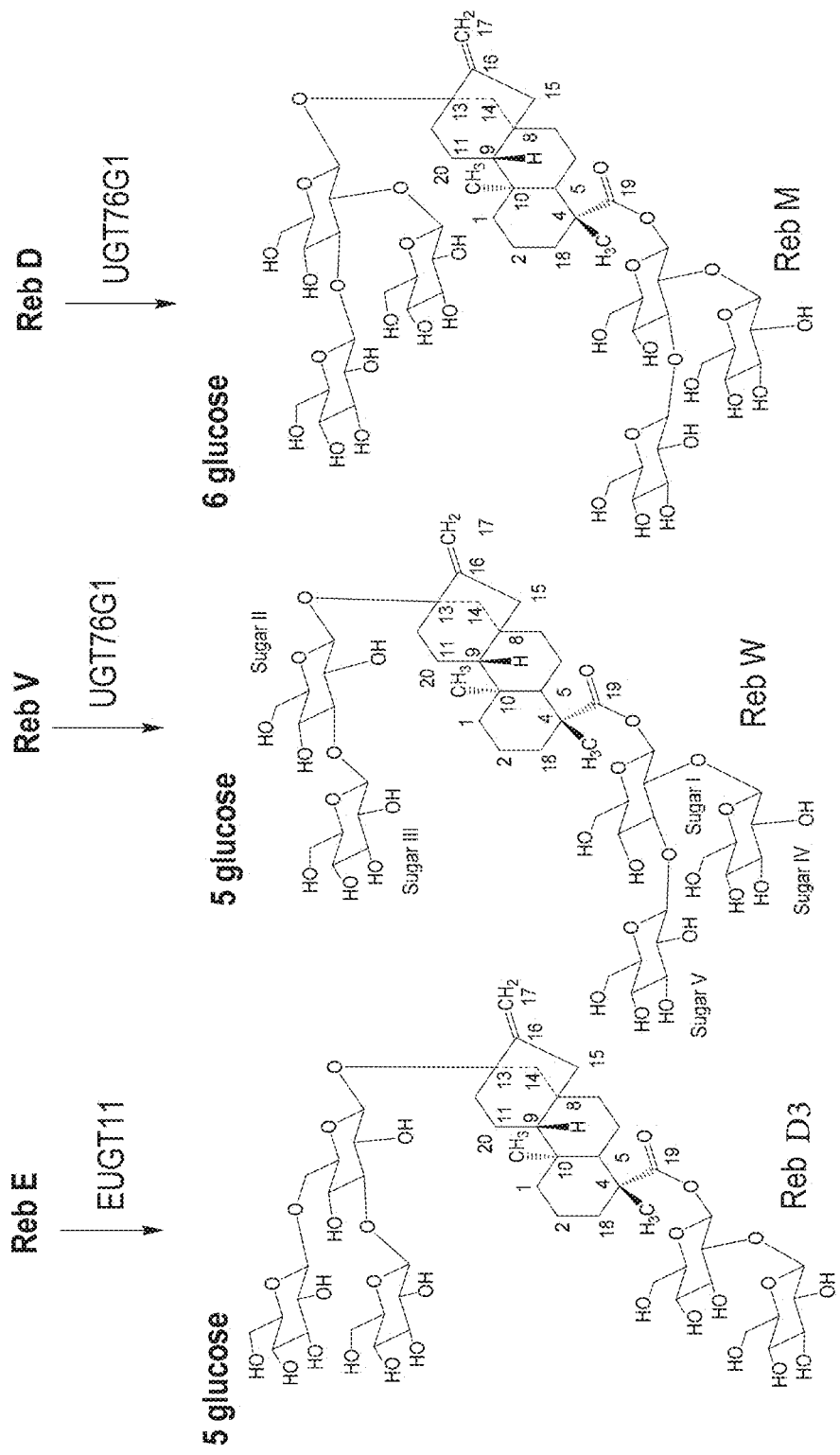

Based on the results from NMR spectral data and hydrolysis experiments of Reb W, it was concluded that there are five β-D-glucosyl units in its structure connected to the aglycone steviol. A close comparison of the $^1$H and $^{13}$C NMR values of Reb W with Reb V suggested the presence of a steviol aglycone moiety with a 3-O-β-D-glucobiosyl unit at C-13 in the form of ether linkage and a 2-O-3-D-glucobiosyl unit at C-19 position in the form of an ester linkage, leaving the assignment of the fifth β-D-glucosyl moiety (FIG. 19). The downfield shift for both the $^1$H and $^{13}$C chemical shifts at 3-position of sugar I of the β-D-glucosyl moiety supported the presence of β-D-glucosyl unit at this position. The structure was further supported by the key TOCSY and HMBC correlations as shown in FIG. 20. Based on the results of NMR and mass spectral data as well as hydrolysis studies, the structure of Reb W produced by the enzymatic conversion of Reb V was deduced as 13-[(3-O-β-D-glucopyranosyl-β-D-glucopyranosyl)oxy] ent-kaur-16-en-19-oic acid-[(2-O-β-D-glucopyranosyl-3-O-β-D-glucopyranosyl-β-D-glucopyranosyl) ester.

Acid hydrolysis of Reb W. To a solution of Reb W (5 mg) in MeOH (10 ml) was added 3 ml of 5% $H_2SO_4$ and the mixture was refluxed for 24 hours. The reaction mixture was then neutralized with saturated sodium carbonate and extracted with ethyl acetate (EtOAc) (2×25 ml) to give an aqueous fraction containing sugars and an EtOAc fraction containing the aglycone part. The aqueous phase was concentrated and compared with standard sugars using the TLC systems EtOAc/n-butanol/water (2:7:1) and $CH_2Cl_2$/MeOH/water (10:6:1); the sugars were identified as D-glucose.

Enzymatic hydrolysis of Reb W. Reb W (1 mg) was dissolved in 10 ml of 0.1 M sodium acetate buffer, pH 4.5 and crude pectinase from *Aspergillus niger* (50 uL, Sigma-Aldrich, P2736) was added. The mixture was stirred at 50° C. for 96 hr. The product precipitated out during the reaction and was filtered and then crystallized. The resulting product obtained from the hydrolysis of Reb W was identified as steviol by comparison of its co-TLC with standard compound and $^1$H NMR spectral data. A compound named Reb W was confirmed as 13-[(3-O-β-D-glucopyranosyl-β-D-glucopyranosyl)oxy] ent-kaur-16-en-19-oic acid-[(2-O-β-D-glucopyranosyl-3-O-β-D-glucopyranosyl-β-D-glucopyranosyl) ester, on the basis of extensive 1D and 2D NMR as well as high resolution mass spectral data and hydrolysis studies.

After NMR analysis, the structures of Reb V and Reb W were identified as novel steviol glycosides. The above results further demonstrated that UGT76G1 has not only a 1,3-13-O-glucose glycosylation activity but also 1,3-19-O-glucose glycosylation activity.

Example 23

In this Example, the structure of Reb M was analyzed by NMR.

The material used for the characterization of Reb M was produced from the enzymatic conversion of Reb D and purified by HPLC. HRMS data were generated with a LTQ Orbitrap Discovery HRMS instrument, with its resolution set to 30 k. Scanned data from m/z 150 to 1500 in positive ion electrospray mode. The needle voltage was set to 4 kV; the other source conditions were sheath gas=25, aux gas=0, sweep gas=5 (all gas flows in arbitrary units), capillary voltage=30V, capillary temperature=300 C, and tube lens voltage=75. Sample was diluted with 2:2:1 acetonitrile:methanol:water (same as infusion eluent) and injected 50 microliters.

NMR spectra were acquired on Bruker Avance DRX 500 MHz or Varian INOVA 600 MHz instruments using standard pulse sequences. The 1D ($^1$H and $^{13}$C) and 2D (COSY, HMQC, and HMBC) NMR spectra were performed in $C_5D_5N$.

The molecular formula of compound Reb M has been deduced as $C_{56}H_{90}O_{33}$ on the basis of its positive high resolution (HR) mass spectrum which showed an [M+NH$_4$+CH$_3$CN]$^+$ ion at m/z 1349.5964; this composition was supported by $^{13}$C NMR spectral data. The $^1$H NMR spectrum of Reb M showed the presence of two methyl singlets at δ 1.35 and 1.42, two olefinic protons as singlets at δ 4.92 and 5.65 of an exocyclic double bond, nine methylene and two methine protons between δ 0.77-2.77 characteristic for the ent-kaurane diterpenoids isolated earlier from the genus *Stevia*. The basic skeleton of ent-kaurane diterpenoids was supported by COSY (H-1/H-2; H-2/H-3; H-5/H-6; H-6/H-7; H-9/H-11; H-11/H-12) and HMBC (H-1/C-2, C-10; H-3/C-1, C-2, C-4, C-5, C-18, C-19; H-5/C-4, C-6, C-7, C-9, C-10, C-18, C-19, C-20; H-9/C-8, C-10, C-11, C-12, C-14, C-15; H-14/C-8, C-9, C-13, C-15, C-16 and H-17/C-13, C-15, C-16) correlations. The $^1$H NMR spectrum of Reb M also showed the presence of anomeric protons resonating at δ 5.33, 5.47, 5.50, 5.52, 5.85, and 6.43; suggesting six sugar units in its structure. Enzymatic hydrolysis of Reb M furnished an aglycone which was identified as steviol by comparison of co-TLC with standard compound. Acid hydrolysis of Reb M with 5% $H_2SO_4$ afforded glucose which was identified by direct comparison with authentic samples by TLC. The $^1$H and $^{13}$C NMR values for selected protons and carbons in Reb M were assigned on the basis of TOCSY, HMQC and HMBC correlations (Table 5).

Figure 26:
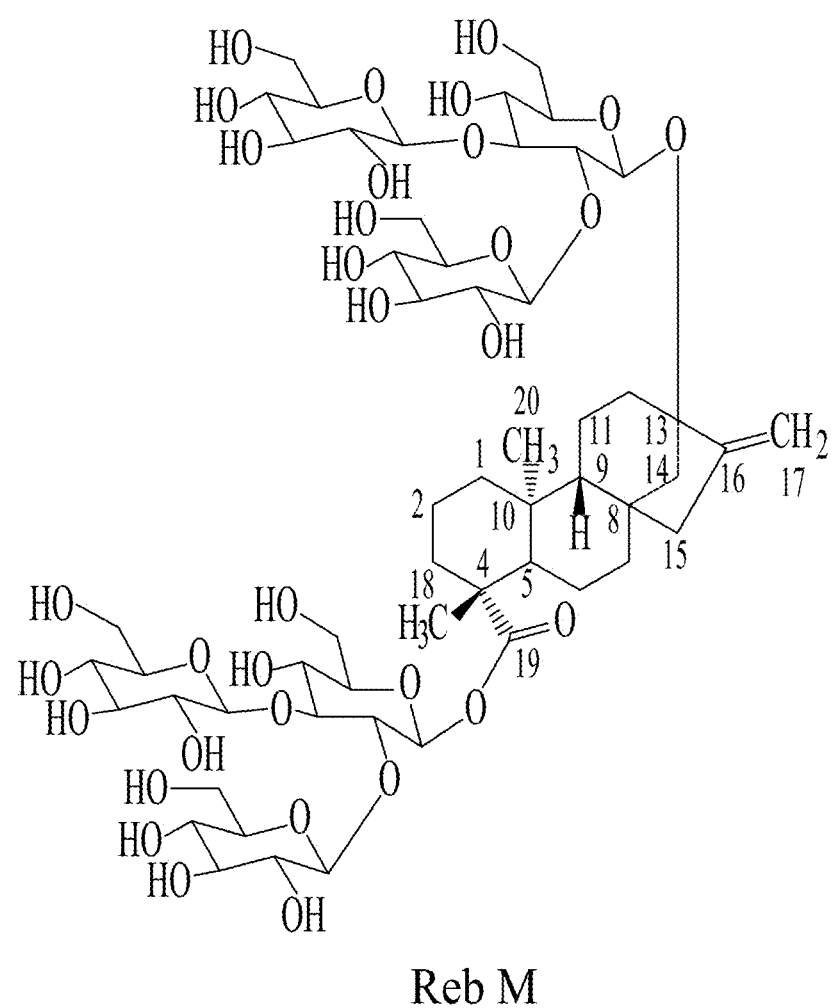
FIG. 26 depicts the structure of Reb M.
Figure 27:
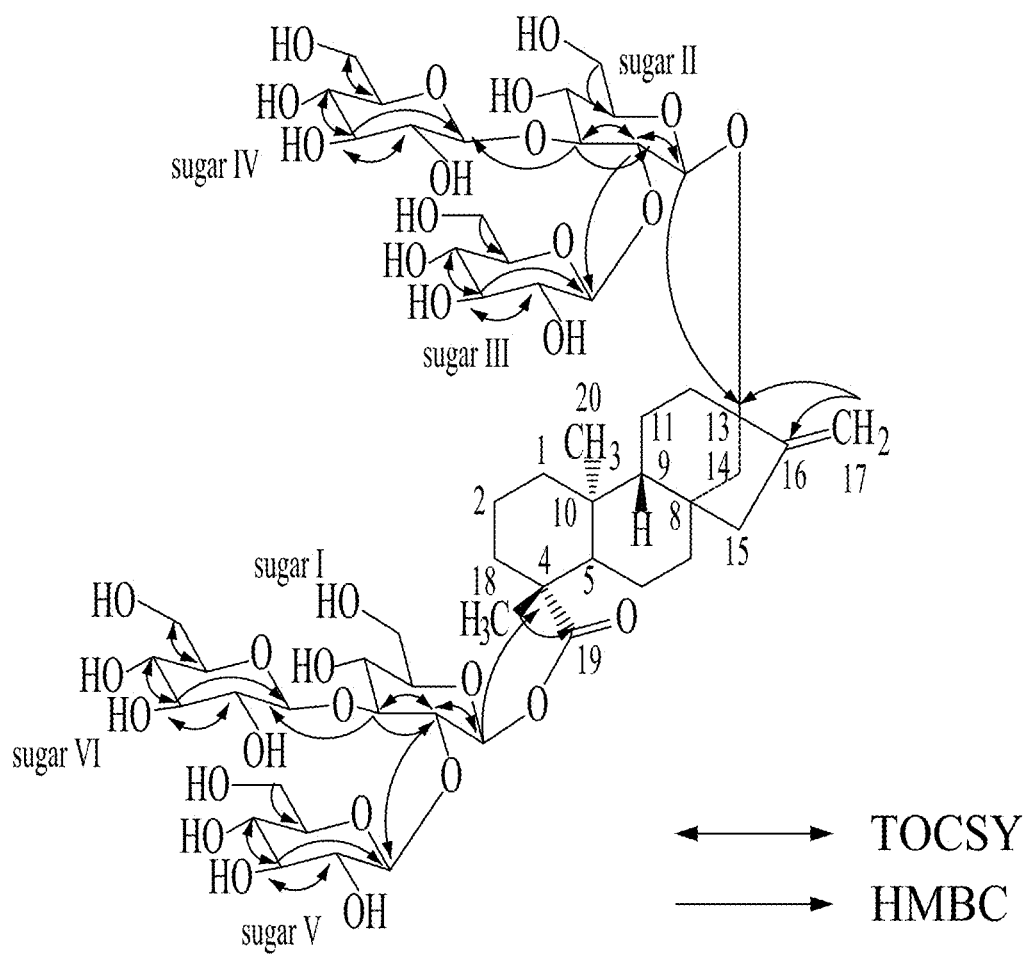
FIG. 27 depicts the key TOCSY and HMBC correlations of Reb M.

Based on the results from NMR spectral data of Reb M, it was concluded that there are six glucosyl units in its structure (FIG. 26). A close comparison of the $^1$H and $^{13}$C NMR spectrum of Reb M with rebaudioside D suggested that Reb M is also a steviol glycoside which has three glucose residues that are attached at the C-13 hydroxyl as a 2,3-branched glucotriosyl substituent and 2-substituted glucobiosyl moiety in the form of an ester at C-19 leaving the assignment of the additional glucosyl moiety. The key TOCSY and HMBC correlations shown in FIG. 27 suggested the placement of the sixth glucosyl moiety at C-3 position of Sugar I. The large coupling constants observed for the six anomeric protons of the glucose moieties at δ 5.33 (d, J=8.4 Hz), 5.47 (d, J=7.8 Hz), 5.50 (d, J=7.4 Hz), 5.52 (d, J=7.4 Hz), 5.85 (d, J=7.4 Hz) and 6.43 (d, J=7.8 Hz), suggested their β-orientation as reported for steviol glycosides. Based on the results of NMR and mass spectral studies and in comparison with the spectral values of rebaudioside M reported from the literature, structure of Reb M produced by enzymatic reaction was assigned as 13-[(2-O-β-D-glucopyranosyl-3-O-β-D-glucopyranosyl-β-D-glucopyranosyl) oxy] ent-kaur-16-en-19-oic acid-[(2-O-β-D-glucopyranosyl-3-O-β-D-glucopyranosyl-β-D-glucopyranosyl) ester.

TABLE 5

$^1$H and $^{13}$C NMR spectral data (chemical shifts and coupling constants) for Reb M produced by enzymatic reaction$^{a\text{-}c}$.

| Position | $^1$H NMR | $^{13}$C NMR |
|---|---|---|
| 1 | 0.77 t (12.4), 1.78 m | 40.7 |
| 2 | 1.35 m, 2.24 m | 20.0 |
| 3 | 1.01 m, 2.32 m | 38.8 |
| 4 | — | 44.7 |
| 5 | 1.08 d (12.4) | 57.8 |
| 6 | 2.23 m, 2.45 q (12.8) | 23.9 |
| 7 | 1.44 m, 1.83 m | 43.0 |
| 8 | — | 41.6 |
| 9 | 0.93 d (7.4) | 54.7 |
| 10 | — | 40.1 |
| 11 | 1.68 m, 1.82 m | 20.7 |
| 12 | 1.86 m, 2.28 m | 38.8 |
| 13 | — | 88.0 |
| 14 | 2.04 m, 2.77 m | 43.7 |
| 15 | 1.91 m, 2.03 m | 46.8 |
| 16 | — | 153.8 |
| 17 | 4.92 s, 5.65 s | 105.2 |
| 18 | 1.35 s | 28.7 |
| 19 | — | 177.4 |
| 20 | 1.42 s | 17.2 |
| 1' | 6.43 d (7.8) | 95.4 |
| 2' | 4.54 m | 77.3 |
| 3' | 4.58 m | 89.1 |
| 4' | 4.22 m | 70.5 |
| 5' | 4.16 m | 78.8 |
| 6' | 4.18 m, 4.35 m | 62.1 |
| 1" | 5.50 d (7.4) | 96.7 |
| 2" | 4.19 m | 81.9 |
| 3" | 5.03 m | 88.4 |
| 4" | 4.12 m | 70.8 |
| 5" | 3.98 m | 78.1 |
| 6" | 4.22 m, 4.36 m | 62.9 |
| 1''' | 5.52 d (7.4) | 105.4 |
| 2''' | 4.24 m | 76.0 |
| 3''' | 4.16 m | 78.9 |
| 4''' | 4.02 m | 73.6 |
| 5''' | 3.78 ddd (2.8, 6.4, 9.4) | 78.0 |
| 6''' | 4.32 m, 4.54 m | 64.4 |
| 1'''' | 5.47 d (7.8) | 104.4 |
| 2'''' | 4.00 m | 75.9 |
| 3'''' | 4.40 m | 78.2 |
| 4'''' | 4.12 m | 71.6 |
| 5'''' | 3.96 m | 78.4 |
| 6'''' | 4.20 m, 4.32 m | 62.5 |
| 1''''' | 5.85 d (7.4) | 104.7 |
| 2''''' | 4.20 m | 75.9 |
| 3''''' | 4.30 m | 78.9 |
| 4''''' | 4.14 m | 73.7 |
| 5''''' | 3.94 ddd (2.8, 6.4, 9.9) | 78.3 |
| 6''''' | 4.32 m, 4.67 d (10.6) | 64.4 |
| 1'''''' | 5.33 d (8.4) | 104.6 |
| 2'''''' | 3.98 m | 76.2 |
| 3'''''' | 4.43 m | 78.5 |
| 4'''''' | 4.16 m | 71.7 |
| 5'''''' | 3.88 ddd (2.1, 6.4, 9.4) | 78.9 |
| 6'''''' | 4.10 m, 4.35 m | 62.5 |

$^a$assignments made on the basis of TOCSY, HSQC and HMBC correlations;
$^b$Chemical shift values are in δ (ppm);
$^c$Coupling constants are in Hz.

Acid hydrolysis of compound 1: To a solution of produced Reb M (5 mg) in MeOH (10 ml) was added 3 ml of 5% $H_2SO_4$ and the mixture was refluxed for 24 hours. The reaction mixture was then neutralized with saturated sodium carbonate and extracted with ethyl acetate (EtOAc) (2×25 ml) to give an aqueous fraction containing sugars and an EtOAc fraction containing the aglycone part. The aqueous phase was concentrated and compared with standard sugars using the TLC systems EtOAc/n-butanol/water (2:7:1) and $CH_2Cl_2$/MeOH/water (10:6:1); the sugars were identified as D-glucose.

Enzymatic hydrolysis of compound: produced Reb M (1 mg) was dissolved in 10 ml of 0.1 M sodium acetate buffer, pH 4.5 and crude pectinase from *Aspergillus niger* (50 uL, Sigma-Aldrich, P2736) was added. The mixture was stirred at 50° C. for 96 hr. The product precipitated out during the reaction from the hydrolysis of 1 was identified as steviol by comparison of its co-TLC with standard compound and $^1$H NMR spectral data.

A compound named rebaudisode M (Reb M) was obtained was produced by bio-conversion. The complete $^1$H and $^{13}$C NMR spectral assignments for rebaudioside M (Reb M) were made on the basis of extensive 1D and 2D NMR as well as high resolution mass spectral data, which suggested the structure as 13-[(2-O-β-D-glucopyranosyl-3-O-β-D-glucopyranosyl-β-D-glucopyranosyl)oxy] ent-kaur-16-en-19-oic acid-[(2-O-β-D-glucopyranosyl-3-O-β-D-glucopyranosyl-β-D-glucopyranosyl)ester.

Example 24

In this Example, the biosynthesis pathway of steviol glycosides is discussed.

FIG. 21A, FIG. 21B, FIG. 21C, and FIG. 21D depict a scheme illustrating the novel pathways of steviol glycoside biosynthesis from rubusoside. As described herein, the recombinant HV1 polypeptide ("HV1") contains a 1,2-O-glucose glycosylation activity which transfers a second glucoside moiety to the C-2' of 19-O-glucose of rubusoside to produce rebaudioside KA ("Reb KA"); the recombinant EUGT11 polypeptide ("EUGT11") contains a 1,2-O-glucose glycosylation activity which transfers a second glucose moiety to the C-2' of 19-O-glucose of rubusoside to produce rebaudioside KA; or transfer a second glucose moiety to the C-2' of 13-O-glucose of rubusoside to produce stevioside; the recombinant UGT76G1 enzyme ("UGT76G1") contains a 1,3-O-glucose glycosylation activity which transfer a second glucose moiety to the C-3' of 13-O-glucose of rubusoside to produce rebaudioside G ("Reb G"). Both of HV1 and EUGT11 transfer a second sugar moiety to the C-2' of 19-O-glucose of rebaudioside G to produce rebaudioside V ("Reb V"), or transfer a second glucose moiety to the C-2' of 13-O-glucose of rebaudioside KA to produce rebaudioside E ("Reb E"). FIG. 21A, FIG. 21B, FIG. 21C, and FIG. 21D also show that a recombinant UGT76G1 enzyme catalyzes the reaction that transfers the third sugar moiety to C-3' of the C-19-O-glucose of rebaudioside V to produce rebaudioside W ("Reb W") and EUGT11 can continually transfer the third glucose moiety to C-6' of the C-13-O-glucose of rebaudioside E to produce rebaudioside D3. HV1 can transfer the third glucose moiety to C-2' of the C-13-O-glucose of rebaudioside E to produce rebaudioside Z1 ("Reb Z1"), and can transfer the third glucose moiety to C-2' of the C-19-O-glucose of rebaudioside E to produce rebaudioside Z2 ("Reb Z2"). Both of HV1 and EUGT11 can catalyze the conversion of stevioside to Reb E and the conversion of rebaudioside A ("Reb A") to rebaudioside D ("Reb D"). UGT76G1 can transfer the third glucose moiety to C-3' of the C-13-O-glucose of rebaudioside E ("Reb E") to form rebaudioside D ("Reb D"). UGT76G1 also catalyze the conversion of stevioside to rebaudioside ("Reb A") and the conversion of rebaudioside D ("Reb D") to rebaudioside M ("Reb M").

In view of the above, it will be seen that the several advantages of the disclosure are achieved and other advantageous results attained. As various changes could be made in the above methods and systems without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method for synthesizing rebaudioside E from rebaudioside KA, the method comprising:
adding to an in vitro reaction mixture:
(a) rebaudioside KA,
(b) substrates selected from the group consisting of sucrose, uridine diphosphate (UDP) and uridine diphosphate-glucose (UDP-glucose), and
(c) a UDP-glycosyltransferase selected from the group consisting of an HV1 having the amino acid sequence of SEQ ID NO:5, an EUGT11 having the amino acid sequence of SEQ ID NO: 3, and a UDP-glycosyltransferase fusion enzyme having the amino acid sequence of SEQ ID NO: 11; and
incubating the reaction mixture for a sufficient time to produce rebaudioside E, wherein a glucose is covalently coupled to the CT 13-O-glucose of rebaudioside KA to produce rebaudioside E.

2. The method of claim 1, further comprising adding a sucrose synthase to the reaction mixture.

3. The method of claim 2, wherein the sucrose synthase is an *Arabidopsis thaliana* sucrose synthase 1 having the amino acid sequence of SEQ ID NO: 7.

4. A method for synthesizing rebaudioside D3 from rubusoside, the method comprising:
(i) adding to an in vitro reaction mixture:
(a) rubusoside,
(b) substrates selected from the group consisting of sucrose, uridine diphosphate (UDP) and uridine diphosphate-glucose (UDP-glucose), and
(c) a UDP-glycosyltransferase fusion enzyme having the amino acid sequence of SEQ ID NO: 11;
(ii) incubating the reaction mixture for a sufficient time to produce a mixture of stevioside and rebaudioside KA, wherein a first glucose is covalently coupled to the rubusoside to produce a mixture of stevioside and rebaudioside KA;
(iii) further incubating the mixture of stevioside and rebaudioside KA with the substrates and an EUGT11 having the amino acid sequence of SEQ ID NO: 3 or the UDP-glycosyltransferase fusion enzyme to produce rebaudioside E, wherein a second glucose is covalently coupled to the stevioside and the rebaudioside KA to produce rebaudioside E; and
(iv) further incubating the rebaudioside E with the substrates and the EUGT11 or the UDP-glycosyltransferase fusion enzyme to produce rebaudioside D3, wherein a third glucose is covalently coupled to the rebaudioside E to produce rebaudioside D3.

5. A method for synthesizing rebaudioside D3 from rebaudioside KA, the method comprising:
adding to an in vitro reaction mixture:
(a) rebaudioside KA,
(b) substrates selected from the group consisting of sucrose, uridine diphosphate (UDP) and uridine diphosphate-glucose (UDP-glucose), and
(c) a UDP-glycosyltransferase selected from the group consisting of an EUGT11 having the amino acid sequence of SEQ ID NO: 3 and a UDP-glycosyltransferase fusion enzyme having the amino acid sequence of SEQ ID NO: 11; and
incubating the reaction mixture for a sufficient time to produce rebaudioside D3, wherein a first glucose is covalently coupled to the rebaudioside KA to produce rebaudioside E and a second glucose is covalently coupled to the rebaudioside E to produce rebaudioside D3.

6. The method of claim 5, further comprising adding a sucrose synthase to the reaction mixture.

7. The method of claim 6, wherein the sucrose synthase is an *Arabidopsis thaliana* sucrose synthase 1 having the amino acid sequence of SEQ ID NO: 7.

* * * * *

UNITED STATES PATENT AND TRADEMARK OFFICE
CERTIFICATE OF CORRECTION

PATENT NO.       : 9,783,566 B2
APPLICATION NO.  : 14/873481
DATED            : October 10, 2017
INVENTOR(S)      : Guohong Mao et al.

It is certified that error appears in the above-identified patent and that said Letters Patent is hereby corrected as shown below:

In the Claims

In Claim 1, Column 105, Line 47, the text:
"CT 13-O-glucose" should be replaced with the text --C2' 13-O-glucose--.

Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*